(12) United States Patent
Corbett et al.

(10) Patent No.: US 6,964,965 B2
(45) Date of Patent: Nov. 15, 2005

(54) SUBSTITUTED PYRAZINE DERIVATIVES

(75) Inventors: Jeffrey W. Corbett, Portage, MI (US); Michael Dalton Ennis, Mattawan, MI (US); Kristine E. Frank, Portage, MI (US); Jian-Min Fu, Kalamazoo, MI (US); Robert Louis Hoffman, Kalamazoo, MI (US); Patrick R. Verhoest, Augusta, MI (US)

(73) Assignee: Pharmacia & Upjohn, Kalamazoo, MI (US)

(*) Notice: Subject to any disclaimer, the term of this patent is extended or adjusted under 35 U.S.C. 154(b) by 112 days.

(21) Appl. No.: 10/417,867

(22) Filed: Apr. 17, 2003

(65) Prior Publication Data

US 2004/0053941 A1 Mar. 18, 2004

Related U.S. Application Data

(60) Provisional application No. 60/376,031, filed on Apr. 26, 2002.

(51) Int. Cl.$^7$ .................. A61K 31/497; A61K 31/4965; C07D 401/00; C07D 403/00; C07D 405/00

(52) U.S. Cl. .................. 514/252.1; 514/255.06; 544/405; 544/406; 544/407; 544/408; 544/409; 206/828

(58) Field of Search .................. 514/252.1, 255.06; 544/405, 406, 407, 408, 409; 206/828

(56) References Cited

U.S. PATENT DOCUMENTS

| | | | | |
|---|---|---|---|---|
| 5,795,905 A | * | 8/1998 | McCarthy et al. | 514/383 |
| 5,872,136 A | | 2/1999 | Anthony et al. | 514/341 |
| 5,880,140 A | | 3/1999 | Anthony | 514/333 |
| 5,883,105 A | | 3/1999 | Anthony | 514/277 |
| 6,043,260 A | | 3/2000 | Chen | 514/348 |
| 6,399,315 B1 | * | 6/2002 | Perrin et al. | 435/7.2 |

FOREIGN PATENT DOCUMENTS

| | | | | |
|---|---|---|---|---|
| EP | 1097709 A2 | 10/2000 | | A61K/31/426 |
| WO | WO 96/39374 | 12/1996 | | C07C/69/618 |
| WO | WO 97/36886 | 10/1997 | | C07D/285/06 |
| WO | WO 97/36898 | 10/1997 | | C07D/413/00 |
| WO | WO 98/27042 | 12/1997 | | C07C/43/20 |
| WO | WO 98/27179 | 12/1997 | | C09K/19/32 |
| WO | WO 98/29119 | 12/1997 | | A61K/31/44 |
| WO | WO 98/27045 | 6/1998 | | C07C/49/755 |
| WO | WO 98/38174 | 9/1998 | | C07D/241/20 |
| WO | WO 00/59902 | 10/2000 | | C07D/417/00 |
| WO | WO 01/55115 | 8/2001 | | C07D/213/82 |
| WO | WO 01/60806 | 8/2001 | | C07D/241/00 |
| WO | WO 02/19975 | 3/2002 | | A61K/7/06 |
| WO | WO 02/100838 A1 | 12/2002 | | C07D/241/12 |

OTHER PUBLICATIONS

Kehne and De Lombert, "Non-Peptidic CRF1 Receptor Antagonists for the Treatment of Anxiety, Depression and Stress Disorders" Current Drug Targets, vol. 1(5), pp.467–493 (2002).*
Dautzenberg and Hauger, "The CRF peptide family and their receptors: yet more partners discovered" Trends in Pharmacological Sciences, vol. 23(2), pp. 71–77 (Feb. 2002).*
Richard B. Silverman, The Organic Chemistry of Drug Design and Drug Action, pp. 352–400. © 1992 Academic Press, Inc.*
Hans Bundgaard, Design of Prodrugs, p. 1. © 1985 Elsevier Science Publishers.*
Al–Dabbagh and Smith, "Species differences in oxidative drug metabolism: some basic considerations." Archives of toxicology. Supplement. Archiv fur Toxikologie. supplement, vol. 7, pp. 219–231 (1984).*
Arato M. et al., Biol. Psychiatry, 1989, 25:355.
Banki C. M. et al., Am. J. Psychiatry, 1987, 144:873.
Berridge, C. W. and A. J. Dunn, Regul. Peptides, 1986, 16:83.
Berridge, C. W. and A. J. Dunn, Horm. Behav., 1987, 21:393.
Berridge, C. W. and A. J. Dunn, Brain Research Reviews, 1990, 15:71.
Blalock, Physiological Reviews, 1989, 69:1.
Britton, K. T. , et al., Pyschopharmacology, 1985, 86:170.
Britton, K. T. , Psychopharmacology, 1988, 94:306.
De Souze, E.B., Hosp. Practice, 1988, 23:59.
De Souza, E. B. et al., J. Neurosci., 1985, 5:3189.
France et al., Biol. Psychiatry, 1988, 28:86.
Gabry, K. E. , Molecular Psychiatry 2000, 7(5), 474–483.
Gold, P. W. et al., Am. J. Psychiatry, 1984, 141:619.
Gold, P. W. et al., New Engl. J. Med., 1986, 314:1129.
Grigoriadis, et al., Neuropsychopharmacology, 1989, 2:53.
Holsboer F. et al., Psychoneuroendocrinology, 1984, 9:147.
Koob G. F., Persp. Behav. Med., 1985, 2:39.
Morley, J.E. et al., Life Sci., 1987, 41:527.
Nakamura, H., Bull. Chem. Soc. Jpn., 1988, XP–00223312, vol. 61:3776.
Nemeroff, et al., Science, 1984, 226:1342.

(Continued)

Primary Examiner—James O. Wilson
Assistant Examiner—Zachary C. Tucker
(74) Attorney, Agent, or Firm—Peter C. Richardson; Lorrain B. Ling; Andrea E. Dorigo

(57) ABSTRACT

The present invention provides substituted pyrazine derivatives of Formula I,

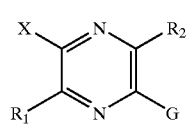

Formula I that are $CRF_1$ receptor antagonists, including human $CRF_1$ receptors. This invention also relates to use of compounds of the invention for treating a disorder or condition, the treatment of which can be effected or facilitated by antagonizing a CRF receptor, such as CNS disorders, particularly anxiety-related disorders and mood disorders.

24 Claims, No Drawings

OTHER PUBLICATIONS

Nemeroff C.B., et al., Arch. Gen Psychiatry, 1988, 45:577.
Rivier J. et al., Proc. Natl. Acad. Sci (USA), 1983, 80:4851.
Swerdlow, N. R., Psychopharmacology, 1986, 88:147–.
Vale W. et al, Science, 1981, 213:1394.
Vale W. et al, Rec. Prog. Horm. Res., 1983, 39:245.
Webster, E. L., J Rheumatol, Jun. 2002, 29(6):1252–61.
Zouboulis, C. C., Proc.Natl. Acad. Sci., 2001, 99, 7148–7153.
D. R. Britton, Intraventricular Corticotropin–Releasing Factor Enhances Behaviorial Effects of Novelty, Life Sciences, Vo. 3, 1982, pp. 363–367, Pergamon Press, U.S.A.

* cited by examiner

SUBSTITUTED PYRAZINE DERIVATIVES

CROSS-REFERENCE TO OTHER APPLICATIONS

This application claims the benefit of U.S. Provisional Application Ser. No. 60/376031 filed on 26 Apr. 2002.

FIELD OF THE INVENTION

The present invention relates generally to compounds that bind to CRF receptors, and particularly to substituted pyrazine derivatives as $CRF_1$ receptor antagonists and to the use thereof as a treatment for disorders that are associated with CRF or $CRF_1$ receptors.

BACKGROUND OF THE INVENTION

Corticotropin releasing factor (CRF) is a 41 amino acid peptide that is the primary physiological regulator of proopiomelanocortin (POMC) derived peptide secretion from the anterior pituitary gland [J. Rivier et al., *Proc. Natl. Acad. Sci (USA)* 80:4851 (1983); W. Vale et al., *Science* 213:1394 (1981)]. In addition to its endocrine role at the pituitary gland, CRF is known to have a broad extrahypothalmic distribution in the CNS, contributing therein to a wide spectrum of autonomic behavioral and physiological effects consistent with a neurotransmitter or neuromodulator role in the brain [W. Vale et al., *Rec. Prog. Horm. Res.* 39:245 (1983); G. F. Koob, *Persp. Behav. Med.* 2:39 (1985); E. B. De Souza et al., *J. Neurosci.* 5:3189 (1985)]. There is evidence that CRF plays a significant role in integrating the response in the immune system to physiological, psychological, and immunological stressors, in psychiatric disorders and neurological diseases including depression, anxiety-related disorders and feeding disorders, and in the etiology and pathophysiology of Alzheimer's disease, Parkinson's disease, Huntington's disease, progressive supranuclear palsy and amyotrophic lateral sclerosis, as they relate to the dysfunction of CRF neurons in the central nervous system [J. E. Blalock, *Physiological Reviews* 69:1 (1989); J. E. Morley, *Life Sci.* 41:527 (1987); E. B. De Souze, *Hosp. Practice* 23:59 (1988)].

It was shown that in individuals afflicted with affective disorder, or major depression, the concentration of CRF in the cerebral spinal fluid (CSF) is significantly increased. [C. B. Nemeroff et al., *Science* 226:1342 (1984); C. M. Banki et al., *Am. J. Psychiatry* 144:873 (1987); R. D. France et al., *Biol. Psychiatry* 28:86 (1988); M. Arato et al., *Biol. Psychiatry* 25:355 (1989)]. Furthermore, the density of CRF receptors is significantly decreased in the frontal cortex of suicide victims, consistent with a hypersecretion of CRF [C. B. Memeroff et al., *Arch. Gen. Psychiatry* 45:577 (1988)]. In addition, there is a blunted adrenocorticotropin (ACTH) response to CRF (i.v. administered) observed in depressed patients [P. W. Gold et al., *Am. J. Psychiatry* 141:619 (1984); F. Holsboer et al., *Psychoneuroendocrinology* 9:147 (1984); P. W. Gold et al., *New Engl. J. Med.* 314:1129 (1986)]. Preclinical studies in rats and non-human primates provide additional support for the hypothesis that hypersecretion of CRF may be involved in the symptoms seen in human depression [R. M. Sapolsky, *Arch. Gen. Psychiatry* 46:1047 (1989)]. There is also preliminary evidence that tricyclic antidepressants can alter CRF levels and thus modulate the numbers of receptors in the brain [Grigoriadis et al., *Neuropsychopharmacology* 2:53 (1989)].

CRF has also been implicated in the etiology of anxiety-related disorders. Anxiety disorders are a group of diseases, recognized in the art, that includes phobic disorders, anxiety states, post-traumatic stress disorder and atypical anxiety disorders [The Merck Manual of Diagnosis and Therapy, 16th edition (1992)]. Emotional stress is often a precipitating factor in anxiety disorders, and such disorders generally respond to medications that lower response to stress. Excessive levels of CRF are known to produce anxiogenic effects in animal models [see, e.g., Britton et al., 1982; Berridge and Dunn, 1986 and 1987]. Interactions between benzodiazepine/non-benzodiazepine anxiolytics and CRF have been demonstrated in a variety of behavioral anxiety models [D. R. Britton et al., *Life Sci.* 31:363 (1982); C. W. Berridge and A. J. Dunn, *Regul. Peptides* 16:83 (1986)]. Studies using the putative CRF receptor antagonist α-helical ovine CRF (9–41) in a variety of behavioral paradigms demonstrates that the antagonist produces "anxiolytic-like" effects that are qualitatively similar to the benzodiazepines [C. W. Berridge and A. J. Dunn, *Horm. Behav.* 21:393 (1987), *Brain Research Reviews* 15:71 (1990); G. F. Koob and K. T. Britton, In: *Corticotropin-Releasing Factor: Basic and Clinical Studies of a Neuropeptide*, E. B. De Souza and C. B. Nemeroff eds., CRC Press p. 221 (1990)]. Neurochemical, endocrine and receptor binding studies have all demonstrated interactions between CRF and benzodiazepine anxiolytics, providing further evidence for the involvement of CRF in these disorders. Chlordiazepoxide attenuates the "anxiogenic" effects of CRF both in the conflict test [K. T. Britton et al., *Psychopharmacology* 86:170 (1985); K. T. Britton et al., *Psychopharmacology* 94:306 (1988)] and in the acoustic startle test [N. R. Swerdlow et al., *Psychopharmacology* 88:147 (1986)] in rats. The benzodiazepine receptor antagonist Ro 15–1788, which was without behavioral activity alone in the operant conflict test, reversed the effects of CRF in a dose-dependent manner while the benzodiazepine inverse agonist FG 7142 enhanced the actions of CRF [K. T. Britton et al., *Psychopharmacology* 94:396 (1988)].

The use of $CRF_1$ antagonists for the treatment of Syndrome X has also been described in U.S. patent application Ser. No. 09/696,822, filed Oct. 26, 2000, and European Patent Application No. 003094414, filed Oct. 26, 2000. Methods for using $CRF_1$ antagonists to treat congestive heart failure are described in U.S. Ser. No. 09/248,073, filed Feb. 10, 1999, now U.S. Pat. No. 6,043,260 (Mar. 28, 2000).

It has also been suggested that $CRF_1$ antagonists are useful for treating arthritis and inflammation disorders [Webster E L, et al.: *J Rheumatol* June 2002; 29(6):1252–61; Murphy E P, et al: *Arthritis Rheum* April 2001; 44(4): 782–93]; stress-related gastrointestinal disorders [Gabry, K. E. et al: *Molecular Psychiatry* (2002), 7(5), 474–483]; and skin disorders [Zouboulis, C. C. et al: *Proc. Natl. Acad. Sci.* 2002, 99, 7148–7153.]

It was disclosed recently that, in an animal model, stress-induced exacerbation of chronic contact dermatitis is blocked by a selective $CRF_1$ antagonist, suggesting that that $CRF_1$ is involved in the stress-induced exacerbation of chronic contact dermatitis and that $CRF_1$ antagonist may be useful for treating this disorder. [Kaneko K, Kawana S, Arai K, Shibasaki T. *Exp Dermatol,* 12(1):47–52 (2003).

WO 0219975 discloses hair growth stimulants containing a corticotropin release factor $CRF_1$ receptor antagonist as the active ingredient. It was shown that $CRF_1$ receptor antagonist 2-[N-(2-methylthio-4-isopropylphenyl)-N-ethylamino]-4-[4-(3-fluorophenyl)-1,2,3,6-tetrahydropyridine-1-yl]-6-methylpyrimidine showed keratinocyte cell proliferation promoting effect in cultured human epidermal keratinocyte cells.

WO 0160806 discloses compounds as antagonists of CRF$_1$ receptors.

WO 0155115 discloses compounds as activators of caspases and inducers of apoptosis.

WO 0059902 discloses compounds as factor Xa inhibitors.

WO 9639374 discloses compounds having retinoid-like biological activity.

The following patents or patent applications disclose compounds as inhibitors of farnesyl-protein transferase: WO 9829119, WO 9736886, WO 9736898, and U.S. Pat. Nos. 5,872,136, 5,880,140, and 5,883,105.

The following patent applications disclose compounds and their use in liquid crystal mixtures: WO9827042, WO9827045, and WO9827179.

It is an object of the invention to provide novel pyrazine derivatives, which are CRF$_1$ receptor antagonists.

It is another object of the invention to provide novel compounds as treatment of disorders or conditions that are associated with CRF or CRF$_1$ receptors, such as anxiety disorders, depression, and stress related disorders.

It is another object of the invention to provide a method of treating disorders or conditions that are associated with CRF or CRF$_1$ receptors, such as anxiety disorders, depression, and stress related disorders.

It is yet another object of the invention to provide a pharmaceutical composition useful for treating disorders or conditions that are associated with CRF or CRF$_1$ receptors, such as anxiety disorders, depression, and stress related disorders.

There are other objects of the invention which will be evident or apparent from the description of the invention in the specification of the application.

SUMMARY OF THE INVENTION

In one aspect, the present invention provides a compound of general Formula I:

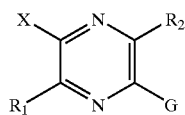

Formula I or a stereoisomer thereof, a pharmaceutically acceptable salt thereof, or a prodrug thereof, wherein in Formula I:

$R_1$ and $R_2$ are independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S(O)$_m$R$_a$, —NR$_a$C(O)OR$_a$, —NR$_a$C(S)OR$_a$, —OC(O)NR$_a$R$_a$, —OC(S)NR$_a$R$_a$, —NR$_a$C(O)NR$_a$R$_a$, —NR$_a$C(S)NR$_a$R$_a$, —C(O)OR$_a$, —C(S)OR$_a$, —OC(O)OR$_a$, or —CR$_a$R$_a$Ar;

X is selected from —NR$_3$R$_4$, —OR$_3$, —CR$_3$R$_4$R$_5$, —C(O)R$_3$, —C(S)R$_3$, —S(O)$_m$R$_3$, —NR$_3$C(O)R$_4$, —NR$_3$C(S)R$_4$, —NR$_3$S(O)$_m$R$_4$, or —R$_3$;

$R_3$, $R_4$, and $R_5$ are independently selected from R$_a$, substituted alkyl, substituted aryl, substituted heteroaryl, substituted cycloalkyl, substituted heterocycloalkyl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl;

$R_a$ each is selected from H, alkyl, cycloalkyl, haloalkyl, aryl, heteroaryl, or heterocycloalkyl, where each instance of R$_a$ may be optionally substituted with 1 to 5 of R$_t$, —OR$_t$, —S(O)$_m$R$_t$, —NR$_t$R$_t$, oxo (=O), thione (=S);

$R_t$ each is selected from H, halogen, —NO$_2$, —NH$_2$, —OH, —SH, —CN, —C(O)NH$_2$, —C(S)NH$_2$, —C(O)NHalkyl, —C(S)NHalkyl, —C(O)Nalkylalkyl, —C(S)Nalkylalkyl, —Oalkyl, —NHalkyl, —Nalkylalkyl, —S(O)$_m$alkyl, —SO$_2$NH$_2$, —SO$_2$NHalkyl and —SO$_2$Nalkylalkyl, alkyl, cycloalkyl, haloalkyl, phenyl, benzyl, heteroaryl, or heterocycloalkyl where phenyl, benzyl, heteroaryl, and heterocycloalkyl may be optionally substituted with alkyl or halogen;

G is selected from

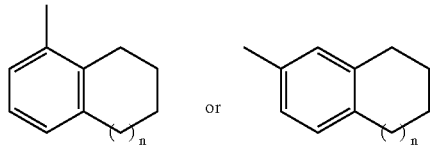

wherein each G group may have from 1 to 6 substituents independently selected from halogen, —CN, —NO$_2$, oxo (=O), thione (=S), —OR$_5$, —SR$_5$, —NR$_5$R$_5$, —C(O)R$_5$, —C(S)R$_5$, —C(O)OR$_5$, —C(S)OR$_5$, —C(O)NR$_5$R$_5$, —C(S)NR$_5$R$_5$, —S(O)$_m$R$_5$, —S(O)$_2$NR$_5$R$_5$, —NR$_5$C(O)R$_5$, —NR$_5$C(S)R$_5$, —NR$_5$C(O)OR$_5$, —NR$_5$C(S)OR$_5$, —NR$_5$C(O)NR$_5$R$_5$, —NR$_5$C(S)NR$_5$R$_5$, —NR$_5$S(O)$_2$R$_5$, —OC(O)R$_5$, —OC(S)R$_5$, —OC(O)OR$_5$, —OC(S)OR$_5$, —OC(O)NR$_5$R$_5$, —OC(S)NR$_5$R$_5$, —CR$_5$R$_5$Ar, alkyl, substituted alkyl, cycloalkyl, substituted cycloalkyl, aryl, substituted aryl, heteroaryl, substituted heteroaryl, heterocycloalkyl, or substituted heterocylcloalkyl, and wherein each G group may contain up to one double bond in its non-aromatic ring;

Ar is selected from aryl, substituted aryl, heteroaryl and substituted heteroaryl;

m is 0, 1 or 2; and n is 0, 1, or 2.

In another aspect, the present invention provides a pharmaceutical composition comprising a compound of Formula I, a stereoisomer thereof, a pharmaceutically acceptable salt thereof, or a prodrug thereof, or a pharmaceutically acceptable salt of the prodrug thereof. The compositions can be prepared in any suitable forms such as tablets, pills, powders, lozenges, sachets, cachets, elixirs, suspensions, emulsions, solutions, syrups, aerosols, and ointments.

The compounds of the inventions are CRF$_1$ receptor antagonists and are useful for treating disorders or conditions associated with CRF or CRF$_1$ receptors, including human CRF$_1$ receptors.

Thus, in another aspect, the present invention provides a method of antagonizing CRF$_1$ receptors in a warm-blooded animal, comprising administering to the animal a compound of the invention at amount effective to antagonize CRF$_1$ receptors.

In still another aspect, the present invention provides a method for screening for ligands for CRF$_1$ receptors, which method comprises: a) carrying out a competitive binding assay with CRF$_1$ receptors, a compound of Formula I which is labeled with a detectable label, and a candidate ligand; and b) determining the ability of said candidate ligand to displace said labeled compound.

In still another aspect, the present invention provides a method for detecting CRF$_1$ receptors in a tissue comprising: a) contacting a compound of Formula I, which is labeled with a detectable label, with a tissue, under conditions that permit binding of the compound to the tissue; and b) detecting the labeled compound bound to the tissue.

In yet another aspect, the present invention provides a method of inhibiting the binding of CRF to $CRF_1$ receptors in vitro, comprising contacting a compound of the invention with a solution comprising cells expressing the $CRF_1$ receptor, such as . IMR32 cells, wherein the compound is present in the solution at a concentration sufficient to inhibit the binding of CRF to the $CRF_1$ receptor.

Compounds of the invention are useful for treating, in a warm-blooded animal, particularly a mammal, and more particularly a human, various disorders that are associated with CRF or $CRF_1$ receptors, or disorders the treatment of which can be effected or facilitated by antagonizing $CRF_1$ receptors. Examples of such disorders include anxiety-related disorders (such as anxiety, generalized anxiety disorder, social anxiety disorder, anxiety with co-morbid depressive illness, panic disorder, and obsessive-compulsive disorder); mood disorders (such as depression, including major depression, single episode depression, recurrent depression, child abuse induced depression, and postpartum depression, and affective disorder); post-traumatic stress disorder; supranuclear palsy; immune suppression; drug or alcohol withdrawal symptoms; substance abuse disorder (e.g., nicotine, cocaine, ethanol, opiates, or other drugs); inflammatory disorders (such as rheumatoid arthritis and osteoarthritis); fertility problems including infertility; pain; asthma; psoriasis and allergies; phobias; sleep disorders induced by stress; pain perception (such as fibromyalgia); dysthemia; bipolar disorders; cyclothymia; fatigue syndrome; stress-induced headache; cancer; human immunodeficiency virus (HIV) infections; neurodegenerative diseases (such as Alzheimer's disease, Parkinson's disease and Huntington's disease); gastrointestinal diseases (such as ulcers, irritable bowel syndrome, Crohn's disease, spastic colon, diarrhea, and post operative ilius and colonic hypersensitivity associated by psychopathological disturbances or stress); eating disorders (such as anorexia and bulimia nervosa and other feeding disorders); hemorrhagic stress; stress-induced psychotic episodes; euthyroid sick syndrome; syndrome of inappropriate antidiarrhetic hormone (ADH); obesity; head traumas; spinal cord trauma; ischemic neuronal damage (e.g., cerebral ischemia such as cerebral hippocampal ischemia); excitotoxic neuronal damage; epilepsy; cardiovascular and heart related disorders (such as hypertension, tachycardia and congestive heart failure); stroke; immune dysfunctions including stress induced immune dysfunctions (e.g., stress induced fevers, porcine stress syndrome, bovine shipping fever, equine paroxysmal fibrillation, and dysfunctions induced by confinement in chickens, sheering stress in sheep or human-animal interaction related stress in dogs); muscular spasms; urinary incontinence; senile dementia of the Alzheimer's type; multiinfarct dementia; amyotrophic lateral sclerosis; chemical dependencies and addictions (e.g., dependences on alcohol, cocaine, heroin, benzodiazepines, or other drugs); osteoporosis; psychosocial dwarfism, hypoglycemia, and skin disorders (such as acne, psoriasis, chronic contact demertitis, and stress-exacerbated skin disorders). They are also useful for promoting smoking cessation and hair growth, or treating hair loss.

Thus, in yet a further aspect the present invention provides a method of treating a disorder, in warm-blooded animal, the treatment of which disorder can be effected or facilitated by antagonizing $CRF_1$ receptors, which method comprises administration to a patient in need thereof an effective amount of a compound of Formula I. In a particular embodiment the invention provides a method for the treatment of disorders that manifest hypersecretion of CRF. Examples of disorders that can be treated with the compounds of the invention include generalized anxiety disorder; social anxiety disorder; anxiety; obsessive-compulsive disorder; anxiety with co-morbid depressive illness; panic disorder; and mood disorders such as depression, including major depression, single episode depression, recurrent depression, child abuse induced depression, postpartum depression, hair loss, and contact demertitis. It is preferred that the warm-blooded animal is a mammal, and more preferred that the animal is a human.

DETAILED DESCRIPTION OF THE INVENTION

In the first aspect, the invention provides a compound of Formula I as described above.

Examples of particular compounds of the invention include:

compounds of Formula I where $R_1$ and $R_2$ are halogen, —$NO_2$, —CN, —$R_a$, —$OR_a$, —$S(O)_mR_a$, or —$NR_aR_a$;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, —$OR_3$, —$C(O)R_3$, or $R_3$;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, —$OR_3$, —$C(O)R_3$, or $R_3$ and G is 2,3-dihydro-1H-inden-5-yl or 5,6,7,8-tetrahydronaphthalen-2-yl, either optionally substituted as described;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, and G is 2,3-dihydro-1H-inden-5-yl or 5,6,7,8-tetrahydronaphthalen-2-yl, either optionally substituted as described;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, and G is 4- or 6-substituted 2,3-dihydro-1H-inden-5-yl or 1- or 3-substituted 5,6,7,8-tetrahydronaphthalen-2-yl, either additionally optionally substituted as described;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, and G is 6-substituted 2,3-dihydro-1H-inden-5-yl or 3-substituted 5,6,7,8-tetrahydronaphthalen-2-yl, either additionally optionally substituted as described; and compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, and G is 6-substituted 2,3-dihydro-1H-inden-5-yl additionally optionally substituted as described;

compounds of Formula I where the G group has at least 1 and up to 6 substituents and wherein one said substituent is either oxo (C=O) or thione (C=S) and is located on the non-aromatic ring;

compounds of Formula I where $R_1$ and $R_2$ are independently selected from halogen, —$NO_2$, —CN, —$R_a$, —$OR_a$, —$S(O)_mR_a$, or —$NR_aR_a$ and X is selected from —$NR_3R_4$, —$OR_3$, —$C(O)R_3$, or $R_3$, and where the G group has at least 1 and up to 6 substituents and wherein one said substituent is either oxo (C=O) or thione (C=S) and is located on the non-aromatic ring;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, —$OR_3$, —$C(O)R_3$, or $R_3$ and G is 2,3-dihydro-1H-inden-5-yl or 5,6,7,8-tetrahydronaphthalen-2-yl, and where the G group has at least 1 and up to 6 substituents and wherein one said substituent is either oxo (C=O) or thione (C=S) and is located on the non-aromatic ring, and where G can be further optionally substituted as described;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, and G is 2,3-dihydro-1H-inden-5-yl or 5,6,7,8-tetrahydronaphthalen-2-yl, and where the G group has at least 1 and up to 6 substituents and wherein one said substituent is either oxo (C=O) or thione (C=S) and is located on the non-aromatic ring, and where G can be further optionally substituted as described;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, and G is 4- or 6-substituted 2,3-dihydro-1H-inden-5-yl or 1- or 3-substituted 5,6,7,8-tetrahydronaphthalen-2-yl, and where the G group has at least 2 and up to 6 substituents and wherein one said substituent is either oxo (C=O) or thione (C=S) and is located on the non-aromatic ring, and where G can be further optionally substituted as described;

compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, and G is 6-substituted 2,3-dihydro-1H-inden-5-yl or 3-substituted 5,6,7,8-tetrahydronaphthalen-2-yl, and where the G group has at least 2 and up to 6 substituents and wherein one said substituent is either oxo (C=O) or thione (C=S) and is located on the non-aromatic ring, and where G can be further optionally substituted as described; and compounds of Formula I where $R_1$ and $R_2$ are halogen, —$NO_2$, —CN, —$R_a$, —$OR_a$, —$S(O)_mR_a$, or —$NR_aR_a$ and X is —$NR_3R_4$, and G is 6-substituted 2,3-dihydro-1H-inden-5-yl, and where the G group has at least 2 and up to 6 substituents and wherein one said substituent is either oxo (C=O) or thione (C=S) and is located on the non-aromatic ring, and where G can be further optionally substituted as described.

Following are examples of particular compounds of the invention, with each compound being identified both by a chemical name and a structural formula immediately below the chemical name:

3,6-diethyl-N-(1-ethylpropyl)-5-(6-methoxy-2,3-dihydrro-1H-inden-5-yl)pyrazin-2-amine;

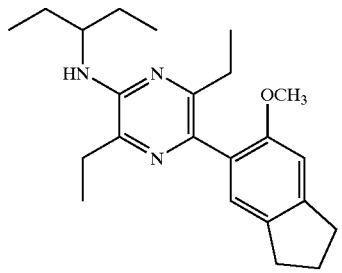

3,6-diethyl-N-(1-ethylpropyl)-5-(3-methoxy-5,6,7,8-tetrahydronaphthalen-2-yl)pyrazin-2-amine;

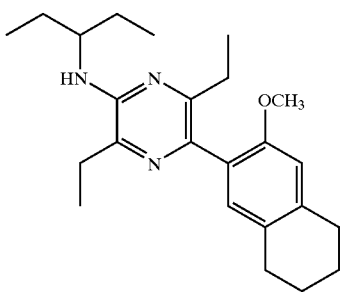

3,6-diethyl-N-(1-ethylpropyl)-5-(4-methoxy-7-methyl-2,3-dihydro-1H-inden-5-yl)pyrazin-2-amine;

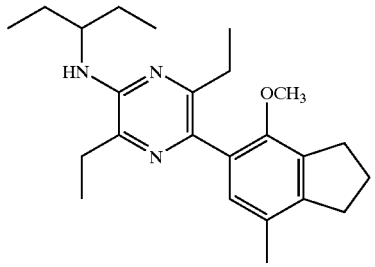

3,6-diethyl-N-(1-ethylpropyl)-5-(2-methoxy-5,6,7,8-tetrahydronaphthalen-1-yl)pyrazin-2-amine;

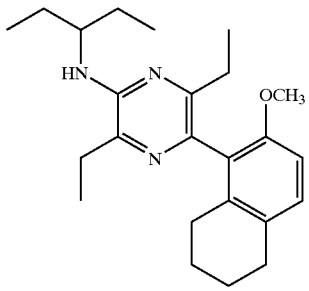

3,6-diethyl-N-(1-ethylpropyl)-5-(4-methoxy-5,6,7,8-tetrahydronaphthalen-1-yl)pyrazin-2-amine;

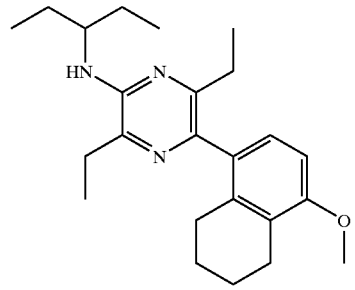

5-(2-ethoxy-5,6,7,8-tetrahydronaphthalen-1-yl)-3,6-diethyl-N-(1-ethylpropyl)pyrazin-2amine;

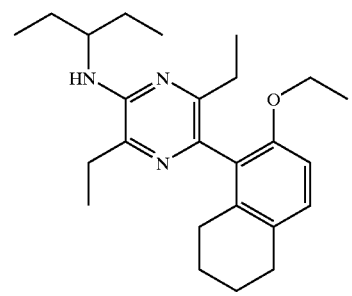

3-{3,6-diethyl-5-[(1-ethylpropyl)amino]pyrazin-2-yl}-5,6,7,8-tetrahydronaphthalen-2-ol;

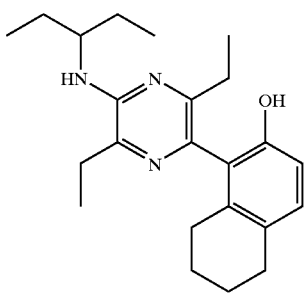

3,6-diethyl-5-(6-methoxy-2,3-dihydro-1H-inden-5-yl)-N-[2-methoxy-1-(methoxymethyl)ethyl]-pyrazin-2-amine;

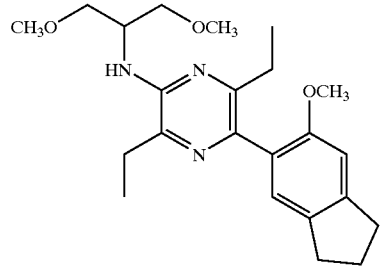

3-{3,6-diethyl-5-[(1-ethylpropyl)amino]pyrazin-2-yl}-5,6,7,8-tetrahydronaphthalen-2-trifluoromethanesulfonate;

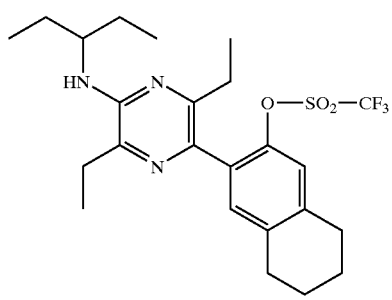

3,6-diethyl-5-(6-methoxy-2,3-dihydro-1H-inden-5-yl)-N-[(1R)-1-(methoxymethyl)propyl]pyrazin-2-amine;

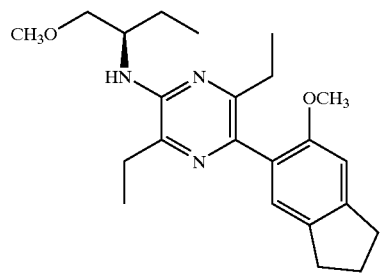

3,6-diethyl-N-(1-ethylpropyl)-5-(5,6,7,8-tetrahydronaphthalen-2-yl)pyrazin-2-amine;

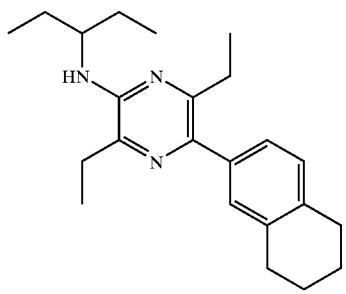

N-[(1S)-1-(ethoxymethyl)propyl]-3,6-diethyl-5-(6-methoxy-2,3-dihydro-1H-inden-5-yl)pyrazin-2-amine;

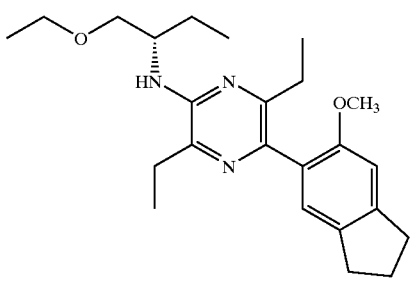

5-(3-chloro-5,6,7,8-tetrahydronaphthalen-2-yl)-3,6-diethyl-N-(1-ethylpropyl)pyrazin-2-amine;

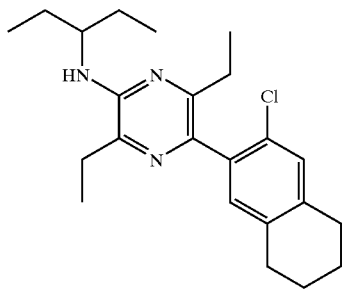

3,6-diethyl-N-{(1S)-1-[(2-fluoroethoxy)methyl]propyl}-5-(6-methoxy-2,3-dihydro-1H-inden-5-yl)pyrazin-2-amine;

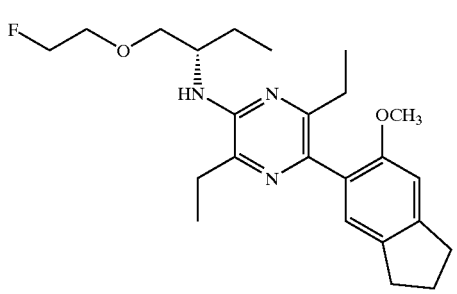

3,6-diethyl-5-(6-methoxy-2,3-dihydro-1H-inden-5-yl)-N-[(1R)-1-phenylethyl]pyrazin-2-amine;

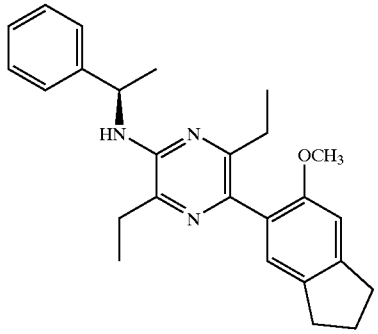

3,6-diethyl-5-(6-methoxy-2,3-dihydro-1H-inden-5-yl)-N-[(1S)-1-phenylethyl]pyrazin-2-amine;

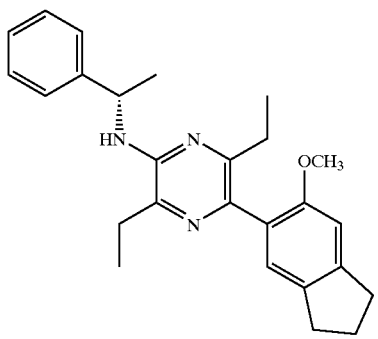

3,6-diethyl-5-(6-methoxy-2,3-dihydro-1H-inden-5-yl)-N-[(1R)-1-methylpropyl]pyrazin-2-amine;

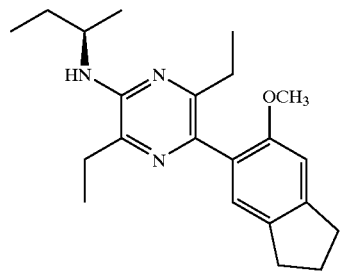

3,6-diethyl-5-(6-methoxy-2,3-dihydro-1H-inden-5-yl)-N-[(1S)-1-methylpropyl]pyrazin-2-amine;

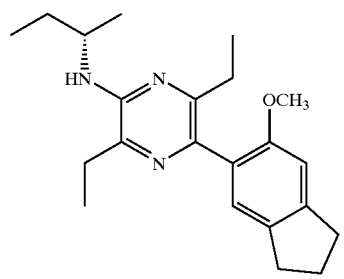

N-cyclopentyl-3,6-diethyl-5-(6-methoxy-2,3-dihydro-1H-inden-5-yl)pyrazin-2-amine;

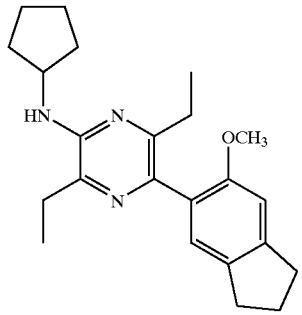

N-(dicyclopropylmethyl)-3,6-diethyl-5-(6-methoxy-2,3-dihydro-1H-inden-5-yl)pyrazin-2-amine;

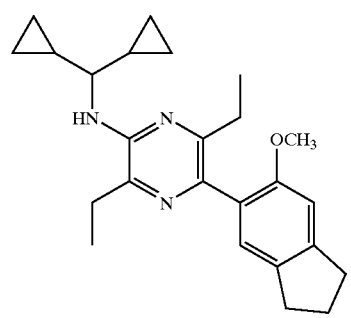

3,6-diethyl-5-(6-methoxy-2,3-dihydro-1H-inden-5-yl)-N-(1-methylbutyl)pyrazin-2-amine;

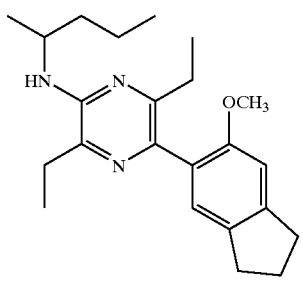

(1R,2S)-1-{[3,6-diethyl-5-(3-methoxy-5,6,7,8-tetrahydronaphthalen-2-yl)pyrazin-2-yl]amino}-2,3-dihydro-1H-inden-2-ol;

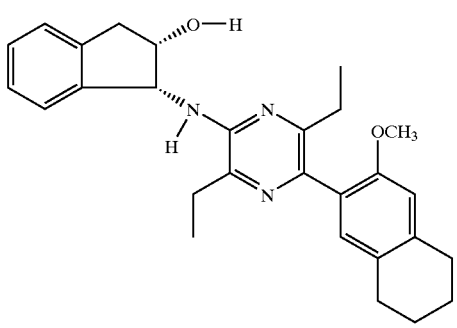

3,6-diethyl-N-[(1R,2S)-2-(2-fluoroethoxy)-2,3-dihydro-1H-
   inden-1-yl]-5-(3-methoxy-5,6,7,8-tetrahydronaphthalen-
   2-yl)pyrazin-2-amine;

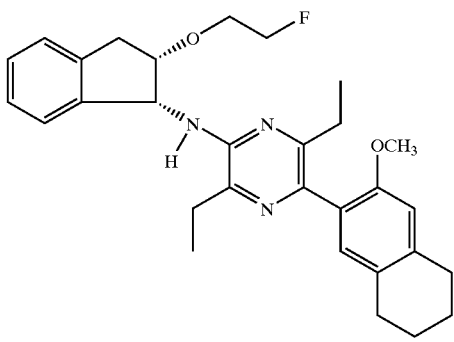

3,6-diethyl-N-[2-methoxy-1-(methoxymethyl)ethyl]-5-(3-
   methoxy-5,6,7,8-tetrahydronaphthalen-2-yl)pyrazin-2-
   amine;

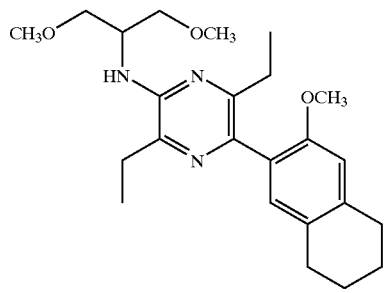

3,6-diethyl-N-[(1R)-1-(methoxymethyl)propyl]-5-(3-
   methoxy-5,6,7,8-tetrahydronaphthalen-2-yl)pyrazin2-
   amine;

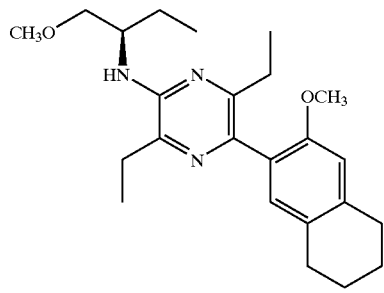

3,6-diethyl-N-[(1S)-1-(methoxymethyl)propyl]-5-(3-
   methoxy-5,6,7,8-tetrahydronaphthalen-2-yl)pyrazin2-
   amine;

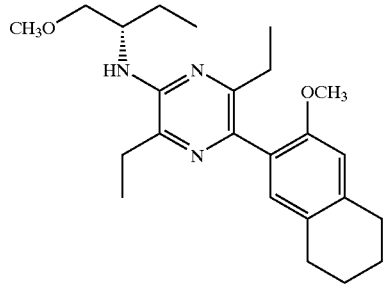

N-[(1S)-1-(ethoxymethyl)propyl]-3,6-diethyl-5-(3-
   methoxy-5,6,7,8-tetrahydronaphthalen-2-yl)pyrazin-2-
   amine;

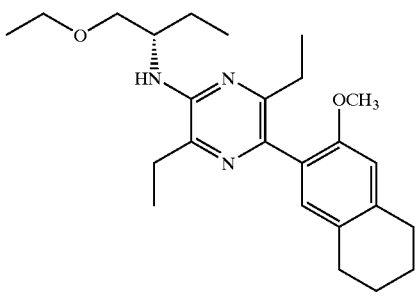

3,6-diethyl-N-{(1S)-1-[(2-fluoroethoxy)methyl]propyl}-5-
   (3-methoxy-5,6,7,8-tetrahydronaphthalen-2-yl)pyrazin-
   2-amine;

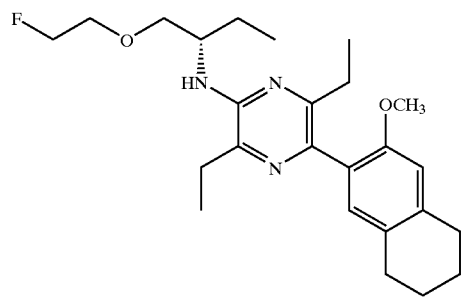

3,6-diethyl-5-(3-methoxy-5,6,7,8-tetrahydronaphthalen-2-
   yl)-N-[(1R)-1-phenylethyl]pyrazin-2-amine;

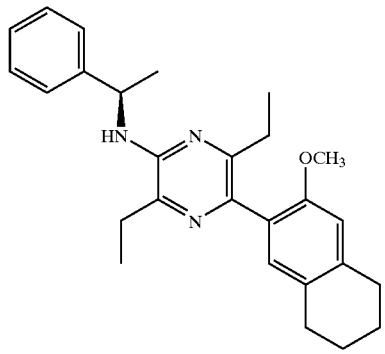

3,6-diethyl-5-(3-methoxy-5,6,7,8-tetrahydronaphthalen-2-
   yl)-N-[(1S)-1-phenylethyl]pyrazin-2-amine;

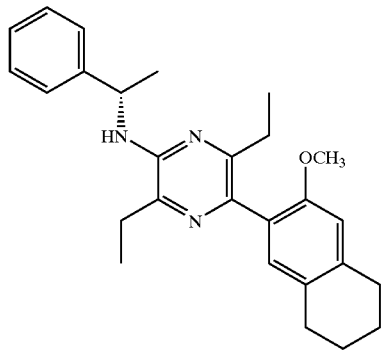

3,6-diethyl-5-(3-methoxy-5,6,7,8-tetrahydronaphthalen-2-yl)-N-[(1R)-1-methylpropyl]pyrazin-2amine;

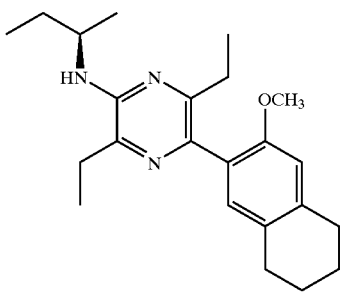

3,6-diethyl-5-(3-methoxy-5,6,7,8-tetrahydronaphthalen-2-yl)-N-[(1S)-1-methylpropyl]pyrazin-2-amine;

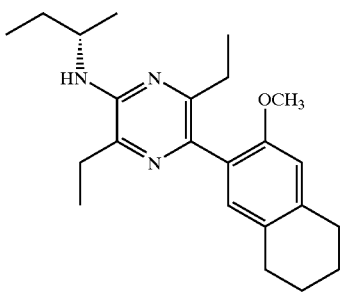

3,6-diethyl-N-(2-ethylbutyl)-5-(3-methoxy-5,6,7,8-tetrahydronaphthalen-2-yl)pyrazin-2-amine;

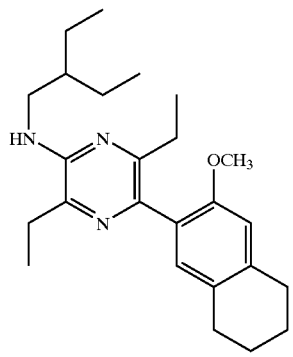

N-(dicyclopropylmethyl)-3,6-diethyl-5-(3-methoxy-5,6,7,8-tetrahydronaphthalen-2-yl)pyrazin-2-amine;

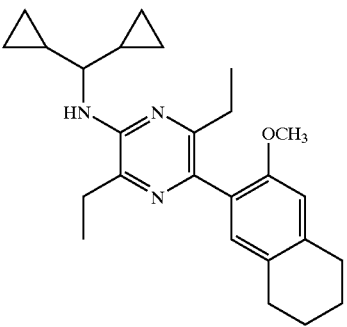

N-cyclopentyl-3,6-diethyl-5-(3-methoxy-5,6,7,8-tetrahydronaphthalen-2-yl)pyrazin-2-amine;

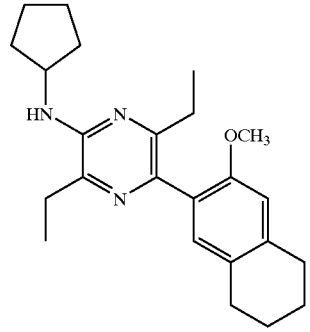

3,6-diethyl-5-(3-methoxy-5,6,7,8-tetrahydronaphthalen-2-yl)-N-(1-propylbutyl)pyrazin-2-amine;

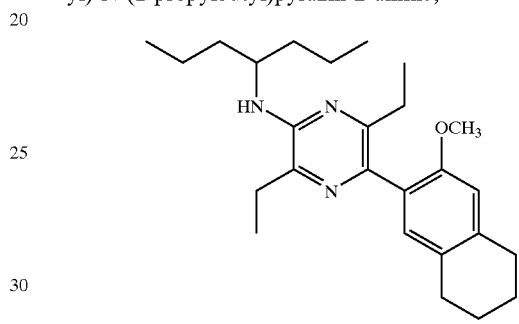

3,6-diethyl-5-(3-methoxy-5,6,7,8-tetrahydronaphthalen-2-yl)-N-(1-methylbutyl)pyrazin-2-amine;

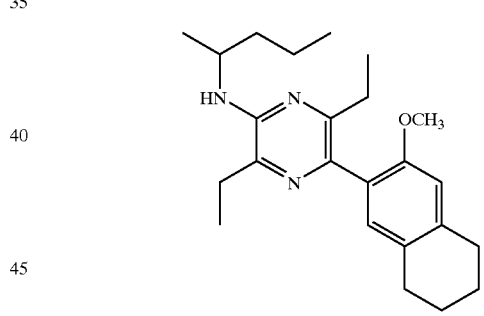

ethyl 3-{[3,6-diethyl-5-(3-methoxy-5,6,7,8-tetrahydronaphthalen-2-yl)pyrazin-2-yl]amino}butanoate;

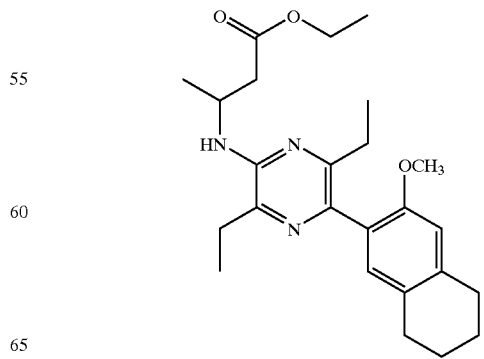

3-{[3,6-diethyl-5-(3-methoxy-5,6,7,8-tetrahydronaphthalen-2-yl)pyrazin-2-yl]amino}butan-1ol;

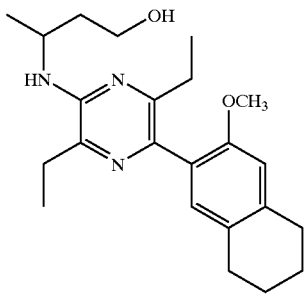

3,6-diethyl-N-(3-methoxy-1-methylpropyl)-5-(3-methoxy-5,6,7,8-tetrahydronaphthalen-2-yl)pyrazin-2-amine;

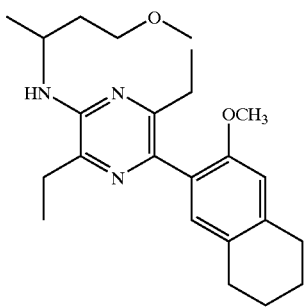

N-(3-ethoxy-1-methylpropyl)-3,6-diethyl-5-(3-methoxy-5,6,7,8-tetrahydronaphthalen-2-yl)pyrazin-2-amine;

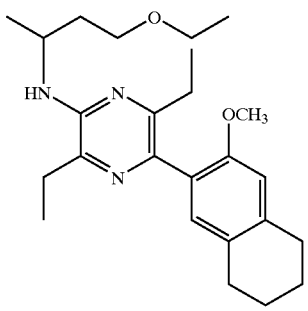

3-{[3,6-diethyl-5-(3-methoxy-5,6,7,8-tetrahydronaphthalen-2-yl)pyrazin-2-yl]amino}butyl acetate;

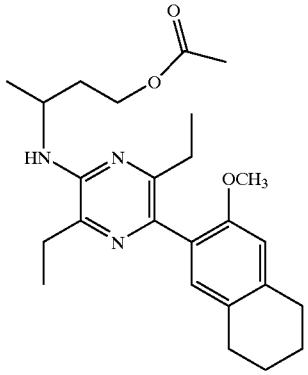

Methyl (3R,4S)-3-{[3,6-diethyl-5-(6-methoxy-2,3-dihydro-1H-inden-5-yl)pyrazin-2-yl]amino}-4-ethoxypyrrolidine-1-carboxylate;

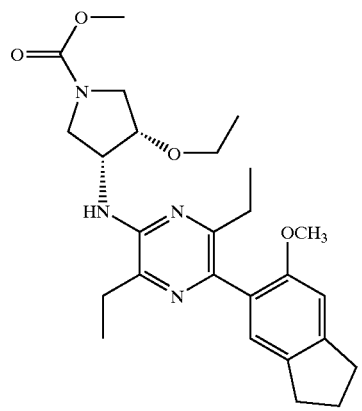

Methyl (3R,4S)-3-{[3,6-diethyl-5-(3-methoxy-5,6,7,8-tetrahydronaphthalen-2-yl]amino}-4-ethoxypyrrolidine-1-carboxylate;

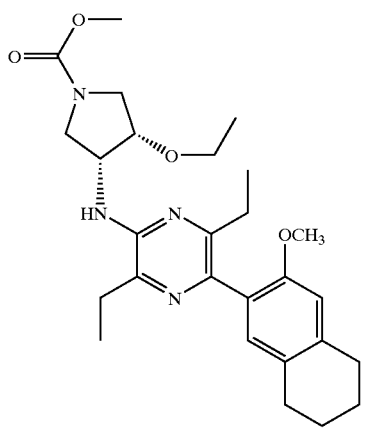

5-{3,6-diethyl-5-[(1-ethylpropyl)amino]pyrazin-2-yl}-6-methoxyindan-1-one;

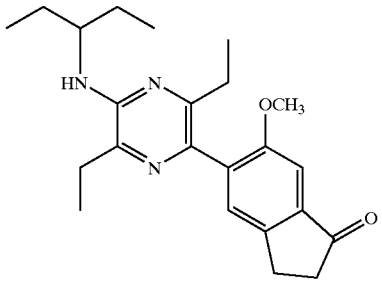

3,6-diethyl-N-(1-ethylpropyl)-5-(6-ethynyl-2,3-dihydro-1H-inden-5-yl)pyrazin-2-amine;

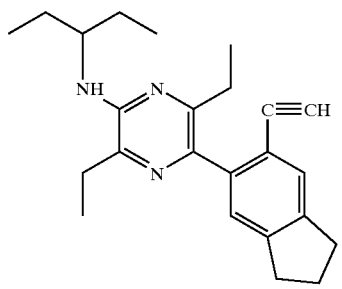

5-{3,6-diethyl-5-[(1-ethylpropyl)amino]pyrazin-2-yl}-2-hydroxy-6-methoxy-2-methylindan-1-one;

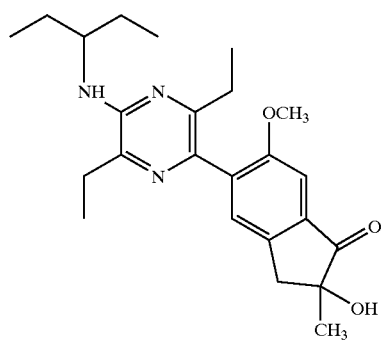

N-[3,6-diethyl-5-(6-methoxy-2,3-dihydro-1H-inden-5-yl)pyrazin-2-yl]pyrimidin-2-amine;

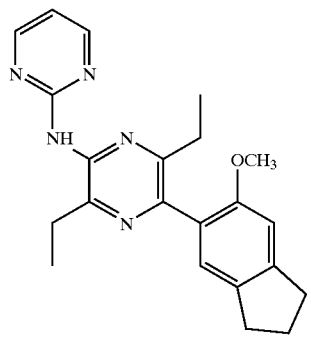

N-[(2S,4R)-2-ethoxy-4-phenylcyclopentyl]-3,6-diethyl-5-(6-methoxy-2,3-dihydro-1H-inden-5-yl)pyrazin-2-amine;

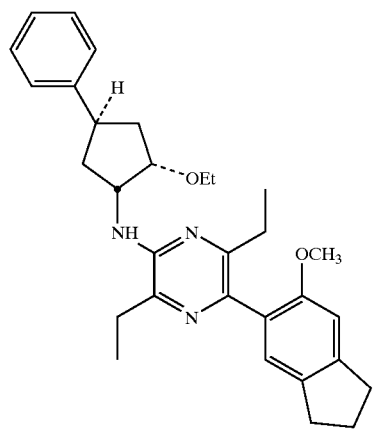

3,6-diethyl-5-(6-methoxy-2,3-dihydro-1H-inden-5-yl)-N-[(2R,4R)-4-methoxy-2-(methoxymethyl)cyclopentyl]pyrazin-2-amine;

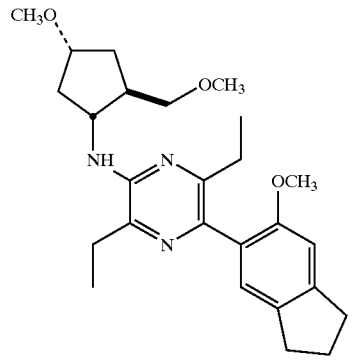

2,5-diethyl-3-(1-ethylpropoxy)-6-(6-methoxy-2,3-dihydro-1H-inden-5-yl)pyrazine;

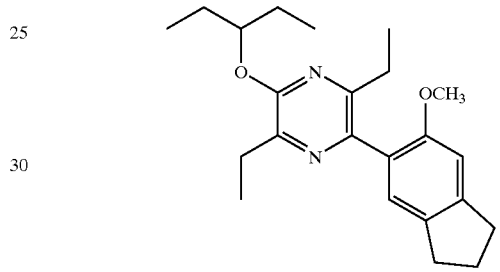

3,6-diethyl-N-(1-ethylpropyl)-5-(4-methoxy-2,3-dihydro-1H-inden-5-yl)pyrazin-2-amine;

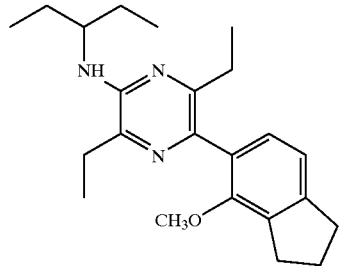

3,6-diethyl-N-(1-ethylpropyl)-5-(6-methoxy-4-methyl-2,3-dihydro-1H-inden-5-yl)pyrazin-2-amine;

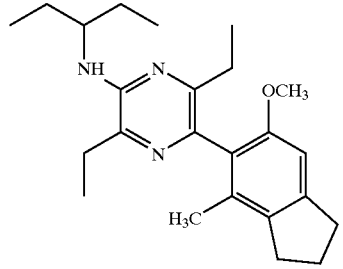

3,6-diethyl-N-(1-ethylpropyl)-5-(5-methoxy-1H-inden-6-yl)pyrazin-2-amine;

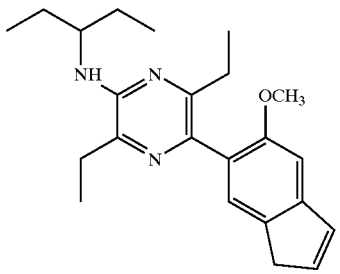

3,6-diethyl-N-(1-ethylpropyl)-5-(3-methoxy-5,6-dihydronaphthalen-2-yl)pyrazin-2-amine;

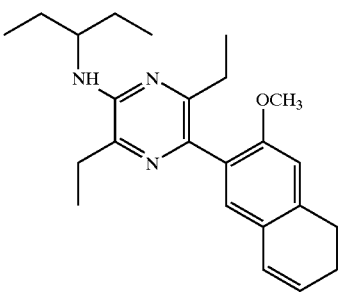

3,6-diethyl-5-(6-methoxy-2,3-dihydro-1H-inden-5-yl)-N-{1-[(2S)-2-(methylamino)cyclopropyl]propyl}pyrazin-2-amine;

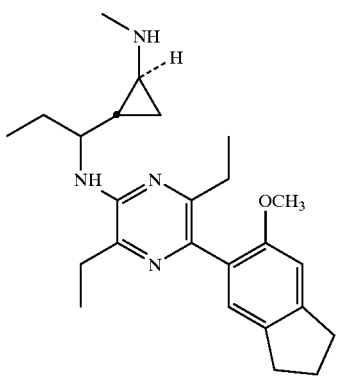

6-{3,6-diethyl-5-[(1-ethylpropyl)amino]pyrazin-2-yl}indane-5-carbonitrile;

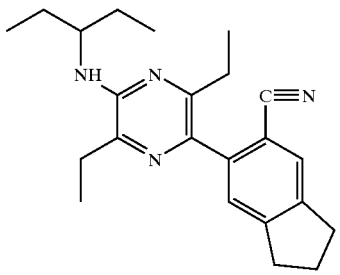

6-{3,6-diethyl-5-[(1-ethylpropyl)amino]pyrazin-2-yl}-5-methoxyindan-1-one;

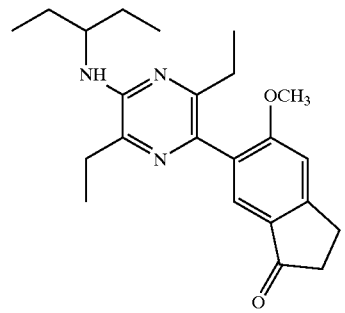

6-{3,6-diethyl-5-[(1-ethylpropyl)amino]pyrazin-2-yl}-7-methoxy-3,4-dihydronaphthalen-1(2H)-one;

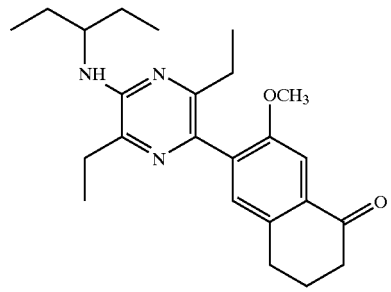

5-{3,6-diethyl-5-[(1-ethylpropyl)amino]pyrazin-2-yl}-6-methoxyindan-1-ol;

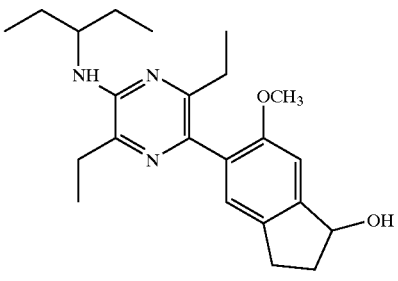

5-(1-amino-6-methoxy-2,3-dihydro-1H-inden-5-yl)-3,6-diethyl-N-(1-ethylpropyl)pyrazin-2-amine;

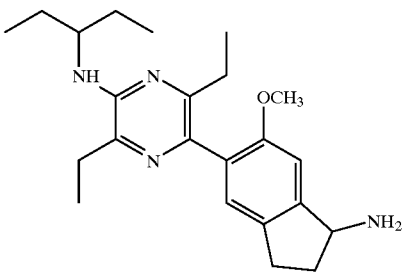

2,5-diethyl-3-(6-methoxy-2,3-dihydro-1H-inden-5-yl)-6-pyrrolidin-1-ylpyrazine;

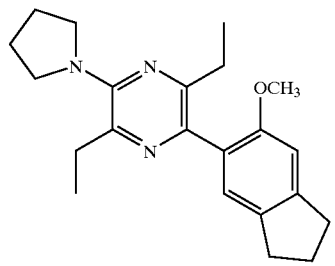

3,6-diethyl-N-(1-ethylpropyl)-5-[6-methoxy-1-(methylamino)-2,3-dihydro-1H-inden-5-yl]pyrazin-2-amine;

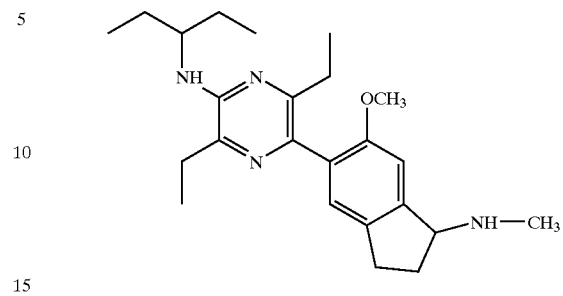

3,6-diethyl-N-(1-ethylpropyl)-5-(6-methyl-2,3-dihydro-1H-inden-5-yl)pyrazin-2-amine;

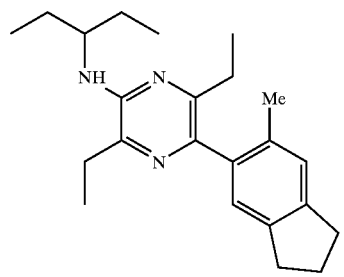

N-(5-{3,6-diethyl-5-[(1-ethylpropyl)amino]pyrazin-2-yl}-6-methoxy-2,3-dihydro-1H-inden-1-yl)acetamide;

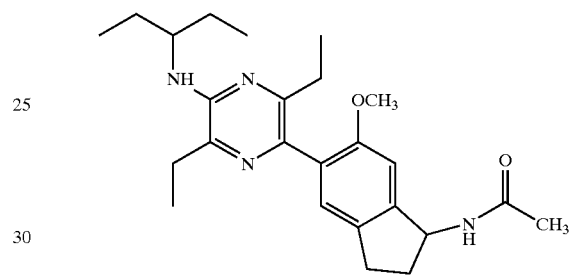

N-(1-ethylpropyl)-5-(6-methoxy-2,3-dihydro-1H-inden-5-yl)-3,6-dimethylpyrazin-2-amine;

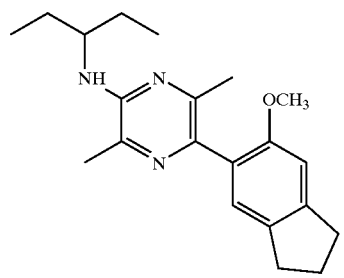

5-(1,6-dimethoxy-2,3-dihydro-1H-inden-5-yl)-3,6-diethyl-N-(1-ethylpropyl)pyrazin-2-amine;

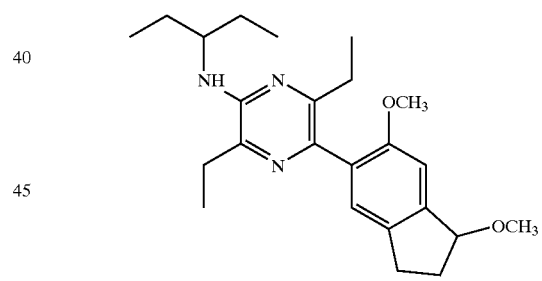

(1E)-5-{3,6-diethyl-5-[(1-ethylpropyl)amino]pyrazin-2-yl}-6-methoxyindan-1-one oxime;

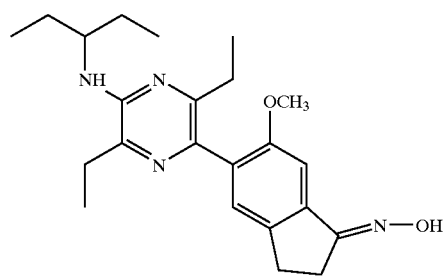

5-{3,6-diethyl-5-[(1-ethylpropyl)amino]pyrazin-2-yl}-6-methoxy-2,3-dihydro-1H-inden-1-yl acetate;

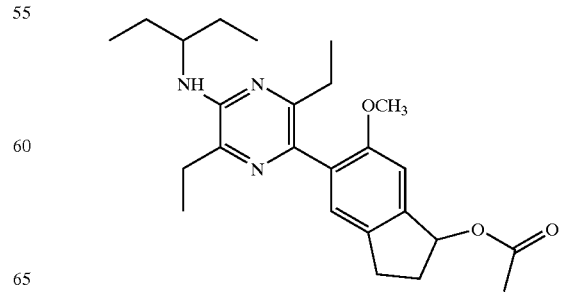

N-(5-{3,6-diethyl-5-[(1-ethylpropyl)amino]pyrazin-2-yl}-6-methoxy-2,3-dihydro-1H-inden-1-yl)urea;

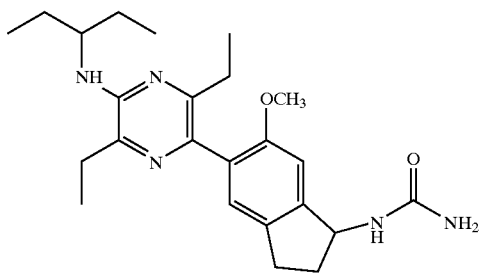

N-(5-{3,6-diethyl-5-[(1-ethylpropyl)amino]pyrazin-2-yl}-6-methoxy-2,3-dihydro-1H-inden1-yl)ethanethioamide;

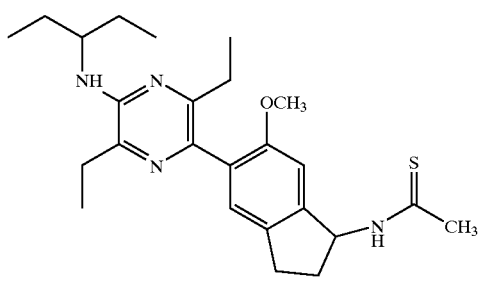

5-{3,6-diethyl-5-[(1-ethylpropyl)amino]pyrazin-2-yl}-6-fluoroindan-1-one;

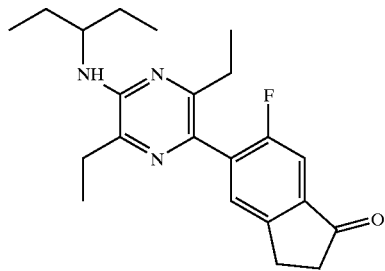

5-{3,6-diethyl-5-[(1-ethylpropyl)amino]pyrazin-2-yl}-6-methoxy-1-methylindan-1-ol;

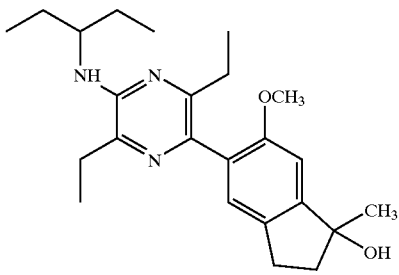

5-{3,6-diethyl-5-[(1-ethylpropyl)amino]pyrazin-2-yl}-6-methoxy-1H-inden-1-one;

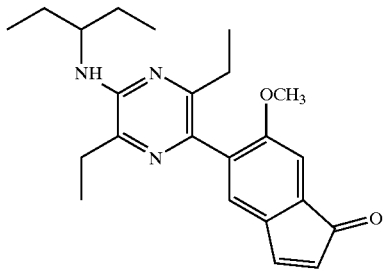

5-{3,6-diethyl-5-[(1-ethylpropyl)amino]pyrazin-2-yl}-6-methoxy-1,3-dihydro-2H-inden-2-one;

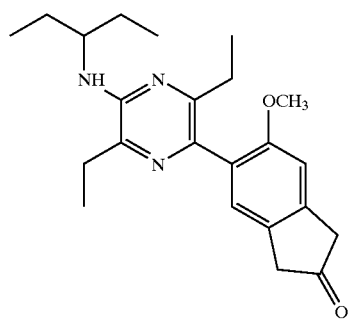

5-{3,6-diethyl-5-[(1-ethylpropyl)amino]pyrazin-2-yl}-6-methoxy-1H-indene-1,3(2H)-dione;

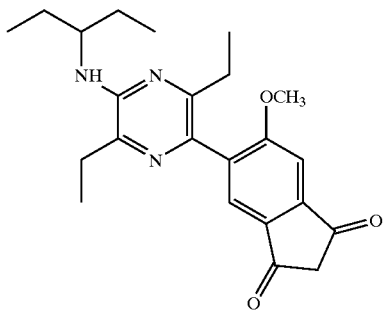

2,5-diethyl-3-(6-methoxy-2,3-dihydro-1H-inden-5-yl)-6-[(2S,4R)-4-methoxy-2-(methoxymethyl)pyrrolidin-1-yl]pyrazine;

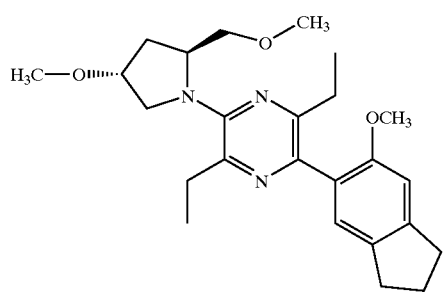

5-{3,6-diethyl-5-[(1-ethylpropyl)amino]pyrazin-2-yl}-6-methoxyindane-1-thione

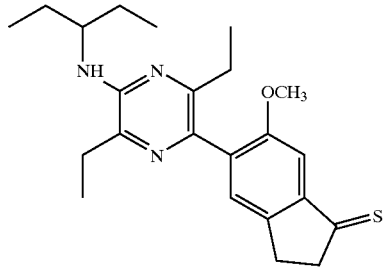

5-{6-ethyl-5-[(1-ethylpropyl)amino]-3-methylpyrazin-2-yl}-6-methoxyindan-1-one;

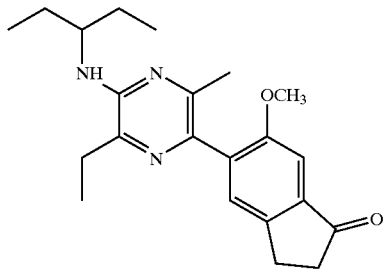

5-[3-ethyl-5-[(1-ethylpropyl)amino]-6-(methoxymethyl)pyrazin-2-yl]-6-methoxyindane-1-thione;

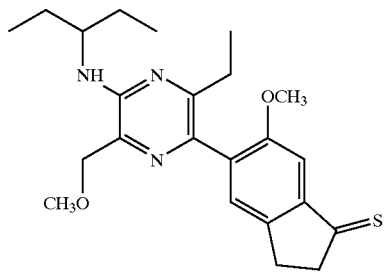

5-[6-ethyl-5-[(1-ethylpropyl)amino]-3-(methoxymethyl)pyrazin-2-yl]-6-methoxyindane-1-thione;

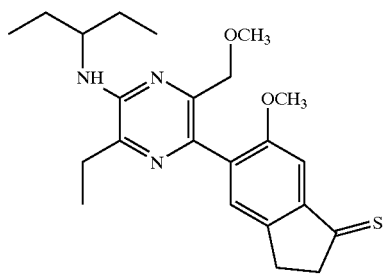

1-[(5-{3,6-diethyl-5-[(1-ethylpropyl)amino]pyrazin-2-yl}-6-methoxy-2,3-dihydro-1H-inden1-yl)oxy]acetone;

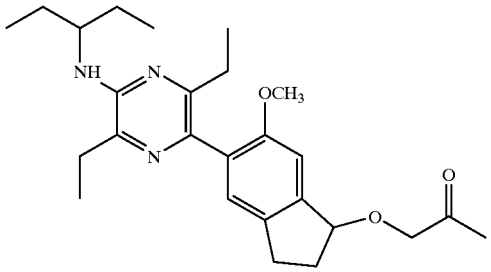

1-[(5-{3,6-diethyl-5-[(1-ethylpropyl)amino]pyrazin-2-yl}-6-methoxy-2,3-dihydro-1H-inden-1-yl)oxy]acetone;

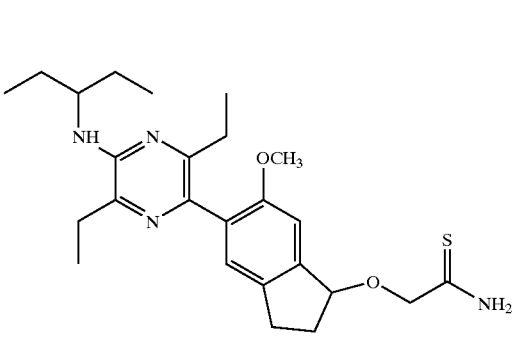

2-[(5-{3,6-diethyl-5-[(1-ethylpropyl)amino]pyrazin-2-yl}-6-methoxy-2,3-dihydro-1H-inden-1-yl)oxy]ethanethioamide;

3,6-diethyl-5-(6-methoxy-2,3-dihydro-1H-inden-5-yl)-N-(1-phenylpropyl)pyrazin-2-amine;

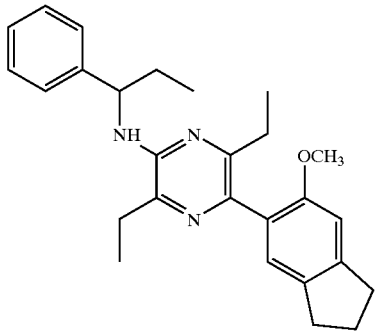

5-{3,6-diethyl-5-[(1-phenylpropyl)amino]pyrazin-2-yl}-6-
  methoxyindan-1-one;

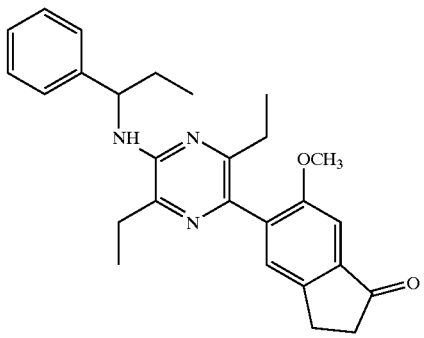

5-{5-[(3-amino-1-methylpropyl)amino]-3,6-diethylpyrazin-
  2-yl}-6-methoxyindan-1-one;

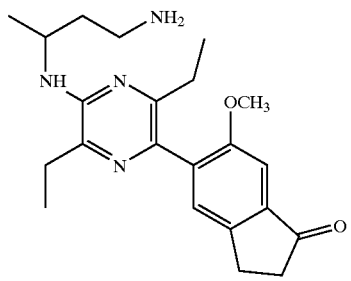

N-(3-{[3,6-diethyl-5-(6-methoxy-2,3-dihydro-1H-inden-5-
  yl)pyrazin-2-yl]amino}butyl)urea;

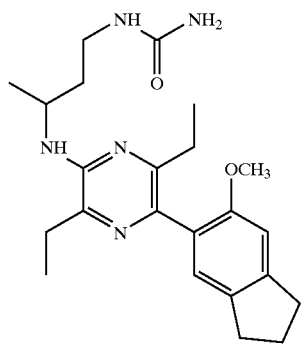

N-(3-{[3,6-diethyl-5-(6-methoxy-2,3-dihydro-1H-inden-5-
  yl)pyrazin-2-yl]amino}butyl)thiourea;

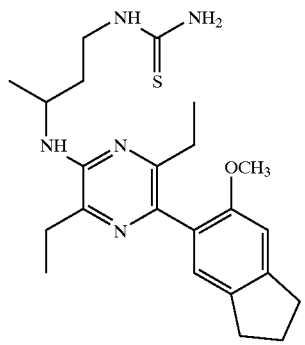

5-[6-(difluoromethoxy)-2,3-dihydro-1H-inden-5-yl]-3,6-
  diethyl-N-(1-ethylpropyl)pyrazin-2-amine;

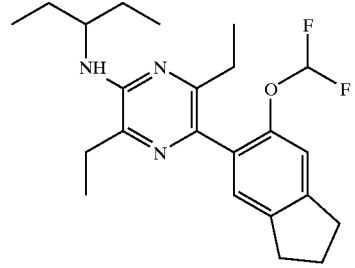

5-[3-(difluoromethoxy)-5,6,7,8-tetrahydronaphthalen-2-yl]-
  3,6-diethyl-N-(1-ethylpropyl)pyrazin-2-amine;

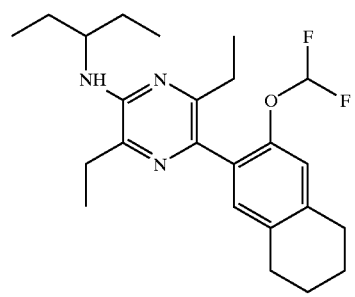

3,6-diethyl-N-(1-ethylpropyl)-5-[6-(trifluoromethoxy)-2,3-
  dihydro-1H-inden-5-yl]pyrazin-2-amine;

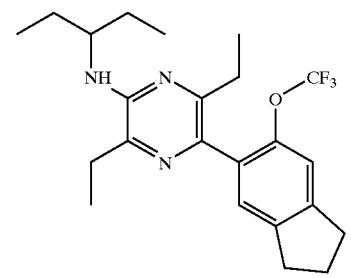

5-[6-(difluoromethoxy)-4-methoxy-2,3-dihydro-1H-inden-
  5-yl]-3,6-diethyl-N-(1-ehtylpropyl)pyrazin2-amine;

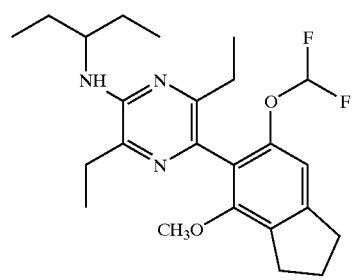

5-(4,6-dimethyl-2,3-dihydro-1H-inden-5-yl)-3,6-diethyl-N-(1-ethylpropyl)pyrazin-2-amine;

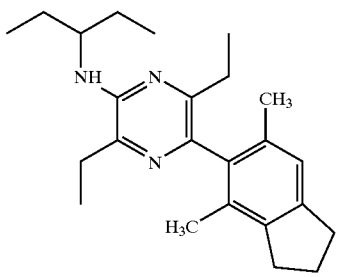

5-(1,3-dimethoxy-5,6,7,8-tetrahydronaphthalen-2-yl)-3,6-diethyl-N-(1-ethylpropyl)pyrazin-2-amine;

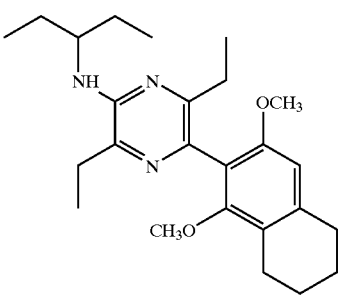

5-[3-(difluoromethoxy)-1-methoxy-5,6,7,8-tetrahydronaphthalen-2-yl]-3,6-diethyl-N-(1-ethylpropyl)pyrazin-2-amine;

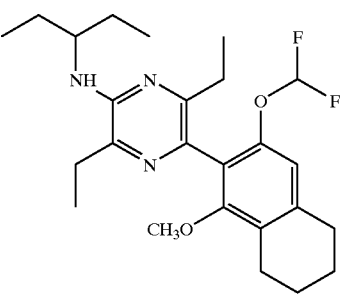

5-{4-[3-(dimethylamino)propyl]-6-methoxy-2,3-dihydro-1H-inden-5-yl}-3,6-diethyl-N-(1-ehtylpropyl)pyrazin-2-amine;

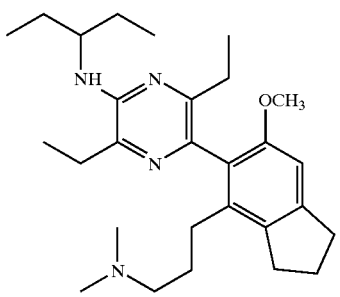

5-{4-[2-(dimethylamino)ethoxy]-6-methoxy-2,3-dihydro-1H-inden-5-yl}-3,6-diethyl-N-(1-ethylpropyl)pyrazin-2-amine;

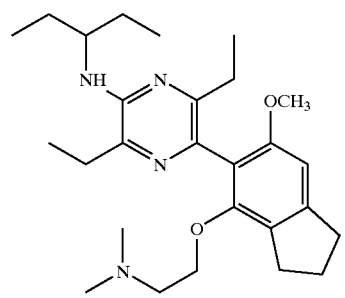

3,6-diethyl-N-(1-ethylpropyl)-5-[6-methoxy-4-(3-morpholin-4-ylpropyl)-2,3-dihydro-1H-inden-5-yl]pyrazin-2-amine;

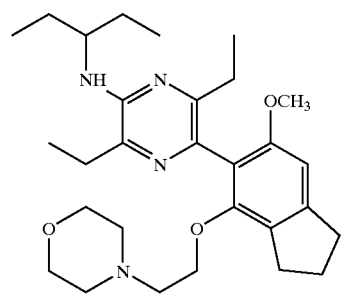

3,6-diethyl-N-(1-ethylpropyl)-5-[6-methoxy-4-(3-morpholin-4-ylpropyl)-2,3-dihydro-1H-inden-5-yl]pyrazin2-amine;

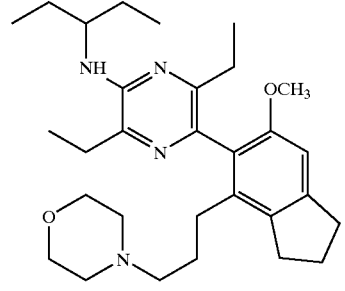

3,6-diethyl-5-(6-methoxy-2,3-dihydro-1H-inden-5-yl)-N-(1-pyridin-2-ylpropyl)pyrazin-2-amine;

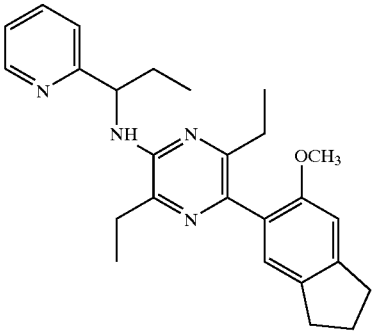

3,6-diethyl-5-(6-methoxy-2,3-dihydro-1H-inden-5-yl)-N-(2-methoxy-1-phenylethyl)pyrazin-2-amine;

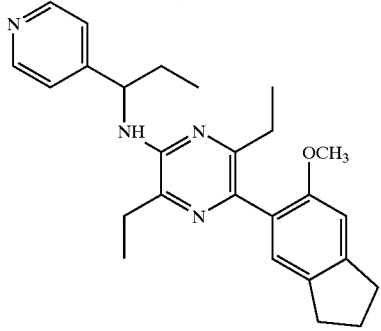

3,6-diethyl-5-(6-methoxy-2,3-dihydro-1H-inden-5-yl)-N-(2-methoxy-1-phenylethyl)pyrazin-2-amine;

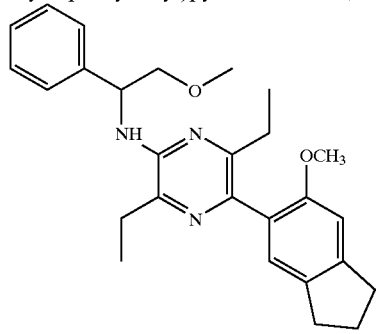

3,6-diethyl-5-(3-methoxy-5,6,7,8-tetrahydronaphthalen-2-yl)-N-(1-pyridin-3-ylpropyl)pyrazin-2-amine;

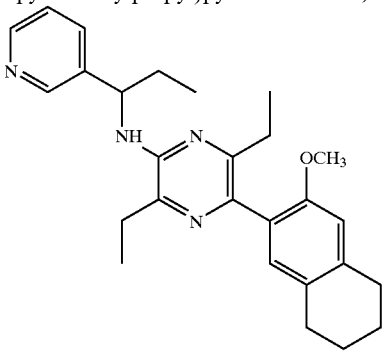

3-{[3,6-diethyl-5-(3-methoxy-5,6,7,8-tetrahydronaphthalen-2-yl)pyrazin-2-yl]amino}-3-phenylpropan-1-ol;

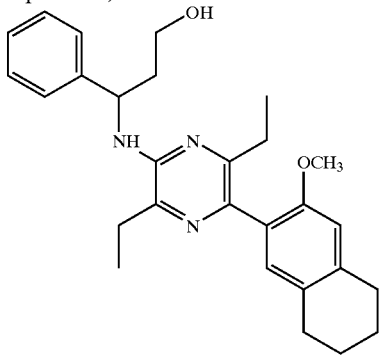

3,6-diethyl-N-(3-methoxy-1-phenylpropyl)-5-(3-methoxy-5,6,7,8-tetrahydronaphthalen-2-yl)pyrazin-2-amine;

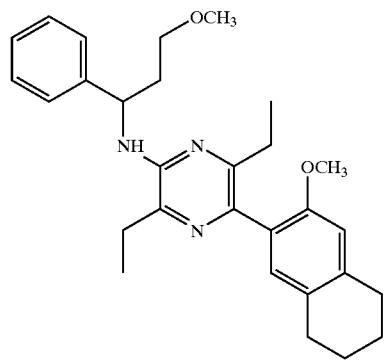

3,6-diethyl-N-(1-ethylpropyl)-5-(5-fluoro-3-methoxy-7,8-dihydronaphthalen-2-yl)pyrazin-2-amine;

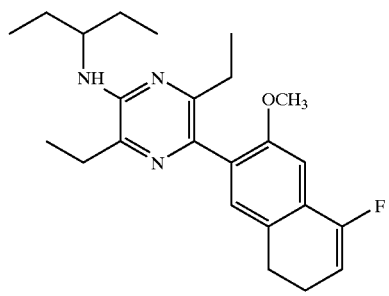

N,N,3,6-tetraethyl-5-(6-methoxy-2,3-dihydro-1H-inden-5-yl)pyrazine-2-carboxamide;

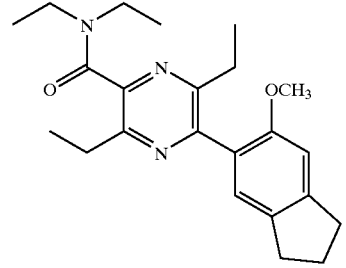

3,6-diethyl-N-(1-ethylpropyl)-5-(1-fluoro-6-methoxy-2,3-dihydro-1H-inden-5-yl)pyrazin-2-amine;

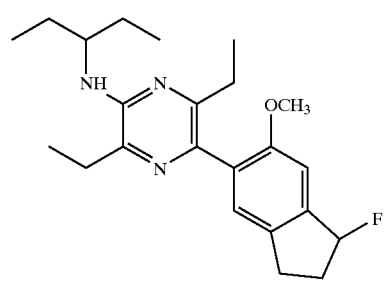

3,6-diethyl-N-(1-ethylpropyl)-5-(2-fluoro-6-methoxy-2,3-dihydro-1H-inden-5-yl)pyrazin-2-amine;

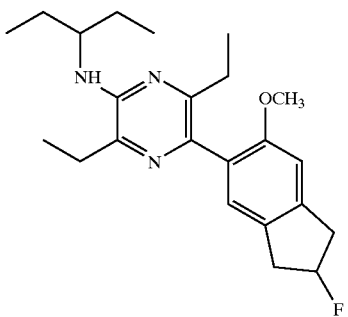

It should be understood that compounds provided herein can have one or more asymmetric centers or planes, and all chiral (enantiomeric and diastereomeric) and racemic forms of the compound are included in the present invention. Many geometric isomers of olefins, C=N double bonds, and the like can also be present in the compounds, and all such stable isomers are contemplated in the present invention. Compounds of the invention are isolated in either the racemic form, or in the optically pure form, for example, by resolution of the racemic form by conventional methods such as crystallization in the presence of a resolving agent, or chromatography, using, for example, a chiral HPLC column, or synthesized by a asymmetric synthesis route enabling the preparation of enantiomerically enriched material. The present invention encompasses all possible tautomers of the compounds represented by Formula I.

Compounds of the present invention can be prepared using the reactions depicted in Schemes I to IV indicated below. Starting materials can be prepared by procedures described in these charts or by procedures that would be well known to one of ordinary skill in organic chemistry. The variables used in the schemes are as defined below or as in the claims.

According to the general Method A (Scheme I), wherein $R_1$ and $R_2$ are as defined for Formula 1 and Z represents a halogen atom, suitably chloride or bromide, the halide in I can be displaced by an amine or (thio)alkoxide nucleophile. Thus, aminopyrazine II can be prepared from I and an amine in the presence of a suitable transition metal catalyst such as, but not limited to, palladium(II) acetate or tris (dibenzylideneacetone)dipalladium(0), a ligand such as, but not limited to, 1,1'-bis(diphenylphosphine)ferrocene, 2,2'-bis(diphenylphosphine)-1,1'-binaphthyl, dicyclohexyl(2-biphenyl)phosphine, tricyclohexylphosphine, or tri-tert-butylphosphine, and a base such as sodium or potassium tert-butoxide in inert solvents such as, but not limited to, toluene, ethyleneglycol dimethyl ether, diglyme, DMF, or N-methylpyrrolidinone at temperatures ranging from ambient to 100° C. (Thio)alkoxypyrazines can be prepared by treating I with a sodium or potassium salt of an alcohol or thiol in an inert solvent such as THF, DMF, N-methylpyrrolidinone, or methyl sulfoxide at ambient temperature or at elevated temperature up to the boiling point of the solvent employed. Halogenation of II to afford III may be accomplished by a variety of methods known in the art, including treatment with N-chlorosuccinimide, bromine, N-bromosuccinimide, pyridinium tribromide, triphenylphosphine dibromide, iodine, and N-iodosuccinimide in solvents such as but not limited to dichloromethane, acetic acid, or methyl sulfoxide. The halopyrazine III can be converted to arylpyrazine IV by a transition metal-catalyzed coupling reaction with a metalloaryl reagent (G-[M]). More commonly employed reagent/catalyst pairs include aryl boronic acid/palladium(0) (Suzuki reaction; N. Miyaura and A. Suzuki, *Chemical Review* 1995, 95, 2457), aryl trialkylstannane/palladium(0) (Stille reaction; T. N. Mitchell, *Synthesis* 1992, 803), arylzinc/palladium(0) and aryl Grignard/nickel(II). Palladium(0) represents a catalytic system made of a various combination of metal/ligand pair which includes, but not limited to, tetrakis(triphenylphosphine)palladium(0), palladium(II) acetate/tri(o-tolyl)phosphine, tris(dibenzylideneacetone)dipalladium(0)/tri-tert-butylphosphine and dichloro[1,1'-bis(diphenylphosphine)ferrocene]palladium(0). Nickel(II) represents a nickel-containing catalyst such as [1,2-bis(diphenylphosphino)ethane]dichloronickel(II) and [1,3-bis(diphenylphosphino)propane]dichloronickel(II). The arylpyrazine IV, when X is NH, may be further transformed to V by N-alkylation. The N—H group is deprotonated by a strong base such as, but not limited to, alkali metal hydride, alkali metal amide, or alkali metal alkoxide in inert solvents such as, but not limited to, THF, DMF, or methyl sulfoxide. Alkylation may be conducted using alkyl halide, suitably bromide or iodide, at temperatures ranging from 0° C. to 100° C.

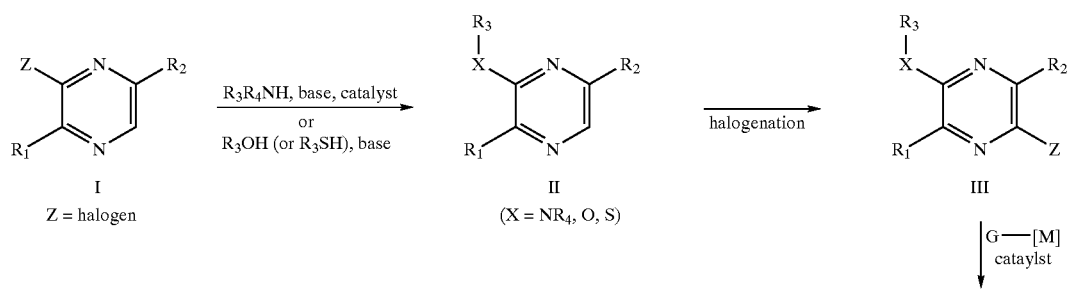

Scheme I (Method A)

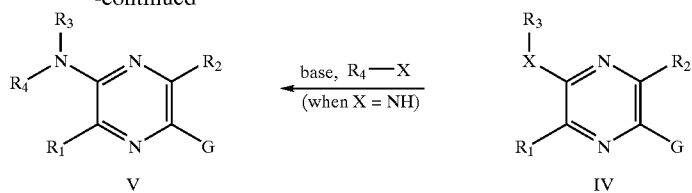

Compounds of Formula III can also be prepared as outlined in Scheme II (Method B). Transition metal-catalyzed coupling of the halo pyrazine I as described in the Method A can provide the intermediate VI. Oxidation of the sterically less hindered nitrogen can be effected by using a variety of oxidizing agents known in the art, such as m-chloroperoxybenzoic acid, trifluoroperacetic acid, hydrogen peroxide, and monoperoxyphthalic acid to give the N-oxide VII. The N-oxide VII can undergo rearrangement upon treatment with phosphorus oxychloride at temperatures ranging from ambient to 100° C. to give chloropyrazine VIII. Displacement of the chloride with a nitrogen, oxygen, or sulfur nucleophile as described in Method A can furnish the compounds of Formula III.

Scheme II (Method B)

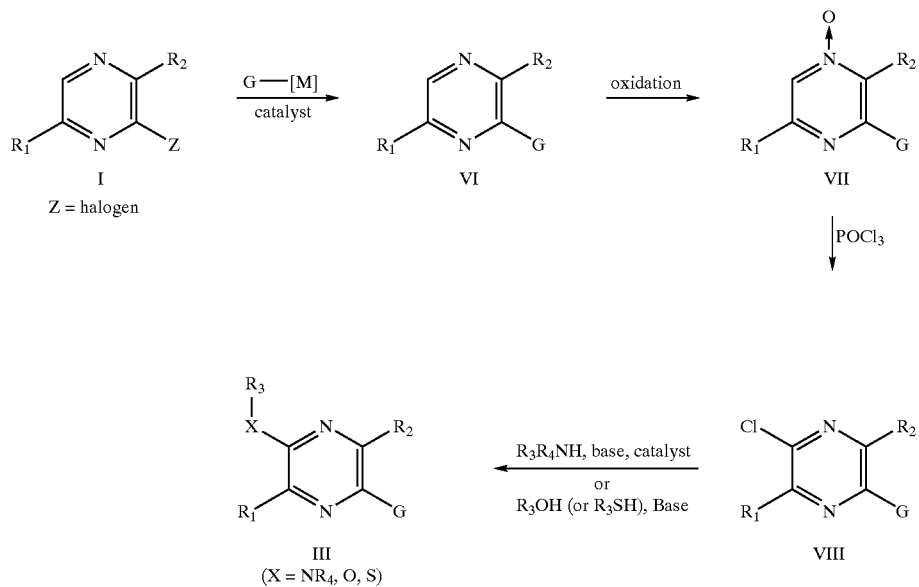

Yet another way of preparing compounds of formula III is illustrated by Method C in Scheme III. Compounds of formula IX, 3,6-dialkyl-2,5-dichloropyrazines, can be prepared from 2-alkylglycine according to a known literature procedure (*Chem. Pharm. Bull. Jpn.* 1979, 27, 2027). Nucleophilic displacement of one chloride followed by Suzuki-type coupling on the other chloride, as described in the Method A, can furnish the compounds of formula III.

Scheme III (Method C)

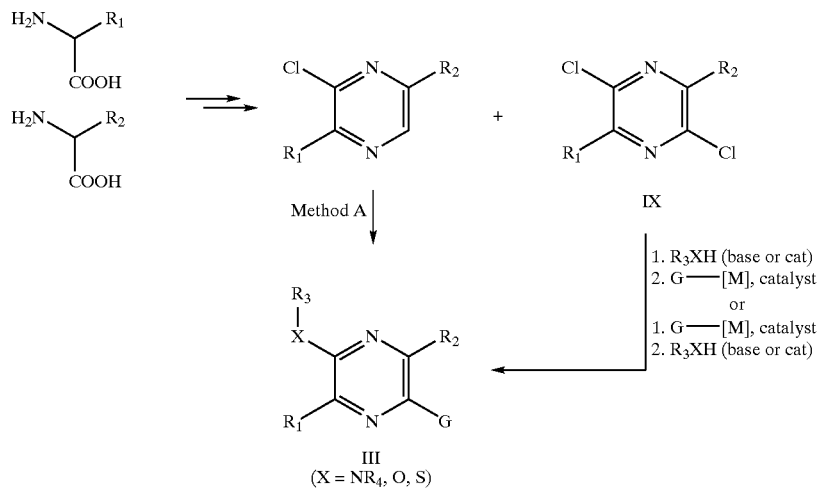

Scheme IV (Method D) illustrates an additional method for further elaborating compounds such as III. Suitably substituted indane and tetrahydronaphthalene compounds are widely known in the literature and are useful precursors for metalloaryl reagents G-[M]. For example, the known bromo ether X (Han, Wei; Lu, Yingchun; Zhao, He; Dutt, Mahesh; Biehl, Edward R., *Synthesis*, 1996, 59–63) can be carried through the synthetic sequences described above to afford the methoxy-containing III. Cleavage of the methoxy group under conditions known to those skilled in the art (illustrated here using phosphorous tribromide; see Vogel's Textbook of Practical Organic Chemistry, 1989, John Wiley and Sons for additional methods) gives the phenol XI. Alkylation of the phenolic oxygen of XI by treatment with base (such as but not limited to potassium or sodium carbonate, potassium or sodium hydroxide, etc) and an appropriate electrophile $R_5$—X (suitably an alkyl bromide or iodide) in an inert solvent (such as but not limited to THF, DMF, or methyl sulfoxide) at temperatures ranging from 0° C. to 100° C. gives the elaborated compounds XII.

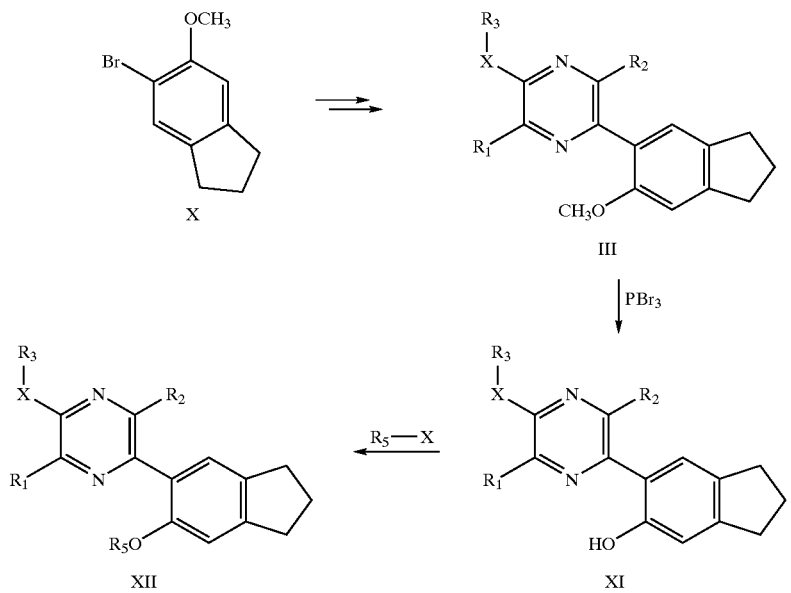

The present invention also encompasses pharmaceutically acceptable salts of compounds of Formula I. Examples of pharmaceutically acceptable salts are salts prepared from inorganic acids or organic acids, such as inorganic and organic acids of basic residues such as amines, for example, acetic, benzenesulfonic, benzoic, amphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, barbaric acid, p-toluenesulfonic and the like; and alkali or organic salts of acidic residues such as carboxylic acids, for example, alkali and alkaline earth metal salts derived from the following bases: sodium hydride, sodium hydroxide, potassium hydroxide, calcium hydroxide, aluminum hydroxide, lithium hydroxide, magnesium hydroxide, zinc hydroxide, ammonia, trimethylammonia, triethylammonia, ethylenediamine, lysine, arginine, ornithine, choline, N,N'-dibenzylethylenediamine, chloroprocaine, diethanolamine, procaine, n-benzylphenethylamine, diethylamine, piperazine, tris(hydroxymethyl)-aminomethane, tetramethylammonium hydroxide, and the like.

Pharmaceutically acceptable salts of the compounds of the invention can be prepared by conventional chemical methods. Generally, such salts are, for example, prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 17$^{th}$ ed., Mack Publishing Company, Easton, Pa., 1985, p. 1418, the disclosure of which is hereby incorporated by reference.

In another aspect, the present invention provides a prodrug of a compound of Formula I. The prodrug is prepared with the objective(s) of improved chemical stability, improved patient acceptance and compliance, improved bioavailability, prolonged duration of action, improved organ selectivity (including improved brain penetrance), improved formulation (e.g., increased hydrosolubility), and/or decreased side effects (e.g., toxicity). See e.g. T. Higuchi and V. Stella, "Prodrugs as Novel Delivery Systems", Vol. 14 of the A.C.S. Symposium Series; Bioreversible Carriers in Drug Design, ed. Edward B. Roche, American Pharmaceutical Association and Pergamon Press, (1987). Prodrugs include, but are not limited to, compounds derived from compounds of Formula I wherein hydroxy, amine or sulfhydryl groups, if present, are bonded to any group that, when administered to the subject, cleaves to form the free hydroxyl, amino or sulfhydryl group, respectively. Selected examples include, but are not limited to, biohydrolyzable amides and biohydrolyzable esters and biohydrolyzable carbamates, carbonates, acetate, formate and benzoate derivatives of alcohol and amine functional groups.

The prodrug can be readily prepared from the compounds of Formula I using methods known in the art. See, e.g. See Notari, R. E., "Theory and Practice of Prodrug Kinetics," Methods in Enzymology, 112:309–323 (1985); Bodor, N., "Novel Approaches in Prodrug Design," Drugs of the Future, 6(3):165–182 (1981); and Bundgaard, H., "Design of Prodrugs: Bioreversible-Derivatives for Various Functional Groups and Chemical Entities," in Design of Prodrugs (H. Bundgaard, ed.), Elsevier, N.Y. (1985); Burger's Medicinal Chemistry and Drug Chemistry, Fifth Ed., Vol. 1, pp. 172–178, 949–982 (1995). For example, the compounds of Formula I can be transformed into prodrugs by converting one or more of the hydroxy or carboxy groups into esters.

The invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{123}$I, and $^{125}$I. Compounds of Formula I that contain the aforementioned isotopes and/or other isotopes of other atoms are within the scope of the invention. Isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly useful in PET (positron emission tomography), and $^{125}$I isotopes are particularly useful in SPECT (single photon emission computed tomography); all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, maybe preferred in some circumstances. Isotopically labeled compounds of Formula I of this invention can generally be prepared by carrying out the synthetic procedures by substituting a isotopically labeled reagent for a non-isotopically labeled reagent.

The compounds of Formula I are antagonists at the $CRF_1$ receptor, capable of inhibiting the specific binding of CRF to $CRF_1$ receptor and antagonizing activities associated with $CRF_1$ receptor. The effectiveness of a compound as a CRF receptor antagonist may be determined by various assay methods. A compound of Formula I may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* 1:572, 1987). CRF receptor affinity may be determined by binding studies that measure the ability of a compound to inhibit the binding of a radiolabeled CRF (e.g., [$^{125}$I]tyrosine-CFR) to its receptor (e.g., receptors prepared from rat cerebral cortex membranes). The radioligand binding assay described by DeSouza et al. (supra, 1987) provides an assay for determining a compound's affinity for the CRF receptor. Such activity is typically calculated from the $IC_{50}$ as the concentration of a compound necessary to displace 50% of the radiolabeled ligand from the receptor, and is reported as a "Ki" value calculated by the following equation:

$$Ki = \frac{IC50}{1 + L/K_D}$$

where L=radioligand and $K_D$=affinity of radioligand for receptor (Cheng and Prusoff, Biochem. Pharmacol. 22:3099, 1973). An example of the receptor binding assay is provided in Example A below. Preferably compounds of the invention exhibit an $IC_{50}$ value for CRF binding of 1 micromolar or less, more preferably of 100 nanomolar or less and even more preferably of 10 nanomolar or less.

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)). An example of the CRF-stimulated adenylate cyclase activity assay is provided in Example C below.

Thus, in another aspect, the present invention provides a method of antagonizing $CRF_1$ receptors in a warm-blooded animal, comprising administering to the animal a compound of the invention at amount effective to antagonize $CRF_1$ receptors. The warm-blooded animal is preferably a mammal, and more preferably a human.

In another aspect, the present invention provides a method of treating a disorder in a warm-blooded animal, which disorder manifests hypersecretion of CRF, or the treatment of which disorder can be effected or facilitated by antagonizing $CRF_1$ receptors, comprising administering to the animal a therapeutically effective amount of a compound of the invention. The warm-blooded animal is preferably a mammal, and more preferably a human.

In another aspect, the present invention provides a method for screening for ligands for $CRF_1$ receptors, which method comprises: a) carrying out a competitive binding assay with $CRF_1$ receptors, a compound of Formula I which is labelled with a detectable label, and a candidate ligand; and b) determining the ability of said candidate ligand to displace said labelled compound. Assay procedure for competitive binding assay is well known in the art, and is exemplified in Example A.

In another aspect, the present invention provides a method for detecting $CRF_1$ receptors in tissue comprising: a) contacting a compound of Formula I, which is labeled with a detectable label, with a tissue, under conditions that permit binding of the compound to the tissue; and b) detecting the labeled compound bound to the tissue. Assay procedure for detecting receptors in tissues is well known in the art.

In another aspect, the present invention provides a method of inhibiting the binding of CRF to $CRF_1$ receptors, comprising contacting a compound of the invention with a solution comprising cells expressing the $CRF_1$ receptor, wherein the compound is present in the solution at a concentration sufficient to inhibit the binding of CRF to the $CRF_1$ receptor. An example of the cell line that expresses the $CRF_1$ receptor and can be used in the in vitro assay is IMR32 cells known in the art.

Compounds of formula (I), or a stereoisomer, a pharmaceutically acceptable salt, or a prodrug thereof, are useful for the treatment of a disorder in a warm-blooded animal, which disorder manifests hypersecretion of CRF, or the treatment of which disorder can be effected or facilitated by antagonizing $CRF_1$ receptors. Examples of such disorders are described herein above. They are also useful for promoting smoking cessation or promoting hair growth.

Thus, in still another aspect, the present invention provides a method of treating a disorder described herein above, comprising administering to a warm-blooded animal a therapeutically effective amount of a compound of the invention. The warm-blooded animal is preferably a mammal, particularly a human.

Particular disorders that can be treated by the method of the invention preferably include the following: anxiety-relatred disorders (such as generalized anxiety disorder; social anxiety disorder; anxiety; anxiety with co-morbid depressive illness, obsessive-compulsive disorder, and panic disorder); mood disorders (such as depression, including major depression, single episode depression, recurrent depression, child abuse induced depression, and postpartum depression); bipolar disorders; post-traumatic stress disorder; substance abuse disorder (e.g., nicotine, cocaine, ethanol, opiates, or other drugs); inflammatory disorders (such as rheumatoid arthritis and osteoarthritis); gastrointestinal diseases (such as irritable bowel syndrome, ulcers, Crohn's disease, spastic colon, diarrhea, and post operative ilius and colonic hypersensitivity associated by psychopathological disturbances or stress); inflammatory disorder; and skin disorders (such as acne, psoriasis, and chronic contact demertitis).

Particular disorders that can be treated by the method of the invention more preferably include the following: anxiety-related disorders; mood disorders; inflammation disorders; and chronic contact demertitis.

Particular disorders that can be treated by the method of the invention even more preferably include anxiety-related disorders, particularly generalized anxiety, and mood disorders, particularly major depression.

The therapeutically effective amounts of the compounds of the invention for treating the diseases or disorders described above in a warm-blooded animal can be determined in a variety of ways known to those of ordinary skill in the art, e.g., by administering various amounts of a particular agent to an animal afflicted with a particular condition and then determining the effect on the animal. Typically, therapeutically effective amounts of a compound of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation will be effective in obtaining the desired pharmacological effect. It will be understood, however, that the specific dose levels for any particular patient will depend upon a variety of factors including the activity of the specific compound employed, the age, body weight, general health, sex, diet, time of administration, route of administration, and rate of excretion, drug combination and the severity of the particular disease. Frequency of dosage may also vary depending on the compound used and the particular disease treated. However, for treatment of most CNS disorders, a dosage regimen of four-times daily or less is preferred. For the treatment of stress and depression, a dosage regimen of one or two-times daily is particularly preferred.

A compound of this invention can be administered to treat the above disorders by means that produce contact of the active agent with the agent's site of action in the body of a mammal, such as by oral, topical, dermal, parenteral, or rectal administration, or by inhalation or spray using appripropriate dosage forms. The term "parenteral" as used herein includes subcutaneous injections, intravenous, intramuscular, intrasternal injection or infusion techniques. The compound can be administered alone, but will generally be administered with a pharmaceutically acceptable carrier, diluent, or excipient.

Thus in yet another aspect, the present invention provides a pharmaceutical composition comprising a compound of Formula I, a stereoisomer thereof, a pharmaceutically acceptable salt thereof, or a prodrug thereof, or a pharmaceutically acceptable salt of the prodrug thereof. In one embodiment, the pharmaceutical composition further comprises a pharmaceutically acceptable carrier, diluent, or excipient therefore. A "pharmaceutically acceptable carrier, diluent, or excipient" is a medium generally accepted in the art for the delivery of biologically active agents to mammals, e.g., humans. Such carriers are generally formulated according to a number of factors well within the purview of those of ordinary skill in the art to determine and account for. These include, without limitation: the type and nature of the active agent being formulated; the subject to which the agent-containing composition is to be administered; the intended route of administration of the composition; and the therapeutic indication being targeted. Pharmaceutically acceptable carriers and excipients include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, well known to those of ordinary skill in the art. Descriptions of suitable pharmaceutically acceptable carriers, and factors involved in their selection, are found in a variety of readily available sources, e.g., Remington's Pharmaceutical Sciences, $17^{th}$ ed., Mack Publishing Company, Easton, Pa., 1985, the contents of which are incorporated herein by reference.

Compositions intended for oral use may be in the form of tablets, troches, lozenges, aqueous or oily suspensions, dispersible powders or granules, emulsion, hard or soft capsules, or syrups or elixirs, and can be prepared according to methods known to the art. Such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and a delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long aliphatic alcohols, for example heptadecaethyleneoxycetanol, or condensation products of ethylene oxide with partial esters derived from fatty acids and a hexital such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more sweetening agents, such as sucrose or saccharin.

Oily suspensions may be formulated by suspending the active ingredients in a vegetable oil, for example arachis oil, olive oil, soybean oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occuring gums, for example gum acacia or gum tragacanth, naturally-occuring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

Suppositories for rectal administration of a compound of the invention can be prepared by mixing the compound with a suitable non-irritating excipient, which is solid at ordinary temperatures but liquid at the rectal temperature and will therefore melt in the rectum to release the drug. Examples of such materials are cocoa butter and polyethylene glycols.

Pharmaceutical compositions may be in the form of a sterile injectable aqueous or oleaginous suspension. This suspension may be formulated according to the known art using those suitable dispersing or wetting agents and suspending agents, which have been mentioned above. The sterile injectable solution or suspension may be formulated in a non-toxic parentally acceptable diluent or solvent, for example as a solution in 1,3-butanediol. Among the acceptable vehicles and solvents that may be employed are water, Ringers's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Dosage forms suitable for administration generally contain from about 1 mg to about 100 mg of active ingredient per unit. In these pharmaceutical compositions, the active ingredient will ordinarily be present in an amount of about 0.5 to 95% by weight based on the total weight of the composition. Examples of dosage forms for administration of compounds of the invention includes the following: (1) Capsules. A large number of units capsules are prepared by filling standard two-piece hard gelatin capsules each with 100 mg of powdered active ingredient, 150 mg lactose, 50 mg cellulose, and 6 mg magnesium stearate; (2) Soft Gelatin Capsules. A mixture of active ingredient in a digestible oil such as soybean, cottonseed oil, or olive oil is prepared and injected by means of a positive displacement into gelatin to form soft gelatin capsules containing 100 mg of the active ingredient. The capsules were washed and dried; (3) Tablets. A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

In still another aspect, the present invention provides an article of manufacture comprising: a) a packaging material; b) a pharmaceutical agent comprising a compound of the invention contained within said packaging material; and c) a label or package insert which indicates that said pharmaceutical agent can be used for treating a disorder described above.

DEFINITIONS AND CONVENTIONS

The following definitions are used throughout the application, unless otherwise described.

The term "halogen" means a group selected from —F, —Cl, —Br, or —I.

The term "alkyl" means both straight- and branched-chain hydrocarbon moieties having from 1–10 carbon atoms optionally containing one or more double or triple bonds;

The term "substituted alkyl" means an alkyl moiety having 1–5 substitutents independently selected from halogen, oxo (=O), thione (=S), —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S(O)$_m$R$_a$, —NR$_a$C(O)OR$_a$, —NR$_a$C(O)NR$_a$R$_a$, —NR$_a$C(S)NR$_a$R$_a$, —C(O)OR$_a$, —C(S)OR$_a$, —OC(O)OR$_a$, OC(O)R$_a$, OC(S)R$_a$, NR$_a$C(S)OR$_a$, and OC(S)NR$_a$R$_a$;

The term "haloalkyl" means an alkyl moiety having 1 to (2v+1) independently selected halogen substituent(s) where v is the number of carbon atoms in the moiety;

The term "cycloalkyl" means a a monocyclic, non-aromatic hydrocarbon moiety, having from 3–10 carbon atoms or a bicyclic non-aromatic hydrocarbon moiety, having from 4 to 10 carbon atoms, optionally containing 1 to 2 double bonds;

The term "substituted cycloalkyl" means a cycloalkyl moiety having 1–5 substituents independently selected from halogen, oxo (=O), thione (=S), —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, —OC(O)OR$_a$, OC(O)R$_a$, OC(S)R$_a$, NR$_a$C(S)OR$_a$, and OC(S)NR$_a$R$_a$;

The term "aryl" means either phenyl or naphthyl;

The term "substituted aryl" means an aryl group substituted with 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S(O)$_m$R$_a$, —NR$_a$C(O)OR$_a$, —NR$_a$C(S)OR$_a$, —OC(O)NR$_a$R$_a$, —OC(S)NR$_a$R$_a$, —NR$_a$C(O)NR$_a$R$_a$, —NR$_a$C(S)NR$_a$R$_a$, —C(O)OR$_a$, —C(S)OR$_a$, —OC(O)R$_a$, OC(S)R$_a$, —OC(O)OR$_a$, OC(O)R$_a$, OC(S)R$_a$, NR$_a$C(S)OR$_a$, and OC(S)NR$_a$R$_a$;

The term "heteroaryl" means a radical of a monocyclic aromatic ring containing five or six ring atoms consisting of carbon and 1 to 4 heteroatoms each selected from the group consisting of non-peroxide O, S, N, with appropriate bonding to satisfy valence requirements, wherein the attachment may be via a ring carbon or ring N where a N is present. The term "heteroaryl" also includes a radical of a fused bicyclic heteroaromatic ring having eight to ten ring atoms consisting of carbon and 1 to 6 heteroatoms each selected from non-peroxide O, S, N, with appropriate bonding to satisfy valence requirements, wherein the attachment may be via a ring carbon or ring N where a N is present. Examples of heteroaryl include thienyl, benzothienyl, pyridyl, thiazolyl, quinolyl, pyrazinyl, pyrimidyl, imidazolyl, furanyl, benzofuranyl, benzothiazolyl, isothiazolyl, benzisothiazolyl, benzisoxazolyl, benzimidazolyl, indolyl, and benzoxazolyl, pyrazolyl, triazolyl, tetrazolyl, isoxazolyl, oxazolyl, pyrrolyl, isoquinolinyl, cinnolinyl, indazolyl, indolizinyl, phthalazinyl, pydridazinyl, triazinyl, isoindolyl, purinyl, oxadiazolyl, furazanyl, benzofurazanyl, benzothiophenyl, benzothiazolyl, quinazolinyl, quinoxalinyl, naphthridinyl, and furopyridinyl;

The term "substituted heteroaryl" means a heteroaryl group having 1–5 substituents independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, ≦C(O)OR$_a$, —C(S)OR$_a$, —OC(O)OR$_a$, OC(O)R$_a$, OC(S)R$_a$, NR$_a$C(S)OR$_a$, and OC(S)NR$_a$R$_a$;

The term "heterocycloalkyl", unless otherwise specified, means a 3 to 8 membered monocyclic non-aromatic ring or a 4 to 8 membered bicyclic non-aromatic ring, wherein at least one carbon atom is replaced with a heteroatom selected from oxygen, nitrogen, —NH—, or —S(O)$_m$— wherein m is zero, 1, or 2, optionally containing from one to three double bonds, and wherein the ring attachment can occur at either a carbon or nitrogen atom. Examples of heterocycloalkyl includes tetrahydrofuranyl, tetrahydropyranyl, morpholinyl, pyrrolidinyl, piperidinyl, piperazinyl, [2.2.1]-azabicyclic rings, [2.2.2]-azabicyclic rings, [3.3.1]-azabicyclic rings, quinuclidinyl, azetidinyl, azetidinonyl, oxindolyl, dihydroimidazolyl, and pyrrolidinonyl;

The term "substituted heterocycloalkyl" is a heterocycloalkyl group having 1–5 substituents independently selected from halogen, oxo (=O), thione (=S), —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, —OC(O)OR$_a$, OC(O)R$_a$, OC(S)R$_a$, NR$_a$C(S)OR$_a$, and OC(S)NR$_a$R$_a$;

The term "aryl cycloalkyl" means a bicyclic ring system containing 8 to 14 carbon atoms wherein one ring is aryl and the other ring is fused to the aryl ring and may be fully or partially saturated in the portion of the ring fused to the aryl ring, wherein either ring may act as a point of attachment;

The term "substituted aryl cycloalkyl" means an aryl cycloalkyl group having 1–5 substituents independently selected from halogen, oxo (=O), thione (=S), —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S(O)$_m$R$_a$, —NR$_a$C(O)OR$_a$, —OC(O)NR$_a$R$_a$, —NR$_a$C(O)NR$_a$R$_a$, —NR$_a$C(S)NR$_a$R$_a$, —C(O)OR$_a$, —C(S)OR$_a$, —OC(O)OR$_a$, OC(O)R$_a$, OC(S)R$_a$, NR$_a$C(S)OR$_a$, and OC(S)NR$_a$R$_a$;

The term "heteroaryl cycloalkyl" means a bicyclic ring system containing 8 to 14 atoms, wherein one ring is heteroaryl and the other ring is fused to the heteroaryl ring and may be fully or partially saturated in the portion of the ring fused to the heteroaryl ring, wherein either ring may act as a point of attachment;

The term "substituted heteroaryl cycloalkyl" means a heteroaryl cycloalkyl group having 1–5 substituents independently selected from halogen, oxo (=O), thione (=S), —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S (O)$_m$R$_a$, —NR$_a$C(O)OR$_a$, —OC(O)NR$_a$R$_a$, —NR$_a$C(O) NR$_a$R$_a$, —NR$_a$C(S)NR$_a$R$_a$, —C(O)OR$_a$, —C(S)OR$_a$, —OC(O)OR$_a$, OC(O)R$_a$, OC(S)R$_a$, NR$_a$C(S)OR$_a$, and OC(S)NR$_a$R$_a$;

The term "aryl heterocycloalkyl" means a bicyclic ring system containing 8 to 14 atoms, wherein one ring is aryl and the other ring is heterocycloalkyl, wherein either ring may act as a point of attachment;

The term "substituted aryl heterocycloalkyl" means an aryl heterocycloalkyl group having 1–5 substituents independently selected from halogen, oxo (=O), thione (=S), —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S (O)$_m$R$_a$, —NR$_a$C(O)OR$_a$, —OC(O)NR$_a$R$_a$, —NR$_a$C(O) NR$_a$R$_a$, —NR$_a$C(S)NR$_a$R$_a$, —C(O)OR$_a$, —C(S)OR$_a$, —OC(O)OR$_a$, OC(O)R$_a$, OC(S)R$_a$, NR$_a$C(S)OR$_a$, and OC(S)NR$_a$R$_a$;

The term "heteroaryl heterocycloalkyl" means a bicyclic ring system containing 8 to 14 atoms, wherein one ring is heteroaryl and the other ring is heterocycloalkyl, wherein either ring may act as a point of attachment;

The term "substituted heteroaryl heterocycloalkyl" means an heteroaryl heterocycloalkyl group having 1–5 substituents independently selected from halogen, oxo (=O), thione (=S), —NO$_2$, —CN, —R$_a$, OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S (O)$_m$R$_a$, —NR$_a$C(O)OR$_a$, —OC(O)NR$_a$R$_a$, —NR$_a$C(O) NR$_a$R$_a$, —NR$_a$C(S)NR$_a$R$_a$, —C(O)OR$_a$, —C(S)OR$_a$, —OC(O)OR$_a$, OC(O)R$_a$, OC(S)R$_a$, NR$_a$C(S)OR$_a$, and OC(S)NR$_a$R$_a$;

The term "pharmaceutically acceptable," unless otherwise described, refer to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

The term "pharmaceutically acceptable salt" refers to a salt which retains the biological effectiveness and properties of the compounds of this invention and which is not biologically or otherwise undesirable.

The term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "prodrug" means compounds that are transformed in vivo to yield a compound of Formula I. The transformation may occur by various mechanisms, such as through hydrolysis in blood.

The term "therapeutically effective amount," "effective amount," "therapeutic amount," or "effective dose" is meant that amount sufficient to elicit the desired pharmacological or therapeutic effects, thus resulting in effective prevention or treatment of the disease.

The phrases "a compound of the invention," "a compound of the present invention," "compounds of the present invention," or "a compound in accordance with Formula I" and the like, refer to compounds of Formula I, or stereoisomers thereof, pharmaceutically acceptable salts thereof, or prodrugs thereof, or pharmaceutically acceptable salts of a prodrug of compounds of Formula I.

The terms "treatment," "treat," "treating," and the like, are meant to include both slowing or reversing the progression of a disorder, as well as curing the disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed. The term "treatment" and like terms also include preventive (e.g., prophylactic) and palliative treatment. Prevention of the disease is manifested by a prolonging or delaying of the onset of the symptoms of the disease.

EXAMPLES

Without further elaboration, it is believed that one skilled in the art can, using the preceding description, practice the present invention to its fullest extent. The following examples are provided to illustrate the invention and are not to be construed as limiting the invention in scope or spirit to the specific procedures described in them. The numerical examples (Example 1–45) and preparations are provided to illustrate the preparation of compounds of the invention and Examples A–D are provided to illustrate biological assays that can be used for determining the biological properties of the compounds of the inventions. Those skilled in the art will promptly recognize appropriate variations from the procedures described in the examples.

Example A in vitro CRF$_1$ Receptor Binding Assay for the Evaluation of Biological Activity The following is a description of a standard in vitro binding assay for the evaluation of biological activity of a test compound on CRF$_1$ receptors. It is based on a modified protocol described by De Souza (De Souza, 1987).

The binding assay utilizes brain membranes, commonly from rats. To prepare brain membranes for binding assays, rat frontal cortex is homogenized in 10 mL of ice cold tissue buffer (50 mM HEPES buffer pH 7.0, containing 10 mM MgCl$_2$, 2 mM EGTA, 1 μg/mL aprotinin, 1 μg/mL leupeptin and 1 μg/mL pepstatin). The homogenate is centrifuged at 48,000×g for 10 min. and the resulting pellet rehomogenized in 10 mL of tissue buffer. Following an additional centrifugation at 48,000×g for 10 min., the pellet is resuspended to a protein concentration of 300 μg/mL.

Binding assays are performed in 96 well plates at a final volume of 300 μL. The assays are initiated by the addition of 150 μL membrane suspension to 150 μL of assay buffer containing $^{125}$I-ovine-CRF (final concentration 150 pM) and various concentrations of inhibitors. The assay buffer is the same as described above for membrane preparation with the addition of 0.1% ovalbumin and 0.15 mM bacitracin. Radioligand binding is terminated after 2 hours at room temperature by filtration through Packard GF/C unifilter plates (presoaked with 0.3% polyethyleneimine) using a Packard cell harvestor. Filters are washed three times with ice cold phosphate buffered saline pH 7.0 containing 0.01% Triton X-100. Filters are assessed for radioactivity in a Packard TopCount.

Alternatively, tissues and cells that naturally express CRF receptors, such as IMR-32 human neuroblastoma cells (ATCC; Hogg et al., 1996), can be employed in binding assays analogous to those described above.

A compound is considered to be active if it has an $IC_{50}$ value of less than about 10 μM for the inhibition of CRF. Nonspecific binding is determined in the presence of excess (10 μM) α-helical CRF.

Example B
Ex vivo $CRF_1$ Receptor Binding Assay for the Evaluation of Biological Activity The following is a description of a typical ex vivo $CRF_1$ receptor binding assay for assessing the biological activity of a test compound on $CRF_1$ receptors.

Fasted, male, Harlen-bred, Sprague-Dawley rats (170–210 g) were orally dosed with test compound or vehicle, via gastric lavage between 12:30 and 2:00 PM. Compounds were prepared in vehicle (usually 10% soybean oil, 5% polysorbate 80, in dH20). Two hours after drug administration, rats were sacrificed by decapitation, frontal cortices were quickly dissected and placed on dry ice, then frozen at −80° C. until assayed; trunk blood was collected in heparinized tubes, plasma separated by centrifugation (2500 RPM's for 20 minutes), and frozen at −20° C.

On the day of the binding assay, tissue samples were weighed and allowed to thaw in ice cold 50 mM Hepes buffer (containing 10 mM $MgCl_2$, 2 mM EGTA, 1 μg/mL aprotinin, 1 μg/mL leupeptin hemisulfate, and 1 μg/mL pepstatin A, 0.15 mM bacitracin, and 0.1% ovalbumin, pH=7.0 at 23° C.) and then homogenized for 30 sec at setting 5 (Polytron by Kinematica). Homogenates were incubated (two hours, 23° C., in the dark) with [$^{125}$I] CRF (0.15 nM, NEN) in the presence of assay buffer (as described above) or DMP-904 (10 uM). The assay was terminated by filtration (Packard FilterMate, GF/C filter plates); plates were counted in Packard TopCount LSC; total and non-specific fmoles calculated from DPM's. Data are expressed as % of vehicle controls (specific fmoles bound). Statistical significance was determined using student's t-test.

Example C
Inhibition of CRF Stimulated Adenylate Cyclase Activity

Inhibition of CRF-stimulated adenylate cyclase activity can be performed as previously described [G. Battaglia et al., *Synapse* 1:572 (1987)]. Briefly, assays are carried out at 37° C. for 10 min in 200 mL of buffer containing 100 mM Tris-HCl (pH 7.4 at 37° C.), 10 mM $MgCl_2$, 0.4 mM EGTA, 0.1% BSA, 1 mM isobutylmethylxanthine (IBMX), 250 units/mL phosphocreatine kinase, 5 mM creatine phosphate, 100 mM guanosine 5'-triphosphate, 100 nM o-CRF, antagonist peptides (various concentrations) and 0.8 mg original wet weight tissue (approximately 40–60 mg protein). Reactions are initiated by the addition of 1 mM ATP/[$^{32}$P]ATP (approximately 2–4 mCi/tube) and terminated by the addition of 100 mL of 50 mM Tris-HCl, 45 mM ATP and 2% sodium dodecyl sulfate. In order to monitor the recovery of cAMP, 1 mL of [$^3$H]cAMP (approximately 40,000 dpm) is added to each tube prior to separation. The separation of [$^{32}$P]cAMP from [$^{32}$P]ATP is performed by sequential elution over Dowex and alumina columns.

Alternatively, adenylate cyclase activity can be assessed in a 96-well format utilizing the Adenylyl Cyclase Activation FlashPlate Assay from NEN Life Sciences according to the protocols provided. Briefly, a fixed amount of radiolabeled cAMP is added to 96-well plates that are precoated with anti-cyclic AMP antibody. Cells or tissues are added and stimulated in the presence or absence of inhibitors. Unlabeled cAMP produced by the cells will displace the radiolabeled cAMP from the antibody. The bound radiolabeled cAMP produces a light signal that can be detected using a microplate scintillation counter such as the Packard TopCount. Increasing amounts of unlabeled cAMP results in a decrease of detectable signal over a set incubation time (2–24 hours).

Example D
in vivo Biological Assay

The in vivo activity of a compound of the present invention can be assessed using any one of the biological assays available and accepted within the art. Illustrative of these tests include the Acoustic Startle Assay, the Stair Climbing Test, and the Chronic Administration Assay. These and other models useful for the testing of compounds of the present invention have been outlined in C. W. Berridge and A. J. Dunn Brain Research Reviews 15:71 (1990). A compound may be tested in any species of rodent or small mammal.

Preparation 1

3-methoxy-5,6,7,8-tetrahydronaphthalen-2-ylboronic acid

Step 1: 1-bromo-5,6,7,8-tetrahydronaphthalen-2-ol; 3-bromo-5,6,7,8-tetrahydronaphthalen-2-ol

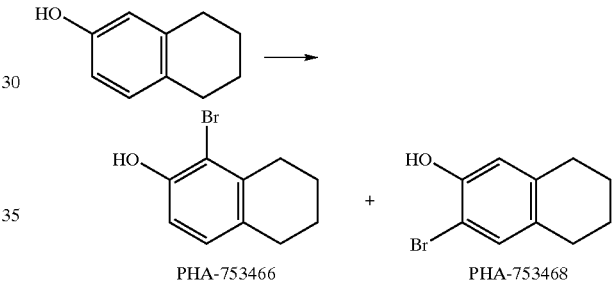

PHA-753466      PHA-753468

An oven dried 1 L round bottom flask was charged with 5,6,7,8-tetrahydro-2-naphthol (4 g, 26.8 mmol) and $CCl_4$ (536 mL). The solution was cooled to 0° C. with an ice bath for 30 minutes, followed by the slow addition of a solution of $Br_2$ (4.28 g, 26.8 mmol) in $CCl_4$ (27 mL). The reaction was stirred at 0° C. for 30 minutes then placed in the freezer at −10° C. for 18 hours. The reaction was then allowed to warm to ambient temperature. TLC shows the reaction complete. The reaction was concentrated in vacuo to give 6.16 g of an ivory laced with dark brown solid. The crude was purified in four batches by Biotage MPLC (120 g columns, 2.5% ethyl acetate). Purification gave 2.83 g (46%) of 1-bromo-5,6,7,8-tetrahydronaphthalen-2-ol as a white solid, 2.28 g (37%) of a mixed fractions (1-bromo-5,6,7,8-tetrahydronaphthalen-2-ol and 3-bromo-5,6,7,8-tetrahydronaphthalen-2-ol) and 0.56 g (9%) of 3-bromo-5,6,7,8-tetrahydronaphthalen-2-ol as a white solid.

1-bromo-5,6,7,8-tetrahydronaphthalen-2-ol, Rf 0.33 (10% ethyl acetate in heptane) $^1$H NMR (400 MHz, $CDCl_3$) δ 6.94 (d, J=8 Hz, 1 H), 6.81 (d, J=8 Hz, 1 H), 5.46 (s, 1 H), 2.71 (t, J=6 Hz, 4 H), 1.82 (m, 2 H), 1.73 (m, 2 H); $^{13}$C NMR (100 MHz, $CDCl_3$) δ 136.6, 131.0, 129.1, 113.5, 112.8, 30.5, 29.3, 23.1, 22.7. 3-bromo-5,6,7,8-tetrahydronaphthalen-2-ol, Rf 0.28 (10% ethyl acetate in heptane) $^1$H NMR (400 MHz, $CDCl_3$) δ 7.15 (s, 1 H), 6.73 (s, 1 H), 5.30 (s, 1 H), 2.67 (m, 4 H), 1.75(q, J=4 Hz, 4 H).

Step 2: 3-bromo-5,6,7,8-tetrahydronaphthalen-2-yl methyl ether

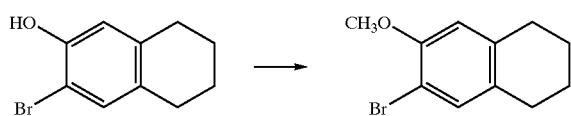

A 21 mL oven dried scintillation vial with a Teflon lined cap was charged with 3-bromo-5,6,7,8-tetrahydronaphthalen-2-ol (568 mg, 2.50 mmol), powdered $K_2CO_3$ (691 mg, 5.00 mmol), dry DMF (7 mL) and iodomethane (0.622 mL, 10.00 mmol). The flask was purged with $N_2$ sealed and heated on the orbital shaker to 50° C. for 4 hours. After cooling the reaction to ambient temperature, it was concentrated under high vacuum to remove DMF, and then partitioned between brine:water (1:1) and ethyl acetate (2×). The organics were combined, dried with $Na_2SO_4$, filtered and concentrated to a crude paste. The crude was purified by Biotage MPLC (90 g column, 2.5% ethyl acetate in heptane) to give 571 mg (94%) of 3-bromo-5,6,7,8-tetrahydronaphthalen-2-yl methyl ether as a white solid. Rf 0.57 (10% ethyl acetate in heptane) $^1$H NMR shows ~6% contamination with the 1-bromo regio-iosmer. $^1$H NMR (400 MHz, $CDCl_3$) δ 7.23 (s, 1 H), 6.59 (s, 1 H), 3.85 (s, 3 H), 2.69 (m, 4 H), 1.76 (m, 4 H); $^{13}$C NMR (100 MHz, $CDCl_3$) δ 153.4, 137.4, 133.4, 130.8, 112.4, 108.3, 56.2, 29.5, 28.3, 23.1, 22.9.

Step 3: 3-methoxy-5,6,7,8-tetrahydronaphthalen-2-ylboronic acid

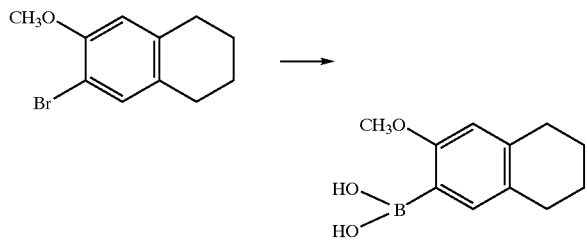

A 10 mL round bottom flask was charged with 3-bromo-5,6,7,8-tetrahydronaphthalen-2-yl methyl ether (560 mg, 2.32 mmol) and dried under high vacuum for 18 hours. The aryl bromide was diluted with THF (3.5 mL) and cooled to −78° C. with a dry ice/acetone bath. After 20 minutes, n-butyl lithium (2.5 M in hexane, 1.02 mL, 2.55 mmol) was added semi-drop wise. The reaction was kept at −78° C. for another hour before triethylborate (0.435 mL, 2.55 mmol) was added semi-drop wise and stirred at −78° C. for two hours. The reaction was quenched at −78° C. with 3M aq. HCl and allowed to warm to room temperature. The resulting biphasic mixture was partitioned between $H_2O$ and ethyl acetate (2×). The organics were combined and dried over $Na_2SO_4$, filtered and concentrated to give 510 mg (theoretical 478 mg) of 3-methoxy-5,6,7,8-tetrahydronaphthalen-2-ylboronic acid as an ivory solid. $^1$H NMR shows contamination with ~11% of the des-bromo by product. $^1$H NMR (400 MHz, $CDCl_3$) δ 7.51 (s, 1 H), 6.61 (s, 1 H), 5.73 (s, 2 H), 3.87 (s, 3 H), 2.78 (m, 2 H), 2.71 (m, 2 H), 1.79 (m, 4 H).

Preparation 2

6-methoxy-2,3-dihydro-1H-inden-5-ylboronic acid

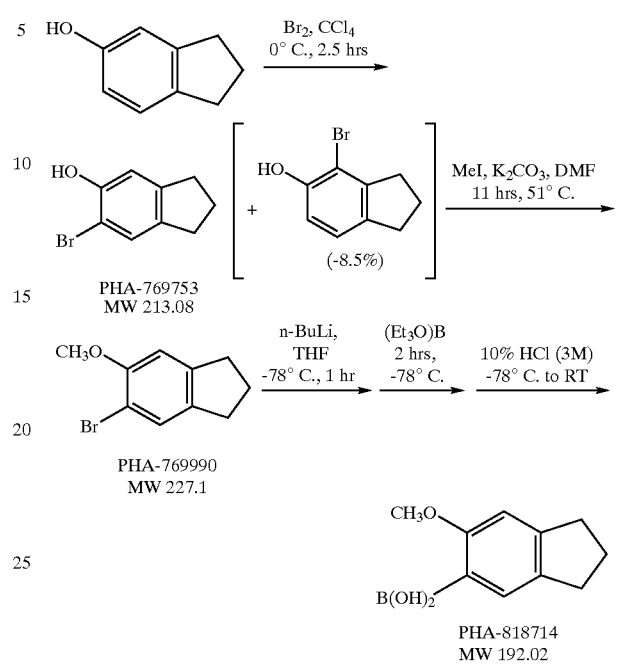

Step 1: 6-bromoindan-5-ol

A dry 2 liter round bottom flask was charged with 5-indanol (10.0 g, 74.5 mmol) and $CCl_4$ (1L) under nitrogen atmosphere. The flask was cooled with an ice bath. $Br_2$ was added drop-wise. The orange color dissipated as the bromine was added. A water bubbler was used to trap HBr generated. The reaction was stirred 0° C. for 2.5 hours. The pale yellow solution was checked by TLC and concentrated in vacuo to 16.39 grams of a yellow-orange oil. Iodine was used to visualize the TLC plates. The crude was purified using the Biotage MPLC in two batches (120 gram columns, using 5% ethyl acetate). Like fractions were combined to give 14.85 grams (93%) of a white solid. $^1$H NMR shows 8.5% of the regio-isomer. The regio-isomers were separated [Chiralpak AD column (7.6 by 50 cm) at 30° C.; flow rate: 100 mL/min; eluent: 10% isopropyl alcohol in heptane; loading: 13 mL injections of 100 mg/mL in isopropyl alcohol] to give 1.39 grams of 4-bromoindan-5-ol as a yellow oil (88% minor isomer by HPLC) and 12.74 grams of 6-bromoindan-5-ol as a yellow oil (100% major isomer by HPLC). The major isomer was purified by Biotage MPLC in two batches (120 g columns, 5% ethyl acetate). Like fractions were combined to give 12.33 grams (93%) of 6-bromoindan-5-ol as a pale yellow oil. IR (liq.) 3510, 2951, 2303, 2212, 2071, 1578, 1474, 1436, 1413, 1331, 1273, 1194, 1178, 1106, 867 cm$^{-1}$. Anal. Calcd for $C_9H_9BrO$: C, 50.73; H, 4.26; Br, 37.50. Found: C, 50.77; H, 4.38; N, 0.15. Found: Br, 37.34

Step 2: 6-bromo-2,3-dihydro-1H-inden-5-yl methyl ether

Four oven dried 40 mL vials with Teflon lined caps were used in parallel for the reaction. The sealed vials were used to avoid loss of MeI. Each of the the vials was loaded with a fourth of 6-bromoindan-5-ol (12.01 g, 56.36 mmol), $K_2CO_3$ (15.58 g, 112.72 mmol), DMF (147.5 mL) and MeI (14.03 mL, 225.45 mmol) respectfully. The vials were sealed and heated on the orbital shaker for a total of 11 hours at 51° C. The reactions in the four vials were combined, poured in water and extracted twice with ethyl acetate. The organics were combined, dried with Na$_2$SO$_4$, filtered and concentrated to give 12.6 grams of a crude yellow oil. The crude was purified using the in two batches (120 g columns, 5% ethyl acetate). Like fractions were combined to give 9.53 grams (74%) of 6-bromo-2,3-dihydro-1H-inden-5-yl methyl ether as a white solid and 2.29 grams (19%) of recovered 6-bromoindan-5-ol. IR (diffuse reflectance) 2958, 2468, 2428, 2415, 2350, 2337, 1482, 1466, 1392, 1311, 1278, 1260, 865, 835, 733 cm$^{-1}$. Anal. Calcd for C$_{10}$H$_{11}$BrO: C, 52.89; H, 4.88; Br, 35.18. Found: C, 52.87; H, 4.79; N, 0.21. Found: Br, 35.27. X-Ray supports the structure.

Step 3: 6-methoxy-2,3-dihydro-1H-inden-5-ylboronic acid

A dry 250 mL round bottom flask was charged with 6-bromo-2,3-dihydro-1H-inden-5-yl methyl ether (9.38 grams, 41.27 mmol) and placed under high vacuum for 18 hours. THF (51.6 mL) was added via syringe. The solution was homogeneous and clear. The reaction was cooled with a dry ice/acetone bath for 15 minutes, then n-BuLi was added semi-dropwise. A color change to pale yellow was observed. The reaction was stirred at −78° C. for 1 hour, followed by drop-wise addition of triethylborate (7.73 mL, 45.43 mmol). After continued stirring and cooling at −78° C. for 2 hours, the reaction was quenched with 10% aq. HCl (50 mL, 3M), the cooling bath was removed, and the reaction was allowed to warm to ambient temperature. The reaction was poured in water and extracted two times with ethyl acetate. The organics were combined, dried with MgSO4, filtered and concentrated to 8.0 grams of 6-methoxy-2,3-dihydro-1H-inden-5-ylboronic acid as a white, somewhat tacky, solid. The solid turned blue over 48 hours. The boronic acid was used without further purification.

Example 1

3,6-diethyl-N-(1-ethylpropyl)-5-(6-methoxy-2,3-dihydro-1H-inden-5-yl)pyrazin-2-amine

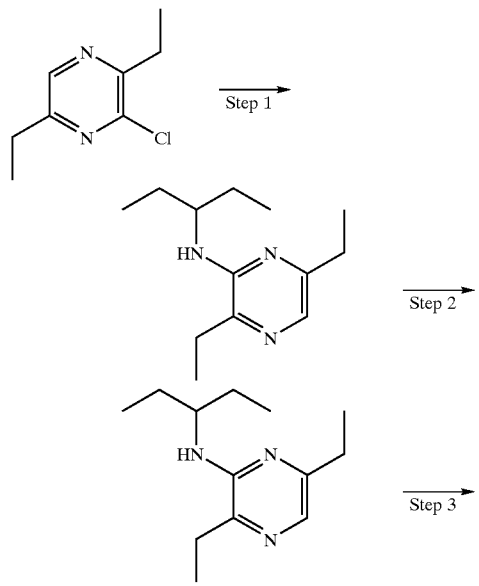

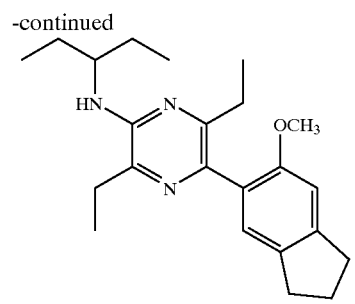

Step 1: 3,6-diethyl-N-(1-ethylpropyl)pyrazin-2-amine

A 250 mL dry round bottom flask equipped with a magnetic stir bar and reflux condenser was charged with 2-chloro-3,6-diethylpyrazine (9.22 g, 54 mmol), dry toluene (108 mL), 1-ethyl propylamine (12.6 mL, 108 mmol), 2-(di-tert-butylphosphino)biphenyl (0.966 g, 3.24 mmol), sodium tert-butoxide (7.26 g, 75.6 mmol), and tris (dibenzylidineacetone)dipalladium (0) (1.48 g, 1.62 mmol) respectively. The mixture was heated to 100° C. for 4 hours. After cooling to ambient temperature, the reaction was poured in saturated aqueous NaHCO$_3$ and extracted twice with ethyl acetate. The organics were combined, dried with Na$_2$SO$_4$, filtered and concentrated to 14.1 g of a dark crude oil. The crude was purified by Biotage MPLC in two batches (120 g columns, 10% ethyl acetate in heptane.) Like fractions were combined to give 10.0 g (84%) of 3,6-diethyl-N-(1-ethylpropyl)pyrazin-2-amine as an orange oil.

Step 2: 5-bromo-3,6-diethyl-N-(1-ethylpropyl)pyrazin-2-amine

A 500 mL dry round bottom flask equipped with a magnetic stir bar was charged with 3,6-diethyl-N-(1-ethylpropyl)pyrazin-2-amine (10.0 g, 45.18 mmol) and CH$_2$Cl$_2$ (220 mL). After the mixture was cooled with an ice bath, N-bromosuccinimide (8.84 g, 49.7 mmol) was added at once. The mixture was stirred at 0° C. for 30 minutes then quenched with saturated aq. NaHCO$_3$, diluted with H$_2$O and extrated twice with CH$_2$Cl$_2$. The organics were combined, dried with NaSO$_4$, filtered and concentrated to 13.96 g of a brown oil. The crude was purified by Biotage MPLC in two batches (120 g columns, 2.5% ethyl acetate in heptane.) Like fractions were combined to give 11.57 g (85%) of 5-bromo-3,6-diethyl-N-(1-ethylpropyl)pyrazin-2-amine as a yellow oil.

Step 3: 3,6-diethyl-N-(1-ethylpropyl)-5-(6-methoxy-2,3-dihydro-1H-inden-5-yl)pyrazin-2-amine A scintillation vial with a Teflon lined cap was charged with 5-bromo-3,6-diethyl-N-(1-ethylpropyl)pyrazin-2-amine (300.2 mg, 1 mmol), 6-methoxy-2,3-dihydro-1H-inden-5-ylboronic acid (211.2 mg, 1.1 mmol, Preparation 2), terakis(triphenylphosphine)palladium (0) (116 mg, 0.1 mmol), 2M Na$_2$CO$_3$ (1 mL, 2 mmol), and ethylene glycol dimethyl ether (6 mL). The reaction was heated on the orbital shaker to 80° C. for 30 hours. After cooling to ambient temperature, the reaction was partitioned between H$_2$O and ethyl acetate. The aqueous layer was extracted one more time with ethyl acetate. The organics were combined, dried with Na$_2$SO$_4$, filtered and concentrated to 530 mg of a yellow crude oil. The crude was purified by Biotage MPLC (90 g column, 1.5% acetone in toluene) to give 243 mg (66%) of 3,6-diethyl-N-(1-ethylpropyl)-5-(6-methoxy-2,3-dihydro-1H-inden-5-yl)pyrazin-2-amine as a pale yellow oil. Rf 0.19 (10% ethyl acetate in heptane). IR (liq.) 2964, 2935, 2874, 1566, 1550, 1484, 1464, 1444, 1391, 1380, 1276, 1253, 1203, 1174, 1033 cm$^{-1}$. OAMS supporting ions at: ESI+368.3. HRMS (ESI) calcd for $C_{23}H_{33}N_3O+H_1$ 368.2702, found 368.2703. Anal. Calcd for $C_{23}H_{33}N_3O$: C, 75.16; H, 9.05; N, 11.43. Found: C, 75.25; H, 9.15; N, 11.13.

Example 2

3,6-diethyl-N-(1-ethylpropyl)-5-(3-methoxy-5,6,7,8-tetrahydronaphthalen-2-yl)pyrazin-2-amine

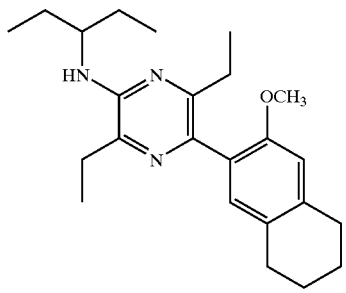

Following the general procedure of Example 1 Step 3 and making non-critical variations but substituting 6-methoxy-2,3-dihydro-1H-inden-5-ylboronic acid (Preparation 2) with 3-methoxy-5,6,7,8-tetrahydronaphthalen-2-ylboronic acid (Preparation 3), the reaction was carried out on 5-bromo-3, 6-diethyl-N-(1-ethylpropyl)pyrazin-2-amine (8 g, 26.64 mmol) and gave 17.06 g of crude oil. The crude was purified on multiple batches by Biotage MPLC (120 g columns, 1.5% acetone in heptane) to give 8.2 g (81%) of 3,6-diethyl-N-(1-ethylpropyl)-5-(3-methoxy-5,6,7,8-tetrahydronaphthalen-2-yl)pyrazin-2-amine as a clear oil. Rf 0.38 (2% acetone in toluene). IR (liq.) 2964, 2933, 2875, 2858, 1565, 1550, 1508, 1485, 1464, 1444, 1391, 1310, 1248, 1204, 1174 cm$^{-1}$. OAMS supporting ions at: ESI+ 382.3 Anal. Calcd for $C_{24}H_{35}N_3O$: C, 75.55; H, 9.25; N, 11.01. Found: C, 75.49; H, 9.41;N, 10.67.

Example 3

3,6-diethyl-N-(1-ethylpropyl)-5-(4-methoxy-7-methyl-2,3-dihydro-1H-inden-5-yl)pyrazin-2-amine

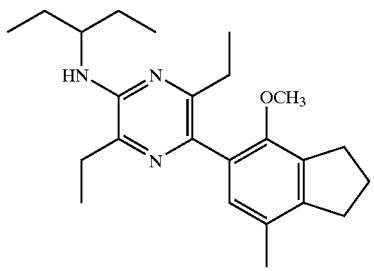

Step 1: 4-methoxy-7-methyl-2,3-dihydro-1H-inden-5-ylboronic acid

Following the general procedure of Preparation 1 Step 3 and making non-critical variations but substituting 3-bromo-5,6,7,8-tetrahydronaphthalene-2-yl methyl ether with 5-bromo-4-methoxy-7-methyl indane (482 mg, 2 mmol) gave 380 mg of crude mixture that was 80% by weight of 4-methoxy-7-methyl-2,3-dihydro-1H-inden-5-ylboronic acid and 20% 4-methoxy-7-methylindane.

Step 2: 3,6-diethyl-N-(1-ethylpropyl)-5-(4-methoxy-7-methyl-2,3-dihydro-1H-inden-5-yl)pyrazin-2-amine Following the general procedure of Example 1 Step 3 and making non-critical variations but substituting the boronic acid with the crude described above, the reaction was carried out on 5-bromo-3,6-diethyl-N-(1-ethylpropyl)pyrazin-2-amine (133 mg, 0.46 mmol) and gave 309 mg of a crude yellow oil. This material was purified by Biotage MPLC (40 g column, 10% acetone in heptane) to give 117 mg (67%) of 3,6-diethyl-N-(1-ethylpropyl)-5-(4-methoxy-7-methyl-2,3-dihydro-1H-inden-5-yl)pyrazin-2-amine as an oil. Rf 0.40 (10% acetone in heptane). IR (liq.) 2964, 2935, 2874, 1565, 1551, 1494, 1475, 1464, 1445, 1392, 1381, 1225, 1211, 1173, 1068 cm$^{-1}$. OAMS supporting ions at: ESI+382.2. HRMS (ESI) calcd for $C_{24}H_{35}N_3O+H_1$ 382.2858, found 382.2860. Anal. Calcd for $C_{24}H_{35}N_3O$: C, 75.55; H, 9.25; N, 11.01. Found: C, 75.23; H, 9.79; N, 10.87.

Example 4

3,6-diethyl-N-(1-ethylpropyl)-5-(2-methoxy-5,6,7,8-tetrahydronaphthalen-1-yl)pyrazin-2-amine

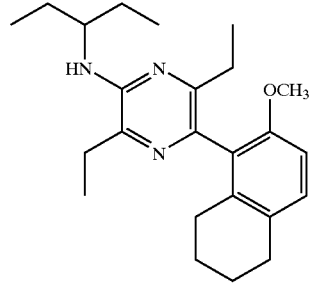

Step 1: 1-bromo-5,6,7,8-tetrahydronaphthalen-2-yl methyl ether

Following the general procedure of Preparation 1 Step 2 and making non-critical variations but substituting 3-bromo-5,6,7,8-tetrahydronaphthalen-2-ol, with 1-bromo-5,6,7,8-tetrahydronaphthalen-2-ol (840 mg, 3.70 mmol), gave 888 mg of crude yellow oil. The crude was purified by Biotage MPLC (90 g column, 2.5% ethyl acetate in heptane) to give 426 mg (47%) of 1-bromo-5,6,7,8-tetrahydronaphthalen-2-yl methyl ether as an oil.

Step 2: 2-methoxy-5,6,7,8-tetrahydronaphthalen-1-ylboronic acid

Following the general procedure of Preparation 1 Step 3 and making non-critical variations but substituting 3-bromo-5,6,7,8-tetrahydronaphthalene-2-yl methyl ether with 1-bromo-5,6,7,8-tetrahydronaphthalen-2-yl methyl ether (420 mg, 1.74 mmol) gave 354 mg of crude ivory solid mixture that was 74% by weight of 2-methoxy-5,6,7,8-tetrahydronaphthalen-1-ylboronic acid and 26% methyl 5,6,7,8-tetrahydronaphthalen-2-yl ether.

Step 3: 3,6-diethyl-N-(1-ethylpropyl)-5-(2-methoxy-5,6,7,8-tetrahydronaphthalen-1-yl)pyrazin-2-amine Following the general procedure of Example 1 Step 3 and making non-critical variations but substituting 6-methoxy-2,3-dihydro-1H-inden-5-ylboronic acid (Preparation 2) with the crude described above, the reaction was carried out on 5-bromo-3,6-diethyl-N-(1-ethylpropyl)pyrazin-2-amine (138 mg, 0.46 mmol) and gave 350 mg of a crude yellow oil. This material was purified by Biotage MPLC (40 g column, 10% ethyl acetate in heptane) to give 145 mg (82%) of 3,6-diethyl-N-(1-ethylpropyl)-5-(2-methoxy-5,6,7,8- tetrahydronaphthalen-1-yl)pyrazin-2-amine as a yellow oil. Rf 0.10 (10% ethyl acetate in heptane). IR (diffuse reflectance) 3394, 2969, 2950, 2933, 2907, 2874, 1495, 1480, 1462, 1443, 1391, 1381, 1251, 1175, 797 cm$^{-1}$. OAMS supporting ions at: ESI+382.2. Anal. Calcd for $C_{24}H_{35}N_3O$: C, 75.55; H, 9.25; N, 11.01. Found: C, 75.51; H, 9.27; N, 10.82

Example 5

3,6-diethyl-N-(1-ethylpropyl)-5-(4-methoxy-5,6,7,8-tetrahydronaphthalen-1-yl)pyrazin-2-amine

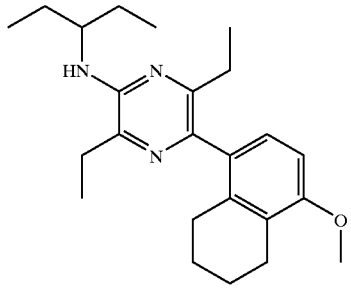

Step 1: 4-bromo-5,6,7,8-tetrahydronaphthalen-1-ol

Following the general procedure of Preparation 1 Step 1 and making non-critical variations but substituting 5,6,7,8-tetrahydro-2-naphthol with 5,6,7,8-tetrahydro-1-naphthol (1.0 g, 6.7 mmol) gave 1.57 g of an ivory solid. The crude was purified by Biotage MPLC (90 g column, 10% ethyl acetate in heptane) to give 1.34 (88%) of 4-bromo-5,6,7,8-tetrahydronaphthalen-1-ol.

Step 2: 4-bromo-5,6,7,8-tetrahydronaphthalen-1-yl methyl ether

Following the general procedure of Preparation 1 Step 2 and making non-critical variations but substituting 3-bromo-5,6,7,8-tetrahydronaphthalen-2-ol, with 4-bromo-5,6,7,8-tetrahydronaphthalen-1-ol (840 mg, 3.7 mmol) gave 842 mg of crude oil. The crude was purified by Biotage MPLC (40 g column, 2.5% ethyl acetate in heptane) to give 727 mg (82%) of 4-bromo-5,6,7,8-tetrahydronaphthalen-1-yl methyl ether as a clear oil.

Step 3: 4-methoxy-5,6,7,8-tetrahydronaphthalen-1-ylboronic acid

Following the general procedure of Preparation 1 Step 3 and making non-critical variations but substituting 3-bromo-5,6,7,8-tetrahydronaphthalene-2-yl methyl ether with 4-bromo-5,6,7,8-tetrahydronaphthalen-1-yl methyl ether (420 mg, 1.74 mmol) gave 344 mg of crude ivory solid mixture containing 4-methoxy-5,6,7,8-tetrahydronaphthalen-1-ylboronic acid.

Step 4: 3,6-diethyl-N-(1-ethylpropyl)-5-(4-methoxy-5,6,7,8-tetrahydronaphthalen-1-yl)pyrazin-2-amine Following the general procedure of Example 1 Step 3 and making non-critical variations but substituting 6-methoxy-2,3-dihydro-1H-inden-5-ylboronic acid (Preparation 2) with the crude described above (138 mg, 0.46 mmol) gave 420 mg of a crude yellow paste. This material was purified by Biotage MPLC (40 g column, 10% ethyl acetate in heptane) to give 112 mg (64%) of 3,6-diethyl-N-(1-ethylpropyl)-5-(4-methoxy-5,6,7,8-tetrahydronaphthalen-1-yl)pyrazin-2-amine as a white solid. Rf 0.32 (10% ethyl acetate in heptane). IR (diffuse reflectance) 2964, 2934, 2872, 2858, 1562, 1544, 1493, 1467, 1457, 1391, 1327, 1291, 1246, 1172, 1092 cm$^{-1}$. OAMS supporting ions at: ESI+382.2. HRMS (ESI) calcd for $C_{24}H_{35}N_3O+H_1$ 382.2858, found 382.2857. Anal. Calcd for $C_{24}H_{35}N_3O$: C, 75.55; H, 9.25; N, 11.01. Found: C, 75.60; H, 9.26; N, 10.86.

Example 6

5-(2-ethoxy-5,6,7,8-tetrahydronaphthalen-1-yl)-3,6-diethyl-N-(1-ethylpropyl)pyrazin-2-amine

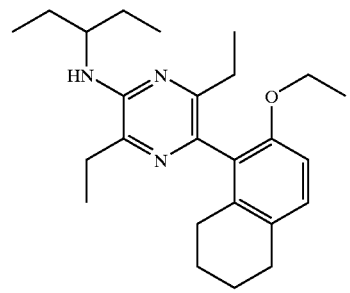

Step 1: 1-bromo-5,6,7,8-tetrahydronaphthalen-2-yl ethyl ether

Following the general procedure of Preparation 1 Step 2 and making non-critical variations but substituting 3-bromo-5,6,7,8-tetrahydronaphthalen-2-ol with 1-bromo-5,6,7,8-tetrahydronaphthalen-2-ol (900 mg, 3.96 mmol) and substituting iodomethane with iodoethane gave 980 mg of a crude oil. The crude was purified by Biotage MPLC (120 g column, 3% ethyl acetate in heptane) to give 657 mg (66%) of 1-bromo-5,6,7,8-tetrahydronaphthalen-2-yl ethyl ether as a white solid.

Step 2: 2-ethoxy-5,6,7,8-tetrahydronaphthalen-1-ylboronic acid

Following the general procedure of Preparation 1 Step 3 and making non-critical variations but substituting 3-bromo-5,6,7,8-tetrahydronaphthalene-2-yl methyl ether with 1-bromo-5,6,7,8-tetrahydronaphthalen-2-yl ethyl ether (444 mg, 1.74 mmol) gave 400 mg of crude ivory solid mixture that was 93% by weight of 2-ethoxy-5,6,7,8-tetrahydronaphthalen-1-ylboronic acid and 7% ethyl 5,6,7,8-tetrahydronaphthalen-2-yl ether.

Step 3: 5-(2-ethoxy-5,6,7,8-tetrahydronaphthalen-1-yl)-3,6-diethyl-N-(1-ethylpropyl)pyrazin-2-amine Following the general procedure of Example 1 Step 3 and making non-critical variations but substituting 6-methoxy-2,3-dihydro-1H-inden-5-ylboronic acid (Preparation 2) with the crude described above, the reaction was carried out on 5-bromo-3,6-diethyl-N-(1-ethylpropyl)pyrazin-2-amine (138 mg, 0.46 mmol) and gave 260 mg of a crude yellow paste. This material was purified by Biotage MPLC (90 g column, 10% ethyl acetate in heptane) to give 126 mg (70%) of 5-(2-ethoxy-5,6,7,8-tetrahydronaphthalen-1-yl)-3,6-diethyl-N-(1-ethylpropyl)pyrazin-2-amine as a clear oil. Rf 0.39 (10% ethyl acetate in heptane). IR (diffuse reflectance) 2959, 2931, 2874, 1564, 1497, 1493, 1469, 1442, 1389, 1382, 1249, 1204, 1181, 1113, 795cm$^{-1}$. OAMS supporting ions at: ESI+396.3. HRMS (ESI) calcd for $C_{25}H_{37}N_3O+H_1$ 396.3015, found 396.3019. Anal. Calcd for $C_{25}H_{37}N_3O$: C, 75.91; H, 9.43; N, 10.62. Found: C, 75.71; H, 9.27; N, 10.46.

Example 7

3-{3,6-diethyl-5-[(1-ethylpropyl)amino]pyrazin-2-yl}-5,6,7,8-tetrahydronaphthalen-2-ol

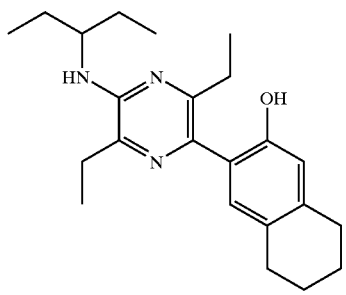

A 100 mL dry round bottom flask equipped with a magnetic stir bar was charged with 3,6-diethyl-N-(1-ethylpropyl)-5-(3-methoxy-5,6,7,8-tetrahydronaphthalen-2-yl)pyrazin-2-amine (Example 2, 3.39 g, 8.88 mmol) in $CH_2Cl_2$ (60 mL). After the sultion was cooled with an ice bath for 20 minutes, a 1M solution of $BBr_3$ in $CH_2Cl_2$ (13.33 mL, 13.33 mmol) was added drop-wise. The ice bath was removed after 20 minutes and the reaction was stirred at ambient temperature for 36 hours. The reaction mixture was poured into sat. $NaHCO_3$ and extracted twice with $CH_2Cl_2$. The organics were combined, dried with $MgSO_4$, filtered and concentrated to give 3.32 g of an oil. The crude was purified by Biotage MPLC (120 g column, 10% ethyl acetate in heptane) to give 2.73 g (84%) of 3-{3,6-diethyl-5-[(1-ethylpropyl)amino]pyrazin-2-yl}-5,6,7,8-tetrahydronaphthalen-2-ol as a yellow solid. Rf 0.31 (10% ethyl acetate in heptane). IR (diffuse reflectance) 3383, 2982, 2963, 2936, 2871, 1564, 1512, 1492, 1460, 1449, 1392, 1355, 1277, 1265, 1182 cm$^{-1}$. OAMS supporting ions at: ESI+368.3 HRMS (ESI) calcd for $C_{23}H_{33}N_3O+H_1$ 368.2702, found 368.2694. Anal. Calcd for $C_{23}H_{33}N_3O$: C, 75.16; H, 9.05; N, 11.43. Found: C, 75.27; H, 9.20; N, 11.43.

Example 8

3-{3,6-diethyl-5-[(1-ethylpropyl)amino]pyrazin-2-yl-}-5,6,7,8-tetrahydronaphthalen-2-yl trifluoromethanesulfonate

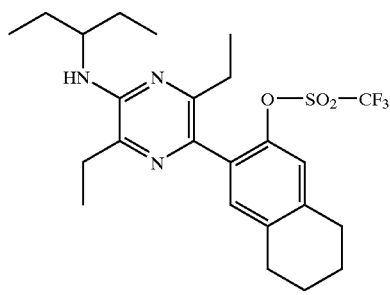

A 250 mL dry round bottom flask equipped with a magnetic stir bar and reflux condenser was charged with 3-{3,6-diethyl-5-[(1-ethylpropyl)amino]pyrazin-2-yl}-5,6,7,8-tetrahydronaphthalen-2-ol (Example 7, 2.73 g, 7.43 mmol), 2-[N,N-Bis(trifluoromethylsulfonyl)-amino]-5-chloropyridine (9.62 g, 24.51 mmol), $K_2CO_3$ (4.11 g, 29.71 mmol) and 1,2-dichloroethane (65 mL). The reaction was heated to a vigorous reflux for 66 hours. After cooling to ambient temperature, the reaction was poured into $H_2O$ and extracted two times with $CH_2Cl_2$. The organics were combined, dried with $MgSO_4$, filtered and concentrated to give 4.48 g of a dark orange oil. The crude was purified by Biotage MPLC (90 g column, toluene) to give 2.7 g (73%) of 3-{3,6-diethyl-5-[(1-ethylpropyl)amino]pyrazin-2-yl}-5,6,7,8-tetrahydronaphthalen-2-yl trifluoromethanesulfonate. Rf 0.18 (toluene). IR (liq.) 2967, 2937, 1556, 1509, 1485, 1464, 1447, 1421, 1394, 1249, 1219, 1209, 1143, 936, 857 cm$^{-1}$. OAMS supporting ions at: ESI+500.1. HRMS (ESI) calcd for $C_{24}H_{32}N_3O_3SF_3+H_1$ 500.2195, found 500.2184. Anal. Calcd for $C_{24}H_{32}F_3N_3O_3S$: C, 57.70; H, 6.46; N, 8.41; S, 6.42; F, 11.41. Found: C, 58.02; H, 6.56; N, 8.20.

Example 9

3,6-diethyl-N-(1-ethylpropyl)-5-(5,6,7,8-tetrahydronaphthalen-2-yl)pyrazin-2-amine

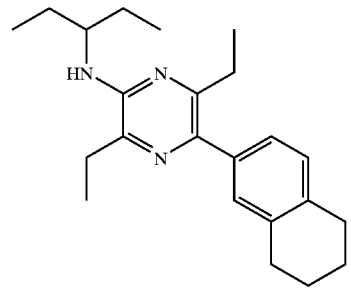

A 7 mL oven dried vial was charged with 3-{3,6-diethyl-5-[(1-ethylpropyl)amino]pyrazin-2-yl}-5,6,7,8-tetrahydronaphthalen-2-yl trifluoromethanesulfonate (100 mg 0.2 mmol), 1,3-diphenylphosphinopropane (1.65 mg, 0.004 mmol), Pd(AcO)$_2$ (0.9 mg, 0.004 mmol), and DMF (0.5 mL). The reaction was heated to 60° C. on the orbital shaker. Triethyl silane (0.08 mL, 0.5 mmol) was added at once. A color change from yellow to dark orange was observed. The vial was re-sealed with a teflon lined cap and heated to 60° C. for 2 hours. After cooling to ambient temperature, the reaction was diluted with ethyl acetate, poured in $H_2O$, washed once with sat. aq. $NaHCO_3$ and once with Brine. The organic layer was dried with $Na_2SO_4$, filtered and concentrated to 120 mg of a crude oil. The crude was purified by Biotage MPLC (40 g column, toluene) to give 53 mg (76%) of 3,6-diethyl-N-(1-ethylpropyl)-5-(5,6,7,8-tetrahydronaphthalen-2-yl)pyrazin-2-amine as a clear oil. Rf 0.18 (toluene). IR (liq.) 2964, 2933, 2874, 2858, 2837, 1558, 1508, 1483, 1463, 1444, 1392, 1381, 1212, 1173, 833 cm$^{-1}$. OAMS supporting ions at: ESI+352.2. Anal. Calcd for $C_{23}H_{33}N_3$: C, 78.58; H, 9.46; N, 11.95. Found: C, 78.20; H, 9.25; N, 11.95.

Example 10

5-(3-chloro-5,6,7,8-tetrahydronaphthalen-2-yl)-3,6-diethyl-N-(1-ethylpropyl)pyrazin-2-amine

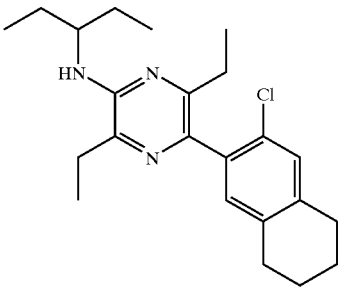

Step 1: 5-(3-amino-5,6,7,8-tetrahydronaphthalen-2-yl)-3,6-diethyl-N-(1-ethylpropyl)pyrazin-2-amine A dry 20 mL vial with a teflon lined cap was charged with 3-{3,6-diethyl-5-[(1-ethylpropyl)amino]pyrazin-2-yl}-5,6,7,8-tetrahydronaphthalen-2-yl trifluoromethanesulfonate (Example 8, 1.0 g, 2.0 mmol), dioxane (10 mL), 2,2'-Bis(diphenylphophino)-1,1'-binaphthyl (BINAP, 112.1 mg, 0.18 mmol), Pd(OAc)$_2$ (27 mg, 0.12 mmol), and CsCO$_3$ (1.95 g, 6 mmol). The reaction was heated to 100° C. on an orbital shaker for 40 hours. After cooling to ambient temperature, the reaction was poured into H$_2$O and extracted twice with ethyl acetate. The organics were combined, dried with Na$_2$SO$_4$, filtered and concentrated to give 2.18 g of a brown crude oil. The crude was dissolved in solution of THF (40 mL) and 2 N aq. HCl (2 mL). A precipitate formed immediately. After stirring the mixture at ambient temperature for 20 minutes, it was diluted with 0.5 M aq. HCl (100 mL) and extracted with a solution of heptane:ethyl acetate (2:1). The aqueous solution was basified with 1N aq. NaOH and extracted with CH$_2$Cl$_2$ which was dried with MgSO$_4$, filtered and concentrated to 225 mg of a crude brown oil. This material was purified twice by Biotage (40 G plus SIM) using 20% ethyl acetate) to give 120 mg (16%) of 5-(3-amino-5,6,7,8-tetrahydronaphthalen-2-yl)-3,6-diethyl-N-(1-ethylpropyl)pyrazin-2-amine as a dark oil.

Step 2: 5-(3-chloro-5,6,7,8-tetrahydronaphthalen-2-yl)-3,6-diethyl-N-(1-ethylpropyl)pyrazin-2-amine A 50 mL round bottom flask equipped with a magnetic stir bar was charged with 5-(3-amino-5,6,7,8-tetrahydronaphthalen-2-yl)-3,6-diethyl-N-(1-ethylpropyl)pyrazin-2-amine (118 mg, 0.32 mmol), con. HCl (3.41 mL) and cooled with an ice bath for 30 minutes. The solution was yellow. A cold solution of NaNO$_2$ (22.4 mg, 0.325 mmol) in H$_2$O (0.64 mL) was added and the mixture stirred at 0° C. for 30 minutes. A light precipitate was observed. A cold CuCl (38.2 mg, 0.386 mmol) solution in con. HCl (0.853 mL) was added and the mixture continued to stir at 0° C. for 20 minutes. The reaction turned dark. The cooling bath was removed, and after stirring at ambient temperature for 2 hours the color lightened and gas evolution was observed. The reaction was then heated to 60° C. for 20 minutes. More gas evolution was observed. After heating the reaction became clumpy. It was cooled with an ice bath and basified with aq. NaOH. The reaction turned blue/green in color. The now basic reaction mixture was diluted with water, extracted three times with CH$_2$Cl$_2$, the organics were combined, dried with Na$_2$SO$_4$, filtered and concentrated to 110 mg of a crude brown oil. PREP TLC followed by silica gel chromatography (4.5 g) using toluene gave 4.45 mg (4%) of 5-(3-chloro-5,6,7,8-tetrahydronaphthalen-2-yl)-3,6-diethyl-N-(1-ethylpropyl)pyrazin-2-amine as a yellow oil. Rf 0.16 (toluene). OAMS supporting ions at: ESI+386.1. HRMS (ESI) calcd for C$_{23}$H$_{32}$N$_3$CL+H$_1$ 386.2363, found 386.2358.

Example 11

3,6-diethyl-5-(6-methoxy-2,3-dihydro-1H-inden-5-yl)-N-[2-methoxy-1-(methoxymethyl)ethyl]pyrazin-2-amine

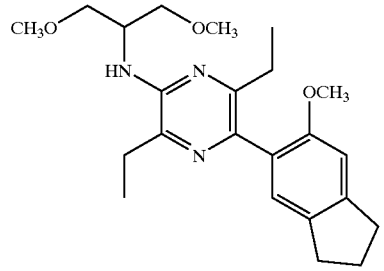

Step 1: 3,6-diethyl-N-[2-methoxy-1-(methoxymethyl)ethyl]pyrazin-2-amine

Following the general procedure of Example 1 Step 1 and making non-critical variations but substituting 1-ethyl propylamine with 1,3-dimethoxy-2-aminopropane (715 mg, 6 mmol) gave 1.34 g of a dark crude oil. This material was purified by Biotage MPLC (90 g column, 10% ethyl acetate in heptane) to give 450 mg (60%) of 3,6-diethyl-N-[2-methoxy-1-(methoxymethyl)ethyl]pyrazin-2-amine as a pale yellow oil.

Step 2: 5-bromo-3,6-diethyl-N-[2-methoxy-1-(methoxymethyl)ethyl]pyrazin-2-amine

Following the general procedure of Example 1 Step 2 and making non-critical variations but substituting 3,6-diethyl-N-(1-ethylpropyl)pyrazin-2-amine with 3,6-diethyl-N-[2-methoxy-1-(methoxymethyl)ethyl]pyrazin-2-amine (445 mg, 1.76 mmol) gave 610 mg of an orange crude oil. This material was purified by Biotage MPLC (90 g column, 10% ethyl acetate in heptane) to give 435 mg (75%) of 5-bromo-3,6-diethyl-N-[2-methoxy-1-(methoxymethyl)ethyl]pyrazin-2-amine as a pale yellow oil.

Step 3: 3,6-diethyl-5-(6-methoxy-2,3-dihydro-1H-inden-5-yl)-N-[2-methoxy-1-(methoxymethyl)ethyl]pyrazin-2-amine Following the general procedure of Example 1 Step 3), and making non-critical variations but substituting 5-bromo-3,6-diethyl-N-(1-ethylpropyl)pyrazin-2-amine with 5-bromo-3,6-diethyl-N-[2-methoxy-1-(methoxymethyl)ethyl]pyrazin-2-amine (214 mg, 0.644 mmol) gave 350 mg of an orange crude oil. This material was purified by Biotage MPLC (40 g column, 7% acetone in heptane) to give 68 mg (26%) of 3,6-diethyl-5-(6-methoxy-2,3-dihydro-1H-inden-5-yl)-N-[2-methoxy-1-(methoxymethyl)ethyl]pyrazin-2-amine as a pale yellow oil. Rf 0.15 (7% acetone in toluene). IR (diffuse reflectance) 2957, 2930, 2886, 1562, 1482, 1458, 1449, 1391, 1385, 1254, 1194, 1174, 1165, 1113, 1086 cm$^{-1}$. OAMS supporting ions at: ESI+400.3 HRMS (ESI) calcd for C$_{23}$H$_{33}$N$_3$O$_3$+H$_1$ 400.2600, found 400.2594. Anal. Calcd for C$_{23}$H$_{33}$N$_3$O$_3$: C, 69.14; H, 8.33; N, 10.52. Found: C, 68.76; H, 8.39; N, 10.49.

Example 12

3,6-diethyl-5-(6-methoxy-2,3-dihydro-1H-inden-5-yl)-N-[(1R)-1-(methoxymethyl)propyl]pyrazin-2-amine

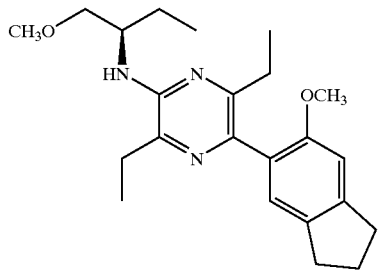

Step 1: (2R)-2-[(3,6-diethylpyrazin-2-yl)amino]butan-1-ol

Following the general procedure of Example 1 Step 1, and making non-critical variations but substituting 1-ethyl propylamine with (R)-(−)-2-amino-1-butanol (1.88 mL, 20 mmol) gave 3.35 g of a dark crude oil. This material was purified by Biotage MPLC (120 g column, 20–100% ethyl acetate in heptane gradient) to give 520 mg (23%) of (2R)-2-[(3,6-diethylpyrazin-2-yl)amino]butan-1-ol as a pale yellow oil. Rf 0.08 (20% ethyl acetate in heptane).

Step 2: (2R)-2-[(5-bromo-3,6-diethylpyrazin-2-yl)amino]butan-1-ol

Following the general procedure of Example 1 Step 2), and making non-critical variations but substituting 3,6-diethyl-N-(1-ethylpropyl)pyrazin-2-amine with (2R)-2-[(3,6-diethylpyrazin-2-yl)amino]butan-1-ol (515 mg, 2.30 mmol) gave 780 mg of an ivory solid. This material was purified by Biotage MPLC (90 g column, 20% ethyl acetate in heptane) to give 731 mg (contains heptane) of (2R)-2-[(5-bromo-3,6-diethylpyrazin-2-yl)amino]butan-1-ol as an ivory solid. Rf 0.12 (20% ethyl acetate in heptane).

Step 3: 5-bromo-3,6-diethyl-N-[(1R)-1-(methoxymethyl)propyl]pyrazin-2-amine

Following the general procedure of Example 13 Step 3 and making non-critical variations but substituting (2S)-2-[(5-bromo-3,6-diethylpyrazin-2-yl)amino]butan-1-ol with (2R)-2-[(5-bromo-3,6-diethylpyrazin-2-yl)amino]butan-1-ol (353 mg, 1.17 mmol) gave 780 mg of a crude oil. This material was purified by Biotage MPLC (90 g column, 10–20% ethyl acetate in heptane gradient) to give 250 mg (67%) of 5-bromo-3,6-diethyl-N-[(1R)-1-(methoxymethyl)propyl]pyrazin-2-amine as a yellow oil.

Step 4: 3,6-diethyl-5-(6-methoxy-2,3-dihydro-1H-inden-5-yl)-N-[(1R)-1-(methoxymethyl)propyl]pyrazin-2-amine Following the general procedure of Example 1 Step 3, and making non-critical variations but substituting 5-bromo-3,6-diethyl-N-(1-ethylpropyl)pyrazin-2-amine with 5-bromo-3,6-diethyl-N-[(1R)-1-(methoxymethyl)propyl]pyrazin-2-amine (250 mg, 0.79 mmol) and gave 510 mg of a yellow crude oil. This material was purified by Biotage MPLC (120 g, 2% acetone in toluene) to give 237 mg (78%) of 3,6-diethyl-5-(6-methoxy-2,3-dihydro-1H-inden-5-yl)-N-[(1R)-1-(methoxymethyl)propyl]pyrazin-2-amine as a yellow oil. Rf 0.27 (20% ethyl acetate in heptane). IR (liq.) 2965, 2935, 2890, 2875, 1566, 1551, 1498, 1484, 1465, 1447, 1391, 1253, 1200, 1173, 1109 cm$^{-1}$. OAMS supporting ions at: ESI+384.3. HRMS (ESI) calcd for $C_{23}H_{33}N_3O_2+H_1$ 384.2651, found 384.2642.

Example 13

N-[(1S)-1-(ethoxymethyl)propyl]-3,6-diethyl-5-(6-methoxy-2,3-dihydro-1H-inden-5-yl)pyrazin-2-amine

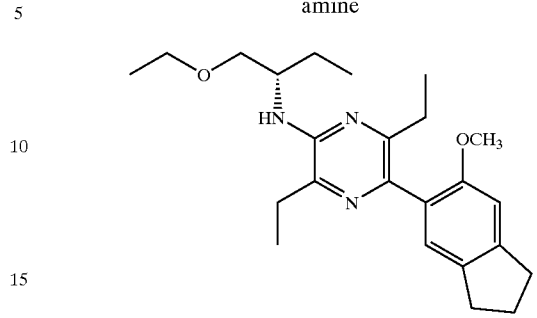

Step 1: (2S)-2-[(3,6-diethylpyrazin-2-yl)amino]butan-1-ol

Following the general procedure of Example 1 Step 1 and making non-critical variations but substituting 1-ethyl propylamine with (S)-(+)-2-amino-1-butanol (2.82 mL, 30 mmol) gave 4.25 g of a dark crude oil. This material was purified by Biotage MPLC (120 g column, 20–50% ethyl acetate in heptane gradient) to give 968 mg (29%) of (2S)-2-[(3,6-diethylpyrazin-2-yl)amino]butan-1-ol as a pale yellow oil.

Step 2: (2S)-2-[(5-bromo-3,6-diethylpyrazin-2-yl)amino]butan-1-ol

Following the general procedure of Example 1 Step 2 and making non-critical variations but substituting 3,6-diethyl-N-(1-ethylpropyl)pyrazin-2-amine with (2S)-2-[(3,6-diethylpyrazin-2-yl)amino]butan-1-ol (960 mg, 4.30 mmol) gave 1.39 g of a yellow solid. This material was purified by Biotage MPLC (90 g column, 20% ethyl acetate in heptane) to give 1.075 g (83%) of (2S)-2-[(5-bromo-3,6-diethylpyrazin-2-yl)amino]butan-1-ol as a white solid. Rf 0.12 (20% ethyl acetate in heptane).

Step 3: 5-bromo-N-[(1S)-1-(ethoxymethyl)propyl]-3,6-diethylpyrazin-2-amine

A dry 50 mL round bottom flask was charged with a solution of (2S)-2-[(5-bromo-3,6-diethylpyrazin-2-yl)amino]butan-1-ol (356 mg, 1.18 mmol) in DMF (12 mL). NaH (70.8 mg, 1.77 mmol) was added to the homogeneous solution. Effervescence was observed and the solution turned cloudy. Iodoethane (0.189 mL, 2.36 mmol) was added at once. The now yellow solution was stirred at ambient temperature for 20 minutes. The same quantities of NaH and iodoethane were added to the reaction mixture two more times in the same manner. The reaction was quenched with water and extracted twice with ethyl acetate. The organics were combined, dried with $Na_2SO_4$, filtered and concentrated to give 510 mg of a crude yellow oil. This material was purified by Biotage MPLC (90 g column, using 5% ethyl acetate in heptane) to give 193 mg (50%) of 5-bromo-N-[(1S)-1-(ethoxymethyl)propyl]-3,6-diethylpyrazin-2-amine as a yellow oil. Rf 0.16 (5% ethyl acetate in heptane).

Step 4: N-[(1S)-1-(ethoxymethyl)propyl]-3,6-diethyl-5-(6-methoxy-2,3-dihydro-1H-inden-5-yl)pyrazin-2-amine Following the general procedure of Example 1 Step 3 and making non-critical variations but substituting 5-bromo-3,6-diethyl-N-(1-ethylpropyl)pyrazin-2-amine with 5-bromo-N-[(1S)-1-(ethoxymethyl)propyl]-3,6-diethylpyrazin-2-amine (83 mg, 0.25 mmol) gave 240 mg of a yellow crude oil. This material was purified by Biotage MPLC (40 g column, 2% acetone in toluene) to give 48 mg (48%) of N-[(1S)-1-(ethoxymethyl)propyl]-3,6-diethyl-5-(6-methoxy-2,3-dihydro-1H-inden-5-yl)pyrazin-2-amine as a yellow oil. Rf 0.26 (20% ethyl acetate in heptane). OAMS supporting ions at: ESI+398.3. HRMS (ESI) calcd for $C_{24}H_{35}N_3O_2+H_1$ 398.2807, found 398.2813.

Example 14

3,6-diethyl-N-{(1S)-1-[(2-fluoroethoxy)methyl]propyl}-5-(6-methoxy-2,3-dihydro-1H-inden-5-yl)pyrazin-2-amine

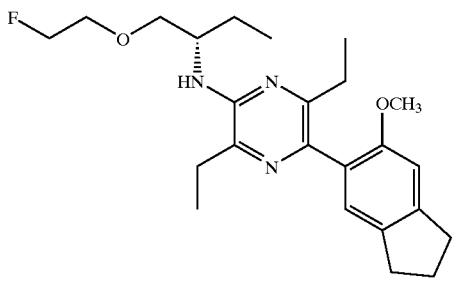

Step 1: 5-bromo-3,6-diethyl-N-{(1S)-1-[(2-fluoroethoxy)methyl]propyl}pyrazin-2-amine Following the general procedure of Example 1 Step 3 and making non-critical variations but substituting iodoethane with 1-bromo-2-fluoroethane, the reaction was carried out on (2S)-2-[(5-bromo-3,6-diethylpyrazin-2-yl)amino]butan-1-ol (356 mg, 1.18 mmol) and gave 546 mg of a crude yellow oil. This material was purified by Biotage MPLC (90 g column, 10% ethyl acetate in heptane) to give 266 mg (65%) of 5-bromo-3,6-diethyl-N-{(1S)-1-[(2-fluoroethoxy)methyl]propyl}pyrazin-2-amine.

Step 2: 3,6-diethyl-N-{(1S)-1-[(2-fluoroethoxy)methyl]propyl}-5-(6-methoxy-2,3-dihydro-1H-inden-5-yl)pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-{(1S)-1-[(2-fluoroethoxy)methyl]propyl}pyrazin-2-amine (100 mg, 0.287 mmol) and gave 240 mg of a yellow crude oil. This material was purified by Biotage MPLC (40 g column, using 2% acetone in toluene) to give 74 mg (62%) of 3,6-diethyl-N-{(1S)-1-[(2-fluoroethoxy)methyl]propyl}-5-(6-methoxy-2,3-dihydro-1H-inden-5-yl)pyrazin-2-amine. Rf 0.16 (20% ethyl acetate in heptane). OAMS supporting ions at: ESI+416.3. HRMS (ESI) calcd for $C_{24}H_{34}FN_3O_2+H_1$ 416.2713, found 416.2710.

Example 15

3,6-diethyl-5-(6-methoxy-2,3-dihydro-1H-inden-5-yl)-N-[(1R)-1-phenylethyl]pyrazin-2-amine

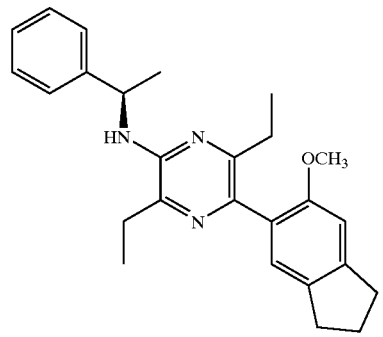

Step 1: 3,6-diethyl-N-[(1R)-1-phenylethyl]pyrazin-2-amine

Following the general procedure of Example 1 Step 1 and making non-critical variations but substituting 1-ethyl propylamine with (R)-(+)-α-methylbenzylamine (3.87 mL, 30 mmol) gave 5.62 g of an orange crude oil. This material was purified by Biotage MPLC (120 g column, a 20% ethyl acetate in heptane) to give 3.6 g (89%) of 3,6-diethyl-N-[(1R)-1-phenylethyl]pyrazin-2-amine as a pale yellow oil. Rf 0.25 (20% ethyl acetate in heptane).

Step 2: 5-bromo-3,6-diethyl-N-[(1R)-1-phenylethyl]pyrazin-2-amine

Following the general procedure of Example 1 Step 2 and making non-critical variations but substituting 3,6-diethyl-N-(1-ethylpropyl)pyrazin-2-amine with 3,6-diethyl-N-[(1R)-1-phenylethyl]pyrazin-2-amine (1.08 g mg, 4.2 mmol) gave 1.36 g of an orange solid. This material was purified by Biotage MPLC (90 g column, 5% ethyl acetate in heptane) to give 1.21 g (86%) of 5-bromo-3,6-diethyl-N-[(1R)-1-phenylethyl]pyrazin-2-amine as a pale yellow oil. Rf 0.52 (20% ethyl acetate in heptane).

Step 3: 3,6-diethyl-5-(6-methoxy-2,3-dihydro-1H-inden-5-yl)-N-[(1R)-1-phenylethyl]pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1R)-1-phenylethyl]pyrazin-2-amine (465 mg, 1.39 mmol) gave 920 mg of a yellow crude oil. This material was purified by Biotage MPLC (90 g column, 1.5% acetone in toluene) to give 313 mg (56%) of 3,6-diethyl-5-(6-methoxy-2,3-dihydro-1H-inden-5-yl)-N-[(1R)-1-phenylethyl]pyrazin-2-amine as a yellow oil. Rf 0.37 (2% acetone in heptane). IR (diffuse reflectance) 2964, 2932, 2869, 2840, 1568, 1563, 1550, 1481, 1449, 1385, 1352, 1276, 1252, 1167, 699cm$^{-1}$. OAMS supporting ions at: ESI+402.3. Anal. Calcd for $C_{26}H_{31}N_3O$: C, 77.77; H, 7.78; N, 10.46. Found: C, 77.51; H, 7.76; N, 10.20.

Example 16

3,6-diethyl-5-(6-methoxy-2,3-dihydro-1H-inden-5-yl)-N-[(1S)-1-phenylethyl]pyrazin-2-amine

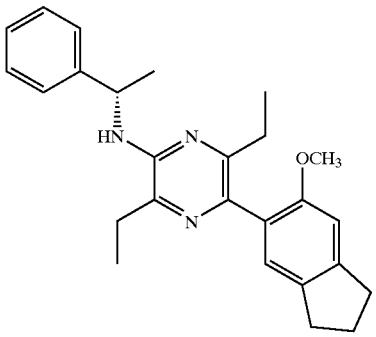

Step 1: 3,6-diethyl-N-[(1S)-1-phenylethyl]pyrazin-2-amine

Following the general procedure of Example 1 Step 1 and making non-critical variations but substituting 1-ethyl propylamine with (S)-(−)-α-methylbenzylamine (1.94 mL, 15 mmol) gave 3.92 g of an orange crude oil. This material was purified by Biotage MPLC (120 g column, a 10% ethyl acetate in heptane) to give 1.81 g (95%) of 3,6-diethyl-N-[(1S)-1-phenylethyl]pyrazin-2-amine as a pale yellow oil.

Step 2: 5-bromo-3,6-diethyl-N-[(1S)-1-phenylethyl]pyrazin-2-amine

Following the general procedure of Example 1 Step 2 and making non-critical variations but substituting 3,6-diethyl-N-(1-ethylpropyl)pyrazin-2-amine with 3,6-diethyl-N-[(1S)-1-phenylethyl]pyrazin-2-amine (1.08 g mg, 4.2 mmol) gave 1.53 g of a yellow oil. This material was purified by Biotage MPLC (90 g column, 5% ethyl acetate in heptane) to give 1.27 g (90%) of 5-bromo-3,6-diethyl-N-[(1S)-1-phenylethyl]pyrazin-2-amine as a yellow oil.

Step 3: 3,6-diethyl-5-(6-methoxy-2,3-dihydro-1H-inden-5-yl)-N-[(1S)-1-phenylethyl]pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1S)-1-phenylethyl]pyrazin-2-amine (232 mg, 0.70 mmol) and gave 460 mg of a yellow crude oil. This material was purified by Biotage MPLC (40 g column, 1.5% acetone in toluene) to give 224 mg (80%) of 3,6-diethyl-5-(6-methoxy-2,3-dihydro-1H-inden-5-yl)-N-[(1S)-1-phenylethyl]pyrazin-2-amine as a yellow oil. Rf 0.28 (2% acetone in heptane). IR (liq.) 2967, 2934, 2871, 1565, 1549, 1480, 1452, 1447, 1386, 1276, 1253, 1202, 1168, 1033, 699 cm$^{-1}$. OAMS supporting ions at: ESI+402.2. HRMS (ESI) calcd for $C_{26}H_{31}N_3O+H_1$ 402.2545, found 402.2542.

Example 17

3,6-diethyl-5-(6-methoxy-2,3-dihydro-1H-inden-5-yl)-N-[(1R)-1-methylpropyl]pyrazin-2-amine

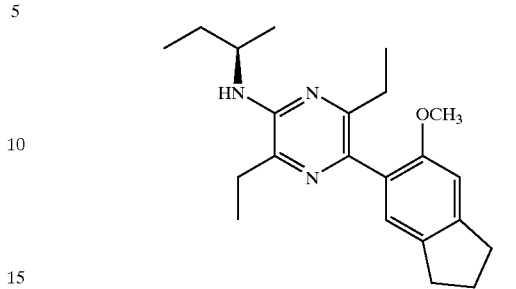

Step 1: 3,6-diethyl-N-[(1R)-1-methylpropyl]pyrazin-2-amine

Following the general procedure of Example 1 Step 1 and making non-critical variations but substituting 1-ethyl propylamine with (R)-(−)-sec-butylamine (1.50 mL, 15 mmol) gave 1.62 g of a very dark crude oil. This material was purified by Biotage MPLC (90 g column, 10% ethyl acetate in heptane) to give 1.19 g (77%) of 3,6-diethyl-N-[(1R)-1-methylpropyl]pyrazin-2-amine as a pale yellow oil. Rf 0.27 (20% ethyl acetate in heptane). IR (liq.) 3453, 3355, 2967, 2935, 2875, 1581, 1546, 1501, 1463, 1446, 1391, 1379, 1352, 1179, 1161 cm$^{-1}$. OAMS supporting ions at: ESI+ 208.3. HRMS (ESI) calcd for $C_{12}H_{21}N_3+H_1$ 208.1814, found 208.1811. $[\alpha]^{25}_D = -25°$ (c 1.01, ethanol). Anal. Calcd for $C_{12}H_{21}N_3$: C, 69.52; H, 10.21; N, 20.27. Found: C, 69.62; H, 10.13; N, 19.65.

Step 2: 5-bromo-3,6-diethyl-N-[(1R)-1-methylpropyl]pyrazin-2-amine

Following the general procedure of Example 1 Step 2 and making non-critical variations but substituting 3,6-diethyl-N-(1-ethylpropyl)pyrazin-2-amine with 3,6-diethyl-N-[(1R)-1-methylpropyl]pyrazin-2-amine (0.988 g, 4.8 mmol) gave 1.59 g of an orange oil. This material was purified by Biotage MPLC (90 g column, 5% ethyl acetate in heptane) to give 1.20 g (88%) of 5-bromo-3,6-diethyl-N-[(1R)-1-methylpropyl]pyrazin-2-amine as a yellow oil. Rf 0.35 (12% ethyl acetate in heptane). IR (liq.) 3436, 2969, 2935, 2876, 1560, 1541, 1483, 1462, 1447, 1417, 1392, 1380, 1243, 1180, 1166 cm$^{-1}$. $[\alpha]^{25}_D = -22°$ (c 0.98, ethanol). Anal. Calcd for $C_{12}H_{20}BrN_3$: C, 50.36; H, 7.04; N, 14.68; Br, 27.92. Found: C, 50.29; H, 7.09; N, 14.60. Step 3: 3,6-diethyl-5-(6-methoxy-2,3-dihydro-1H-inden-5-yl)-N-[(1R)-1-methylpropyl]pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1R)-1-methylpropyl]pyrazin-2-amine (286 mg, 1.0 mmol) and gave 620 mg of a yellow crude oil. This material was purified by Biotage MPLC (90 g column, 1.5% acetone in toluene) to give 286 mg (81%) of 3,6-diethyl-5-(6-methoxy-2,3-dihydro-1H-inden-5-yl)-N-[(1R)-1-methylpropyl]pyrazin-2-amine as a yellow oil. Rf 0.25 (2% acetone in heptane). IR (liq.) 2965, 2935, 2874, 2844, 1566, 1550, 1484, 1464, 1447, 1389, 1276, 1253, 1203, 1176, 1164 cm$^{-1}$. OAMS supporting ions at: ESI+354.2. HRMS (ESI) calcd for $C_{22}H_{31}N_3O+H_1$ 354.2545, found 354.2554. $[\alpha]^{25}_D = -19$ (c 0.57, ethanol). Anal. Calcd for $C_{22}H_{31}N_3O$: C, 74.75; H, 8.84; N, 11.89. Found: C, 74.41; H, 8.84; N, 11.65.

Example 18

3,6-diethyl-5-(6-methoxy-2,3-dihydro-1H-inden-5-yl)-N-[(1S)-1-methylpropyl]pyrazin-2-amine

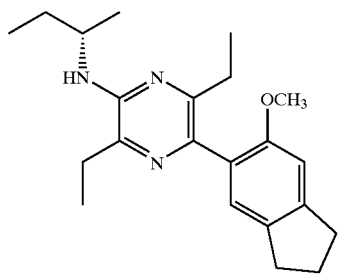

Step 1: 3,6-diethyl-N-[(1S)-1-methylpropyl]pyrazin-2-amine

Following the general procedure of Example 1 Step 1 and making non-critical variations but substituting 1-ethyl propylamine with (S)-(+)-sec-butylamine (1.50 mL, 15 mmol) gave 1.82 g of a very dark crude oil. This material was purified by Biotage MPLC (90 g column, 10% ethyl acetate in heptane) to give 1.18 g (77%) of 3,6-diethyl-N-[(1S)-1-methylpropyl]pyrazin-2-amine as an orange oil. Rf 0.27 (20% ethyl acetate in heptane). IR (liq.) 3453, 3362, 2967, 2936, 2876, 1581, 1546, 1501, 1463, 1447, 1391, 1379, 1351, 1179, 1161 cm$^{-1}$. OAMS supporting ions at: ESI+ 208.3. HRMS (ESI) calcd for $C_{12}H_{21}N_3+H_1$ 208.1814, found 208.1811. $[\alpha]^{25}_D$=24SYMBOL 176 (c 0.97, ethanol). Anal. Calcd for $C_{12}H_{21}N_3$: C, 69.52; H, 10.21; N, 20.27. Found: C, 69.30; H, 9.82; N, 19.63.

Step 2: 5-bromo-3,6-diethyl-N-[(1S)-1-methylpropyl]pyrazin-2-amine

Following the general procedure of Example 1 Step 2 and making non-critical variations but substituting 3,6-diethyl-N-(1-ethylpropyl)pyrazin-2-amine with 3,6-diethyl-N-[(1S)-1-methylpropyl]pyrazin-2-amine (0.99 g, 4.76 mmol) gave 1.44 g of a yellow oil. This material was purified by Biotage MPLC (90 g column, 5% ethyl acetate in heptane) to give 1.23 g (90%) of 5-bromo-3,6-diethyl-N-[(1S)-1-methylpropyl]pyrazin-2-amine as a yellow oil. Rf 0.35 (12% ethyl acetate in heptane). IR (liq.) 3436, 2968, 2935, 2876, 1560, 1541, 1483, 1462, 1447, 1417, 1392, 1380, 1243, 1180, 1165 cm$^1$. $[\alpha]^{25}_D$=22° (c 1.15, ethanol). Anal. Calcd for $C_{12}H_{20}BrN_3$: C, 50.36; H, 7.04; N, 14.68; Br, 27.92. Found: C, 50.10; H, 7.11; N, 14.71.

Step 3: 3,6-diethyl-5-(6-methoxy-2,3-dihydro-1H-inden-5-yl)-N-[(1S)-1-methylpropyl]pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1S)-1-methylpropyl]pyrazin-2-amine (287 mg, 1.0 mmol) and gave 540 mg of an orange crude oil. This material was purified by Biotage MPLC (90 g column, 1.5% acetone in toluene) to give 283 mg (80%) of 3,6-diethyl-5-(6-methoxy-2,3-dihydro-1H-inden-5-yl)-N-[(1S)-1-methylpropyl]pyrazin-2-amine as a yellow oil. Rf 0.25 (2% acetone in heptane). IR (liq.) 2964, 2934, 2873, 1566, 1550, 1498, 1484, 1464, 1446, 1389, 1276, 1253, 1203, 1176, 1164 cm$^{-1}$. OAMS supporting ions at: ESI+354.3. HRMS (ESI) calcd for $C_{22}H_{31}N_3O+H_1$ 354.2545, found 354.2544.

Example 19

N-cyclopentyl-3,6-diethyl-5-(6-methoxy-2,3-dihydro-1H-inden-5-yl)pyrazin-2-amine

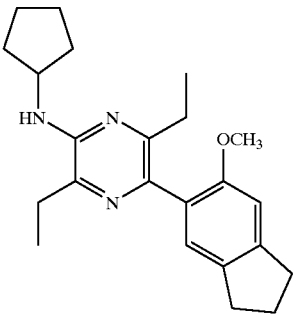

Step 1: N-cyclopentyl-3,6-diethylpyrazin-2-amine

Following the general procedure of Example 1 Step 1 and making non-critical variations but substituting 1-ethyl propylamine with cyclopentylamine (1.48 mL, 15 mmol) gave 1.73 g of a very dark crude oil. This material was purified by Biotage MPLC (120 g column, 10% ethyl acetate in heptane) to give 1.11 g (68%) of N-cyclopentyl-3,6-diethylpyrazin-2-amine as a pale yellow oil. Rf 0.27 (20% ethyl acetate in heptane). IR (liq.) 3453, 2966, 2938, 2872, 1581, 1545, 1498, 1464, 1446, 1392, 1349, 1267, 1186, 1169, 1150 cm$^{-1}$. OAMS supporting ions at: ESI+220.3. HRMS (ESI) calcd for $C_{13}H_{21}N_3+H_1$ 220.1814, found 220.1813. Anal. Calcd for $C_{13}H_{21}N_3$: C, 71.19; H, 9.65; N, 19.16. Found: C, 71.05; H, 9.66; N, 18.53.

Step 2: 5-bromo-N-cyclopentyl-3,6-diethylpyrazin-2-amine

Following the general procedure of Example 1 Step 2 and making non-critical variations but substituting 3,6-diethyl-N-(1-ethylpropyl)pyrazin-2-amine with N-cyclopentyl-3,6-diethylpyrazin-2-amine (1.00 g, 4.56 mmol) gave 1.63 g of a dark brown oil. This material was purified by Biotage MPLC (90 g column, 5% ethyl acetate in heptane) to give 1.23 g (90%) of 5-bromo-N-cyclopentyl-3,6-diethylpyrazin-2-amine as an orange oil. Rf 0.60 (20% ethyl acetate in heptane). IR (liq.) 3439, 2967, 2938, 2872, 1560, 1540, 1480, 1463, 1447, 1416, 1392, 1348, 1242, 1192, 1174 cm$^{-1}$. OAMS supporting ions at: ESI+300.0. Anal. Calcd for $C_{13}H_{20}BrN_3$: C, 52.36; H, 6.76; N, 14.09; Br, 26.79. Found: C, 52.22; H, 6.94; N, 14.07.

Step 3: N-cyclopentyl-3,6-diethyl-5-(6-methoxy-2,3-dihydro-1H-inden-5-yl)pyrazin-2-amine Following the general procedure of Example 1 Step 3 and making non-critical variations but substituting 5-bromo-3,6-diethyl-N-(1-ethylpropyl)pyrazin-2-amine with 5-bromo-N-cyclopentyl-3,6-diethylpyrazin-2-amine (298 mg, 1.0 mmol) and gave 710 mg of a yellow crude oil. This material was purified by Biotage MPLC (90 g column, 1.5% acetone in toluene) to give 324 mg (89%) of N-cyclopentyl-3,6-diethyl-5-(6-methoxy-2,3-dihydro-1H-inden-5-yl)pyrazin-2-amine. Rf 0.24 (1.5% acetone in toluene). IR (diffuse reflectance) 3378, 2957, 2934, 2874, 1569, 1497, 1483, 1458, 1436, 1390, 1348, 1250, 1201, 1188, 1171 cm$^{-1}$. OAMS supporting ions at: ESI+366.3. HRMS (ESI) calcd for $C_{23}H_{31}N_3O+H_1$ 366.2545, found 366.2555.

Example 20

N-(dicyclopropylmethyl)-3,6-diethyl-5-(6-methoxy-2,3-dihydro-1H-inden-5-yl)pyrazin-2-amine

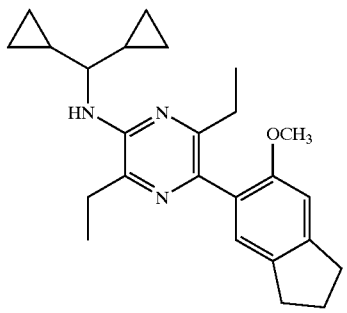

Step 1: N-(dicyclopropylmethyl)-3,6-diethylpyrazin-2-amine

Following the general procedure of Example 1 Step 1 and making non-critical variations but substituting 1-ethyl propylamine with dicyclopropylmethylamine hydrochloride (2.21 g, 15 mmol) gave 1.82 g of a very dark crude oil. This material was purified by Biotage MPLC (120 g column, 8% ethyl acetate in heptane) to give 1.29 g (70%) of N-(dicyclopropylmethyl)-3,6-diethylpyrazin-2-amine as a pale yellow oil. Rf 0.08 (5% ethyl acetate in heptane). IR (liq.) 3006, 2970, 2936, 2875, 1580, 1545, 1497, 1465, 1446, 1395, 1378, 1169, 1155, 1045, 1018 $cm^{-1}$. OAMS supporting ions at: ESI+246.3. HRMS (ESI) calcd for $C_{15}H_{23}N_3+H_1$ 246.1970, found 246.1966. Anal. Calcd for $C_{15}H_{23}N_3$: C, 73.43; H1 9.45; N, 17.13. Found: C, 73.37; H, 9.43; N, 16.72.

Step 2: 5-bromo-N-(dicyclopropylmethyl)-3,6-diethylpyrazin-2-amine

Following the general procedure of Example 1 Step 2 and making non-critical variations but substituting 3,6-diethyl-N-(1-ethylpropyl)pyrazin-2-amine with N-(dicyclopropylmethyl)-3,6-diethylpyrazin-2-amine (0.959 g, 3.9 mmol) gave 1.34 g of a dark brown oil. This material was purified by Biotage MPLC (90 g column, 2.5% ethyl acetate in heptane) to give 0.75 g (59%) of 5-bromo-N-(dicyclopropylmethyl)-3,6-diethylpyrazin-2-amine as a yellow oil. Rf 0.45 (10% ethyl acetate in heptane). IR (liq.) 3005, 2973, 2936, 1560, 1539, 1481, 1462, 1448, 1431, 1417, 1391, 1375, 1176, 1158, 1019 $cm^{-1}$. OAMS supporting ions at: ESI+324.1. HRMS (ESI) calcd for $C_{15}H_{22}N_3Br+H_1$ 324.1076, found 324.1066. Anal. Calcd for $C_{15}H_{22}BrN_3$: C, 55.56; H, 6.84; N, 12.96; Br, 24.64. Found: C, 55.49; H, 6.90; N, 12.76.

Step 3: N-(dicyclopropylmethyl)-3,6-diethyl-5-(6-methoxy-2,3-dihydro-1H-inden-5-yl)pyrazin-2-amine Following the general procedure of Example 1 Step 3 and making non-critical variations but substituting 5-bromo-3,6-diethyl-N-(1-ethylpropyl)pyrazin-2-amine with 5-bromo-N-(dicyclopropylmethyl)-3,6-diethylpyrazin-2-amine (324 mg, 1.0 mmol) and gave 690 mg of a yellow crude oil. This material was purified by Biotage MPLC (90 g column, 1.5% acetone in toluene) to give 147 mg (38%) of N-(dicyclopropylmethyl)-3,6-diethyl-5-(6-methoxy-2,3-dihydro-1H-inden-5-yl)pyrazin-2-amine. Rf 0.27 (1.5% acetone in toluene). OAMS supporting ions at: ESI+392.1. IR (liq.) 3002, 2964, 2935, 1565, 1550, 1482, 1465, 1447, 1388, 1276, 1253, 1203, 1164, 1031, 1019 $cm^{-1}$. OAMS supporting ions at: ESI+392.1 Anal. Calcd for $C_{25}H_{33}N_3O$: C, 76.69; H, 8.49; N, 10.73. Found: C, 76.63; H, 8.55; N, 10.40.

Example 21

3,6-diethyl-5-(6-methoxy-2,3-dihydro-1H-inden-5-yl)-N-(1-methylbutyl)pyrazin-2-amine

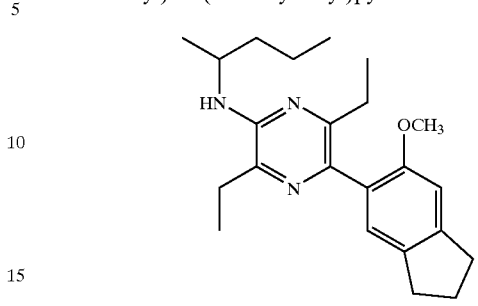

Step 1: 3,6-diethyl-N-(1-methylbutyl)pyrazin-2-amine

Following the general procedure of Example 1 Step 1 and making non-critical variations but substituting 1-ethyl propylamine with 2-pentylamine (1.31 g, 15 mmol) gave 2.09 g of a dark crude oil. This material was purified by Biotage MPLC (120 g column, gradient of 5–10% ethyl acetate in heptane) to give 1.32 g (80%) of 3,6-diethyl-N-(1-methylbutyl)pyrazin-2-amine as a pale yellow oil. Rf 0.08 (5% ethyl acetate in heptane). IR (liq.) 2966, 2934, 2873, 1581, 1545, 1501, 1466, 1446, 1390, 1379, 1267, 1236, 1177, 1160, 863$cm^{-1}$. OAMS supporting ions at: ESI+222.3. Anal. Calcd for $C_{13}H_{23}N_3$: C, 70.54; H, 10.47; N, 18.98. Found: C, 70.51; H, 10.10; N, 18.64.

Step 2: 5-bromo-3,6-diethyl-N-(1-methylbutyl)pyrazin-2-amine

Following the general procedure of Example 1 Step 2 and making non-critical variations but substituting 3,6-diethyl-N-(1-ethylpropyl)pyrazin-2-amine with 3,6-diethyl-N-(1-methylbutyl)pyrazin-2-amine (1.29 g, 5.8 mmol) gave 1.90 g of a yellow oil. This material was purified by Biotage MPLC (90 g column, 5% ethyl acetate in heptane) to give 1.61 g (92%) of 5-bromo-3,6-diethyl-N-(1-methylbutyl)pyrazin-2-amine, as a yellow oil. Rf 0.28 (5% ethyl acetate in heptane). IR (liq.) 2967, 2935, 2874, 1560, 1540, 1483, 1465, 1448, 1417, 1392, 1379, 1243, 1178, 1166, 1027 $cm^{-1}$. Anal. Calcd for $C_{13}H_{22}BrN_3$: C, 52.01; H, 7.39; N, 14.00; Br, 26.61. Found: C, 51.96; H, 7.40; N, 13.86.

Step 3: 3,6-diethyl-5-(6-methoxy-2,3-dihydro-1H-inden-5-yl)-N-(1-methylbutyl)pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-(1-methylbutyl)pyrazin-2-amine (300 mg, 1.0 mmol) and gave 510 mg of an orange crude oil. This material was purified by Biotage MPLC (90 g column, 1.5% acetone in toluene) to give 292 mg (79%) of 3,6-diethyl-5-(6-methoxy-2,3-dihydro-1H-inden-5-yl)-N-(1-methylbutyl)pyrazin-2-amine as a yellow oil. Rf 0.21 (1.5% acetone in toluene). IR (liq.) 2960, 2934, 2871, 2844, 1566, 1550, 1498, 1484, 1466, 1447, 1389, 1276, 1253, 1203, 1175 $cm^{-1}$. OAMS supporting ions at: ESI+368.2. HRMS (ESI) calcd for $C_{23}H_{33}N_3O+H_1$ 368.2702, found 368.2695. Anal. Calcd for $C_{23}H_{33}N_3O$: C, 75.16; H, 9.05; N, 11.43. Found: C, 74.80; H, 8.76; N, 10.89.

Example 22

(1R,2S)-1-{[3,6-diethyl-5-(3-methoxy-5,6,7,8-tetrahydronaphthalen-2-yl)pyrazin-2-yl]amino}-2,3-dihydro-1H-inden-2-ol

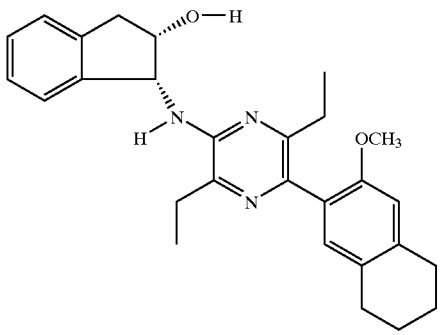

Following the general procedure of Example 1 Step 3 and making non-critical variations but substituting 6-methoxy-2,3-dihydro-1H-inden-5-ylboronic acid (Preparation 2) with 3-methoxy-5,6,7,8-tetrahydronaphthalen-2-ylboronic acid (Preparation 1), and substituting 5-bromo-3,6-diethyl-N-(1-ethylpropyl)pyrazin-2-amine with (1R,2S)-1-[(5-bromo-3,6-diethylpyrazin-2-yl)amino]indan-2-ol (303 mg, 0.84 mmol) and gave 550 mg of a crude orange oil. The crude was purified on a Biotage MPLC column (90 g column, 18% ethyl acetate in heptane) to give 249 mg (67%) of (1R,2S)-1-{[3,6-diethyl-5-(3-methoxy-5,6,7,8-tetrahydronaphthalen-2-yl)pyrazin-2-yl]amino}-2,3-dihydro-1H-inden-2-ol as a glassy paste. Rf 0.20 (25% ethyl acetate in heptane). OAMS supporting ions at: ESI+444.3. HRMS (ESI) calcd for $C_{28}H_{33}N_3O_2+H_1$ 444.2651, found 444.2635.

Example 23

3,6-diethyl-N-[(1R,2S)-2-(2-fluoroethoxy)-2,3-dihydro-1H-inden-1-yl]-5-(3-methoxy-5,6,7,8-tetrahydronaphthalen-2-yl)pyrazin-2-amine

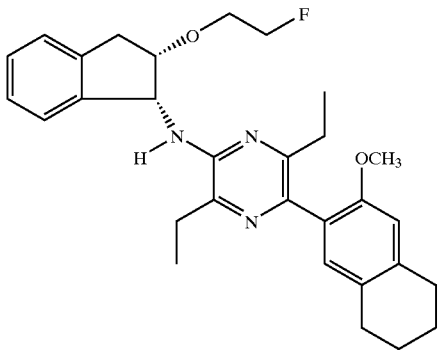

Following the general procedure of Example 13 Step 3 and making non-critical variations but substituting iodoethane with 1-bromo-2-fluoroethane and substituting (2S)-2-[(5-bromo-3,6-diethylpyrazin-2-yl)amino]butan-1-ol with (1R,2S)-1-{[3,6-diethyl-5-(3-methoxy-5,6,7,8-tetrahydronaphthalen-2-yl)pyrazin-2-yl]amino}-2,3-dihydro-1H-inden-2-ol (240 mg, 0.54 mmol) gave 260 mg of a crude yellow paste. This material was purified by Biotage MPLC (40 g column, 25% ethyl acetate in heptane) to give 203 mg (65%) of 3,6-diethyl-N-[(1R,2S)-2-(2-fluoroethoxy)-2,3-dihydro-1H-inden-1-yl]-5-(3-methoxy-5,6,7,8-tetrahydronaphthalen-2-yl)pyrazin-2-amine as an ivory foam. Rf 0.20 (25% ethyl acetate in heptane). IR (diffuse reflectance) 2966, 2932, 2875, 2857, 1562, 1551, 1482, 1389, 1309, 1248, 1232, 1203, 1183, 1118, 1033 cm$^{-1}$. OAMS supporting ions at: ESI+490.2. Anal. Calcd for $C_{30}H_{36}FN_3O_2$: C, 73.59; H, 7.41; N, 8.58; F, 3.88. Found: C, 73.57; H, 7.65; N, 8.41.

Example 24

3,6-diethyl-N-[2-methoxy-1-(methoxymethyl)ethyl]-5-(3-methoxy-5,6,7,8-tetrahydronaphthalen-2-yl)pyrazin-2-amine

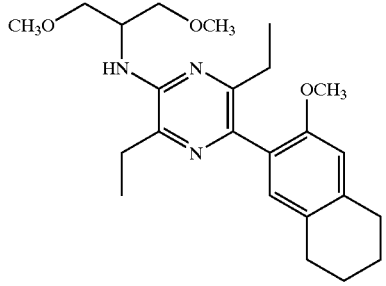

Following the general procedure of Example 1 Step 3 and making non-critical variations but substituting 5-bromo-3,6-diethyl-N-(1-ethylpropyl)pyrazin-2-amine with 5-bromo-3,6-diethyl-N-[2-methoxy-1-(methoxymethyl)ethyl]pyrazin-2-amine (214 mg, 0.644 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 450 mg of a yellow crude oil. This material was purified by Biotage MPLC (40 g column, 7% acetone in heptane) followed by Prep TLC using 10% ethyl acetate in heptane) to give 76 mg (28%) of 3,6-diethyl-N-[2-methoxy-1-(methoxymethyl)ethyl]-5-(3-methoxy-5,6,7,8-tetrahydronaphthalen-2-yl)pyrazin-2-amine as a pale yellow oil. Rf 0.13 (7% acetone in toluene). OAMS supporting ions at: ESI+414.3. HRMS (ESI) calcd for $C_{24}H_{35}N_3O_3$ +H$_1$ 414.2756, found 414.2753.

Example 25

3,6-diethyl-N-[(1R)-1-(methoxymethyl)propyl]-5-(3-methoxy-5,6,7,8-tetrahydronaphthalen-2-yl)pyrazin-2-amine

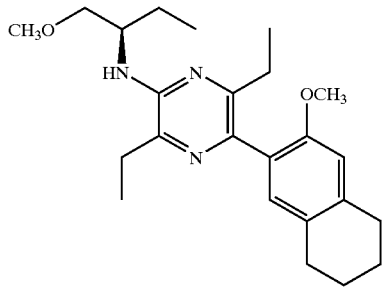

Step 1: 5-bromo-3,6-diethyl-N-[(1R)-1-(methoxymethyl)propyl]pyrazin-2-amine

Following the general procedure of Example 13 Step 3 and making non-critical variations but substituting (2S)-2-

[(5-bromo-3,6-diethylpyrazin-2-yl)amino]butan-1-ol with (2R)-2-[(5-bromo-3,6-diethylpyrazin-2-yl)amino]butan-1-ol (Example 12 Step 2) (353 mg, 1.17 mmol) gave 154 mg (42%) of 5-bromo-3,6-diethyl-N-[(1R)-1-(methoxymethyl)propyl]pyrazin-2-amine as a yellow oil after Biotage MPLC (40 g column, 20% ethyl acetate in heptane).

Step 2: 3,6-diethyl-N-[(1R)-1-(methoxymethyl)propyl]-5-(3-methoxy-5,6,7,8-tetrahydronaphthalen-2-yl)pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1R)-1-(methoxymethyl)propyl]pyrazin-2-amine (266 mg, 0.84 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1), gave 500 mg of a yellow crude oil. This material was purified by Biotage MPLC (90 g column, 2% acetone in toluene) to give 194 mg (58%) of 3,6-diethyl-N-[(1R)-1-(methoxymethyl)propyl]-5-(3-methoxy-5,6,7,8-tetrahydronaphthalen-2-yl)pyrazin-2-amine as a pale yellow oil. Rf 0.17 (2% acetone in toluene). IR (liq.) 2966, 2933, 2876, 2859, 1566, 1551, 1508, 1486, 1464, 1448, 1392, 1248, 1203, 1121, 1110 cm$^{-1}$. OAMS supporting ions at: ESI+398.3. HRMS (ESI) calcd for $C_{24}H_{35}N_3O_2+H_1$ 398.2807, found 398.2794.

Example 26

3,6-diethyl-N-[(1S)-1-(methoxymethyl)propyl]-5-(3-methoxy-5,6,7,8-tetrahydronaphthalen-2-yl)pyrazin-2-amine

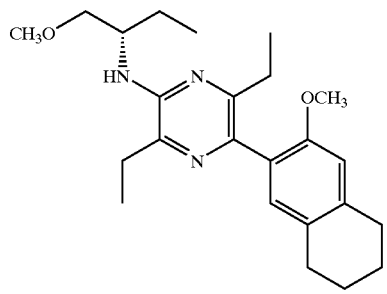

Step 1: 5-bromo-3,6-diethyl-N-[(1S)-1-(methoxymethyl)propyl]pyrazin-2-amine

Following the general procedure of Example 13 Step 3 and making non-critical variations but substituting iodoethane with iodomethane, the reaction was carried out on the alcohol (2S)-2-[(5-bromo-3,6-diethylpyrazin-2-yl)amino]butan-1-ol (Example 13 Step 2) (356 mg, 1.18 mmol) and gave 489 mg of a yellow oil. This material was purified by Biotage MPLC (90 g column) to give 52 mg (14%) of name 5-bromo-3,6-diethyl-N-[(1S)-1-(methoxymethyl)propyl]pyrazin-2-amine as a pale yellow solid. Rf 0.12 (5% ethyl acetate in heptane).

Step 2: 3,6-diethyl-N-[(1S)-1-(methoxymethyl)propyl]-5-(3-methoxy-5,6,7,8-tetrahydronaphthalen-2-yl)pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1S)-1-(methoxymethyl)propyl]pyrazin-2-amine (51 mg, 0.16 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1), gave 100 mg of a yellow crude oil. This material was purified by Biotage MPLC (40 g column, 2% acetone in toluene) to give 37 mg (58%) of 3,6-diethyl-N-[(1S)-1-(methoxymethyl)propyl]-5-(3-methoxy-5,6,7,8-tetrahydronaphthalen-2-yl)pyrazin-2-amine as a pale yellow oil. Rf 0.24 (20% ethyl acetate in heptane). OAMS supporting ions at: ESI+398.3. HRMS (ESI) calcd for $C_{24}H_{35}N_3O_2+H_1$ 398.2807, found 398.2796.

Example 27

N-[(1S)-1-(ethoxymethyl)propyl]-3,6-diethyl-5-(3-methoxy-5,6,7,8-tetrahydronaphthalen-2-yl)pyrazin-2-amine

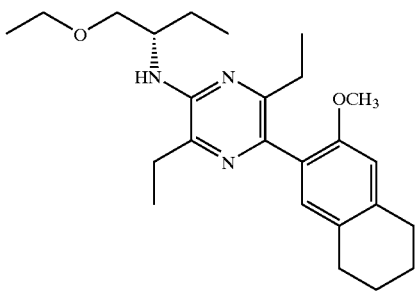

Following the general procedure of Example 1 Step 3 and making non-critical variations but substituting 5-bromo-3,6-diethyl-N-(1-ethylpropyl)pyrazin-2-amine with 5-bromo-N-[(1S)-1-(ethoxymethyl)propyl]-3,6-diethylpyrazin-2-amine Example 13 Step 3 (83 mg, 0.25 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1), gave 157 mg of a yellow crude oil. This material was purified by Biotage MPLC (40 g column, 2% acetone in toluene) to give 49 mg (48%) of N-[(1S)-1-(ethoxymethyl)propyl]-3,6-diethyl-5-(3-methoxy-5,6,7,8-tetrahydronaphthalen-2-yl)pyrazin-2-amine as a yellow oil. OAMS supporting ions at: ESI+412.3. HRMS (ESI) calcd for $C_{25}H_{37}N_3O_2+H_1$ 412.2964, found 412.2972.

Example 28

3,6-diethyl-N-{(1S)-1-[(2-fluoroethoxy)methyl]propyl}-5-(3-methoxy-5,6,7,8-tetrahydronaphthalen-2-yl)pyrazin-2-amine

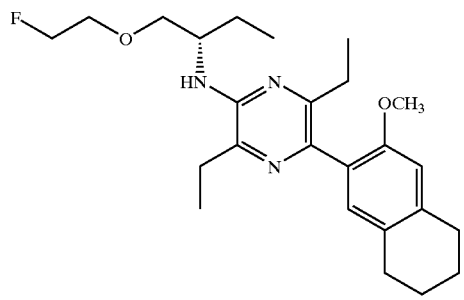

Following the general procedure of Example 1 Step 3 and making non-critical variations but substituting 5-bromo-3,6-diethyl-N-(1-ethylpropyl)pyrazin-2-amine with 5-bromo-3,6-diethyl-N-{(1S)-1-[(2-fluoroethoxy)methyl]propyl}pyrazin-2-amine (Example 14 Step 1) (100 mg, 0.29 mmol) and substituting 6-methoxy-2,3-dihydro-1H-inden-5-ylboronic acid (Preparation 2) with 3-methoxy-5,6,7,8- tetrahydronaphthalen-2-ylboronic acid (Preparation 1) gave 220 mg of an orange crude oil. This material was purified by Biotage MPLC (40 g column, 2% acetone in toluene) to give 85 mg (69%) of 3,6-diethyl-N-{(1S)-1-[(2-fluoroethoxy)methyl]propyl}-5-(3-methoxy-5,6,7,8-tetrahydronaphthalen-2-yl)pyrazin-2-amine as a yellow oil. OAMS supporting ions at: ESI+430.3. HRMS (ESI) calcd for $C_{25}H_{36}FN_3O_2+H_1$ 430.2870, found 430.2875.

Example 29

3,6-diethyl-5-(3-methoxy-5,6,7,8-tetrahydronaphthalen-2-yl)-N-[(1R)-1-phenylethyl]pyrazin-2-amine

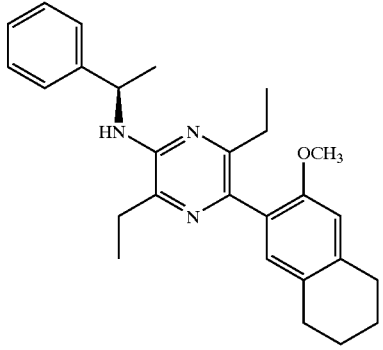

Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1R)-1-phenylethyl]pyrazin-2-amine (Example 15 Step 2) (465 mg, 1.39 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 1.27 mg of an orange crude oil. This material was purified by Biotage MPLC (90 g column, 1.5% acetone in toluene) to give 317 mg (55%) of 3,6-diethyl-5-(3-methoxy-5,6,7,8-tetrahydronaphthalen-2-yl)-N-[(1R)-1-phenylethyl]pyrazin-2-amine. Rf 0.36 (2% acetone in toluene). IR (liq.) 2968, 2933, 1565, 1549, 1508, 1480, 1449, 1387, 1310, 1248, 1233, 1203, 1169, 1035, 699 cm$^{-1}$. OAMS supporting ions at: ESI+416.3. Anal. Calcd for $C_{27}H_{33}N_3O$: C, 78.04; H, 8.00; N, 10.11. Found: C, 78.13; H, 7.97; N, 9.88.

Example 30

3,6-diethyl-5-(3-methoxy-5,6,7,8-tetrahydronaphthalen-2-yl)-N-[(1S)-1-phenylethyl]pyrazin-2-amine

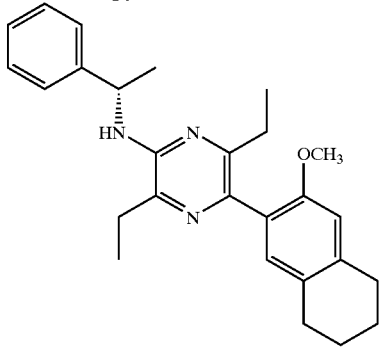

Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1S)-1-phenylethyl]pyrazin-2-amine (Example 16 Step 2) (232 mg, 0.70 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 490 mg of a orange crude oil. This material was purified by Biotage MPLC (40 g column, 1.5% acetone in toluene) to give 189 mg (66%) of 3,6-diethyl-5-(3-methoxy-5,6,7,8-tetrahydronaphthalen-2-yl)-N-[(1S)-1-phenylethyl]pyrazin-2-amine as a yellow oil. Rf 0.36 (2% acetone in toluene). IR (liq.) 2968, 2932, 2872, 1565, 1549, 1507, 1481, 1449, 1387, 1310, 1248, 1233, 1203, 1169, 699 cm$^{-1}$. OAMS supporting ions at: ESI+416.2. HRMS (ESI) calcd for $C_{27}H_{33}N_3O+H_1$ 416.2702, found 416.2702.

Example 31

3,6-diethyl-5-(3-methoxy-5,6,7,8-tetrahydronaphthalen-2-yl)-N-[(1R)-1-methylpropyl]pyrazin-2-amine

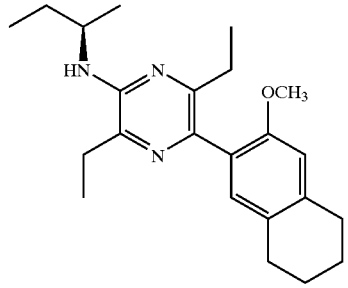

Following the general procedure of Example 1 Step 3 and making non-critical variations but substituting 5-bromo-3,6-diethyl-N-(1-ethylpropyl)pyrazin-2-amine with 5-bromo-3,6-diethyl-N-[(1R)-1-methylpropyl]pyrazin-2-amine as a yellow oil (Example 17 Step 2) (287 mg, 1.0 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 640 mg of a yellow crude oil. This material was purified by Biotage MPLC (90 g column, 1.5% acetone in toluene) to give 279 mg (78%) of 3,6-diethyl-5-(3-methoxy-5,6,7,8-tetrahydronaphthalen-2-yl)-N-[(1R)-1-methylpropyl]pyrazin-2-amine. Rf 0.27 (1.5% acetone in toluene). IR (liq.) 2965, 2933, 2875, 2858, 1565, 1550, 1508, 1486, 1464, 1448, 1390, 1248, 1233, 1204, 1177 cm$^{-1}$. HRMS (ESI) calcd for $C_{23}H_{33}N_3O+H_1$ 368.2702, found 368.2695. $[\alpha]^{25}_D=-17$ (c 0.42, ethanol). Anal. Calcd for $C_{23}H_{33}N_3O$: C, 75.16; H, 9.05; N, 11.43. Found: C, 75.16; H, 9.13; N, 11.00.

Example 32

3,6-diethyl-5-(3-methoxy-5,6,7,8-tetrahydronaphthalen-2-yl)-N-[(1S)-1-methylpropyl]pyrazin-2-amine

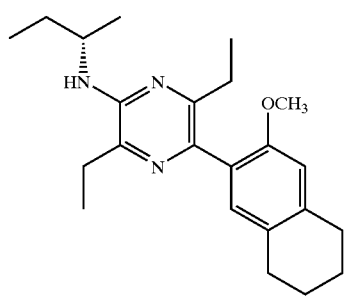

Following the general procedure of Example 1 Step 3 and making non-critical variations but substituting 5-bromo-3, 6-diethyl-N-(1-ethylpropyl)pyrazin-2-amine with 5-bromo-3,6-diethyl-N-[(1S)-1-methylpropyl]pyrazin-2-amine (Example 18 Step 2) (287 mg, 1.0 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 540 mg of a yellow crude oil. This material was purified by Biotage MPLC (90 g column, 1.5% acetone in toluene) to give 248 mg (68%) of 3,6-diethyl-5-(3-methoxy-5,6,7,8-tetrahydronaphthalen-2-yl)-N-[(1S)-1-methylpropyl]pyrazin-2-amine as a yellow oil. Rf 0.27 (1.5% acetone in toluene). IR (liq.) 2965, 2933, 2875, 1565, 1550, 1508, 1486, 1464, 1448, 1390, 1310, 1248, 1233, 1204, 1177 $cm^{-1}$. OAMS supporting ions at: ESI+368.3. HRMS (ESI) calcd for $C_{23}H_{33}N_3O+H_1$ 368.2702, found 368.2703. HRMS (ESI) calcd for $C_{23}H_{33}N_3O+H_1$ 368.2702, found 368.2694. $[\alpha]^{25}_D$=17 (c 0.59, ethanol). Anal. Calcd for $C_{23}H_{33}N_3O$: C, 75.16; H, 9.05; N, 11.43. Found: C, 74.99; H, 9.13; N, 11.16.

Example 33

3,6-diethyl-N-(2-ethylbutyl)-5-(3-methoxy-5,6,7,8-tetrahydronaphthalen-2-yl)pyrazin-2-amine

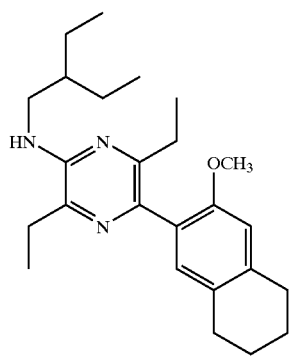

Step 1: 3,6-diethyl-N-(2-ethylbutyl)pyrazin-2-amine

Following the general procedure of Example 1 Step 1 and making non-critical variations but substituting 1-ethyl propylamine with 2-ethyl-n-butylamine (1.52 g, 15 mmol) gave 3.38 g of a dark crude oil. This material was purified by Biotage MPLC (120 g column, 10% ethyl acetate in heptane) to give 1.4 g (79%) of 3,6-diethyl-N-(2-ethylbutyl)pyrazin-2-amine, as a pale yellow oil. Rf 0.28 (20% ethyl acetate in heptane). IR (liq.) 2965, 2935, 2876, 1582, 1547, 1505, 1465, 1450, 1393, 1379, 1362, 1338, 1235, 1178, 1154 $cm^{-1}$. OAMS supporting ions at: ESI+236.3. HRMS (ESI) calcd for $C_{14}H_{25}N_3+H_1$ 236.2127, found 236.2122. Anal. Calcd for $C_{14}H_{25}N_3$: C, 71.44; H, 10.71; N, 17.85. Found: C, 71.56; H, 10.19; N, 17.32.

Step 2: 5-bromo-3,6-diethyl-N-(2-ethylbutyl)pyrazin-2-amine

Following the general procedure of Example 1 Step 2 and making non-critical variations but substituting 3,6-diethyl-N-(1-ethylpropyl)pyrazin-2-amine with 3,6-diethyl-N-(2-ethylbutyl)pyrazin-2-amine (1.1 g, 4.69 mmol) gave 2.01 g of a yellow paste. This material was purified by Biotage MPLC (90 g column, 5% ethyl acetate in heptane) to give 1.32 g (90%) of 5-bromo-3,6-diethyl-N-(2-ethylbutyl)pyrazin-2-amine, as a yellow oil. Rf 0.45 (10% ethyl acetate in heptane). IR (liq.) 2966, 2936, 2876, 1562, 1542, 1485, 1463, 1432, 1392, 1379, 1361, 1338, 1241, 1178, 1163 $cm^{-1}$. OAMS supporting ions at: ESI+316.1. Anal. Calcd for $C_{14}H_{24}BrN_3$: C, 53.51; H, 7.70; N, 13.37; Br, 25.43. Found: C, 53.43; H, 7.66; N, 13.28.

Step 3: 3,6-diethyl-N-(2-ethylbutyl)-5-(3-methoxy-5,6,7,8-tetrahydronaphthalen-2-yl)pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-(2-ethylbutyl)pyrazin-2-amine (314 mg, 1.0 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 690 mg of a yellow crude oil. This material was purified by Biotage MPLC (90 g column, 1.5% acetone in toluene) to give 241 mg (61%) of 3,6-diethyl-N-(2-ethylbutyl)-5-(3-methoxy-5,6,7,8-tetrahydronaphthalen-2-yl)pyrazin-2-amine as a yellow oil. Rf 0.28 (1.5% acetone in toluene). IR (liq.) 2962, 2932, 2874, 2858, 2837, 1567, 1551, 1509, 1492, 1464, 1449, 1354, 1247, 1233, 1204 $cm^{-1}$. OAMS supporting ions at: ESI+396.3. HRMS (ESI) calcd for $C_{25}H_{37}N_3O+H_1$ 396.3015, found 396.3011.

Example 34

N-(dicyclopropylmethyl)-3,6-diethyl-5-(3-methoxy-5,6,7,8-tetrahydronaphthalen-2-yl)pyrazin-2-amine

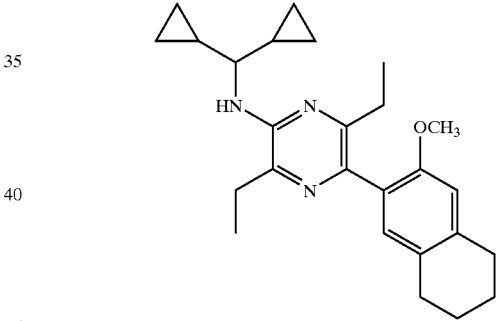

Following the general procedure of Example 1 Step 3 and making non-critical variations but substituting 5-bromo-3,6-diethyl-N-(1-ethylpropyl)pyrazin-2-amine with 5-bromo-N-(dicyclopropylmethyl)-3,6-diethylpyrazin-2-amine (Example 20 Step 2) (324 mg, 1.0 mmol), and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 540 mg of a yellow crude oil. This material was purified by Biotage MPLC (90 g column, 1.5% acetone in toluene) to give 313 mg (77%) of N-(dicyclopropylmethyl)-3,6-diethyl-5-(3-methoxy-5,6,7,8-tetrahydronaphthalen-2-yl)pyrazin-2-amine as a yellow oil. Rf 0.27 (1.5% acetone in toluene). IR (liq.) 2967, 2933, 1565, 1549, 1508, 1484, 1464, 1448, 1390, 1310, 1248, 1233, 1204, 1162, 1034 $cm^{-1}$. OAMS supporting ions at: ESI+406.2. HRMS (ESI) calcd for $C_{26}H_{35}N_3O+H_1$ 406.2858, found 406.2843. Anal. Calcd for $C_{26}H_{35}N_3O$: C, 77.00; H, 8.70; N, 10.36. Found: C, 76.94; H, 8.48; N, 9.73.

Example 35

N-cyclopentyl-3,6-diethyl-5-(3-methoxy-5,6,7,8-tetrahydronaphthalen-2-yl)pyrazin-2-amine

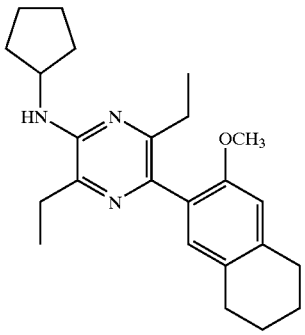

Following the general procedure of Example 1 Step 3 and making non-critical variations but substituting 5-bromo-3,6-diethyl-N-(1-ethylpropyl)pyrazin-2-amine with 5-bromo-N-cyclopentyl-3,6-diethylpyrazin-2-amine (Example 19 Step 2) (298 mg, 1.0 mmol), and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 590 mg of a yellow crude oil. This material was purified by Biotage MPLC (90 g column, 1.5% acetone in toluene) to give 334 mg (88%) of N-cyclopentyl-3,6-diethyl-5-(3-methoxy-5,6,7,8-tetrahydronaphthalen-2-yl)pyrazin-2-amine. Rf 0.25 (1.5% acetone in toluene). IR (liq.) 2934, 2871, 2836, 1565, 1550, 1508, 1484, 1466, 1448, 1390, 1353, 1247, 1233, 1203, 1190 cm$^{-1}$. OAMS supporting ions at: ESI+380.3. HRMS (ESI) calcd for $C_{24}H_{33}N_3O+H_1$ 380.2702, found 380.2703. Anal. Calcd for $C_{24}H_{33}N_3O$: C, 75.95; H, 8.76; N, 11.07. Found: C, 75.98; H, 8.64; N, 10.47.

Example 36

3,6-diethyl-5-(3-methoxy-5,6,7,8-tetrahydronaphthalen-2-yl)-N-(1-propylbutyl)pyrazin-2-amine

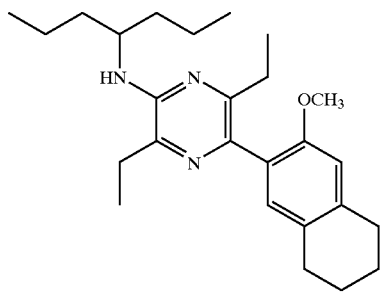

Step 1: 3,6-diethyl-N-(1-propylbutyl)pyrazin-2-amine

Following the general procedure of Example 1 Step 1 and making non-critical variations but substituting 1-ethyl propylamine with 4-heptylamine (1.72 g, 15 mmol) gave 2.02 g of a dark crude oil. This material was purified by Biotage MPLC (90 g column, 5% ethyl acetate in heptane) to give 1.22 g (65%) of 3,6-diethyl-N-(1-propylbutyl)pyrazin-2-amine, as an orange oil. Rf 0.58 (5% ethyl acetate in heptane). IR (liq.) 2960, 2934, 2873, 1581, 1546, 1502, 1466, 1449, 1392, 1380, 1368, 1345, 1266, 1174, 862 cm$^{-1}$. OAMS supporting ions at: ESI+250.3. HRMS (ESI) calcd for $C_{15}H_{27}N_3+H_1$ 250.2283, found 250.2273. Anal. Calcd for $C_{15}H_{27}N_3$: C, 72.24; H, 10.91; N, 16.85. Found: C, 71.88; H, 10.78; N, 16.56.

Step 2: 5-bromo-3,6-diethyl-N-(1-propylbutyl)pyrazin-2-amine, as an orange oil

Following the general procedure of Example 1 Step 2 and making non-critical variations but substituting 3,6-diethyl-N-(1-ethylpropyl)pyrazin-2-amine with 3,6-diethyl-N-(1-propylbutyl)pyrazin-2-amine (0.99 g, 4.0 mmol) gave 1.44 g of a yellow paste. This material was purified by Biotage MPLC (90 g column, 2.5% ethyl acetate in heptane) to give 1.19 g (91%) of 5-bromo-3,6-diethyl-N-(1-propylbutyl)pyrazin-2-amine, as an orange oil. Rf 0.52 (10% ethyl acetate in heptane). IR (liq.) 2960, 2934, 2873, 1560, 1540, 1483, 1465, 1449, 1440, 1418, 1393, 1380, 1368, 1243, 1164 cm$^{-1}$. OAMS supporting ions at:ESI+328.0. HRMS (ESI) calcd for $C_{15}H_{26}N_3Br+H_1$ 328.1389. found 328.1395. Anal. Calcd for $C_{15}H_{26}BrN_3$: C, 54.88; H, 7.98; N, 12.80; Br, 24.34. Found: C, 54.99; H, 8.08; N, 12.90.

Step 3: 3,6-diethyl-5-(3-methoxy-5,6,7,8-tetrahydronaphthalen-2-yl)-N-(1-propylbutyl)pyrazin-2-amine Following the general procedure of Example 1 Step 3 and making non-critical variations but substituting 5-bromo-3,6-diethyl-N-(1-ethylpropyl)pyrazin-2-amine with 5-bromo-3,6-diethyl-N-(1-propylbutyl)pyrazin-2-amine (328 mg, 1.0 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 570 mg of a yellow crude oil. This material was purified by Biotage MPLC (90 g column, 1.5% acetone in toluene) to give 172 mg (42%) of 3,6-diethyl-5-(3-methoxy-5,6,7,8-tetrahydronaphthalen-2-yl)-N-(1-propylbutyl)pyrazin-2-amine as a yellow oil. Rf 0.20 (1.5% acetone in toluene). IR (liq.) 2957, 2931, 2871, 1565, 1550, 1509, 1486, 1465, 1449, 1439, 1391, 1310, 1248, 1204, 1171 cm$^{-1}$. OAMS supporting ions at: ESI+410.2. HRMS (ESI) calcd for $C_{26}H_{39}N_3O+H_1$ 410.3171. found 410.3176. Anal. Calcd for $C_{26}H_{39}N_3O$: C, 76.24; H, 9.60; N, 10.26. Found (av): C, 76.07; H, 9.50; N, 9.76.

Example 37

3,6-diethyl-5-(3-methoxy-5,6,7,8-tetrahydronaphthalen-2-yl)-N-(1-methylbutyl)pyrazin-2-amine

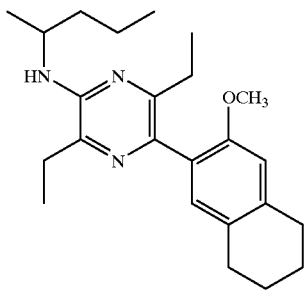

Following the general procedure of Example 1 Step 3 and making non-critical variations but substituting 5-bromo-3,6-diethyl-N-(1-ethylpropyl)pyrazin-2-amine with 5-bromo-3,6-diethyl-N-(1-methylbutyl)pyrazin-2-amine (600 mg, 2.0 mmol) and substituting 6-methoxy-2,3-dihydro-1H-inden-5-ylboronic acid (Preparation 2) with 3-methoxy-5,6,7,8- tetrahydronaphthalen-2-ylboronic acid (Preparation 1) gave 1.26 g of a yellow crude oil. This material was purified by Biotage MPLC (90 g column, 1.5% acetone in toluene) to give 333 mg (44%) of 3,6-diethyl-5-(3-methoxy-5,6,7,8-tetrahydronaphthalen-2-yl)-N-(1-methylbutyl)pyrazin-2-amine as a yellow oil. Rf 0.27 (1.5% acetone in toluene). IR (liq.) 2961, 2932, 2872, 1565, 1550, 1508, 1486, 1465, 1448, 1390, 1310, 1247, 1233, 1204, 1175 cm$^{-1}$. OAMS supporting ions at: ESI+382.2. HRMS (ESI) calcd for $C_{24}H_{35}N_3O+H_1$ 382.2858. found 382.2863. Anal. Calcd for $C_{24}H_{35}N_3O$: C, 75.55; H, 9.25; N, 11.01. Found (av): C, 75.19; H, 8.94; N, 10.68.

Example 38 ethyl 3-{[3,6-diethyl-5-(3-methoxy-5,6,7,8-tetrahydronaphthalen-2-yl)pyrazin-2-yl]amino}butanoate

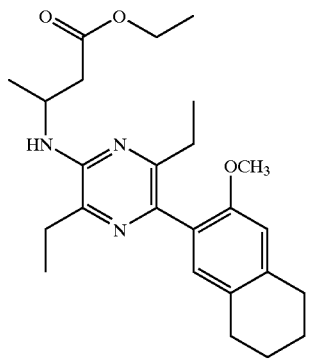

Step 1: Ethyl 3-[(3,6-diethylpyrazin-2-yl)amino]butanoate

A 100 mL dry round bottom flask equipped with a magnetic stir bar and reflux condenser was charged with 2-chloro-3,6-diethylpyrazine (5.12 g, 30 mmol), dry toluene (44 mL), ethyl-3-aminobutyrate (8.72 g, 60 mmol), 2-(di-tert-butylphosphino)biphenyl (0.536 g, 1.8 mmol), sodium tert-butoxide (2.88 g, 30 mmol), and tris(dibenzylidineacetone)dipalladium (0) (0.824 g, 0.90 mmol) respectively. The mixture was heated to 100° C. for 4 hours. After cooling to ambient temperature, the reaction was diluted with ethanol and filtered through a pad of celite. The filtrate was concentrated, diluted with ethyl acetate and filtered through celite again. The resulting filtrate was concentrated in vacuo to give 12.4 g of a dark crude oil. This material was purified in two batches by Biotage MPLC (120 g column, 5% ethyl acetate in heptane). Like fractions were combined to give 3.82 g (48%) of ethyl 3-[(3,6-diethylpyrazin-2-yl)amino]butanoate as a yellow oil. Rf 0.08 (10% ethyl acetate in heptane).

Step 2: ethyl 3-[(5-bromo-3,6-diethylpyrazin-2-yl)amino]butanoate

Following the general procedure of Example 1 Step 2 and making non-critical variations but substituting 3,6-diethyl-N-(1-ethylpropyl)pyrazin-2-amine with ethyl 3-[(3,6-diethylpyrazin-2-yl)amino]butanoate (0.28 g, 1.06 mmol) gave 390 mg of a yellow oil. This material was purified by Biotage MPLC (90 g column, 10% ethyl acetate in heptane) to give 300 mg (83%) of ethyl 3-[(5-bromo-3,6-diethylpyrazin-2-yl)amino]butanoate as a yellow oil. Rf 0.36 (20% ethyl acetate in heptane). IR (liq.) 2976, 1724, 1562, 1541, 1486, 1463, 1448, 1417, 1395, 1376, 1298, 1245, 1200, 1162, 1030 cm$^{-1}$. OAMS supporting ions at: ESI+ 346.0. Anal. Calcd for $C_{14}H_{22}BrN_3O_2$: C, 48.85; H, 6.44; N, 12.21; Br, 23.21. Found: C, 48.95; H, 6.58; N, 12.08.

Step 3: ethyl 3-{[3,6-diethyl-5-(3-methoxy-5,6,7,8-tetrahydronaphthalen-2-yl)pyrazin-2-yl]amino}butanoate Following the general procedure of Example 1 Step 3 and making non-critical variations but substituting 5-bromo-3,6-diethyl-N-(1-ethylpropyl)pyrazin-2-amine with ethyl 3-[(5-bromo-3,6-diethylpyrazin-2-yl)amino]butanoate (274 mg, 0.80 mmol) and substituting 6-methoxy-2,3-dihydro-1H-inden-5-ylboronic acid (Preparation 2) with 3-methoxy-5,6,7,8-tetrahydronaphthalen-2-ylboronic acid (Preparation 1) gave 810 mg of a yellow crude oil. This material was purified by Biotage MPLC (90 g column, 1.5% acetone in toluene) to give 210 mg (62%) of ethyl 3-{[3,6-diethyl-5-(3-methoxy-5,6,7,8-tetrahydronaphthalen-2-yl)pyrazin-2-yl]amino}butanoate as a yellow oil. Rf 0.21 (1.5% acetone in toluene). IR (liq.) 2971, 2934, 1730, 1567, 1508, 1489, 1465, 1448, 1393, 1310, 1248, 1233, 1197, 1162, 1034 cm$^{-1}$. OAMS supporting ions at: ESI+ 426.2. HRMS (ESI) calcd for $C_{25}H_{35}N_3O_3+H_1$ 426.2756. found 426.2749.

Example 39

3-{[3,6-diethyl-5-(3-methoxy-5,6,7,8-tetrahydronaphthalen-2-yl)pyrazin-2-yl]amino}butan-1-ol

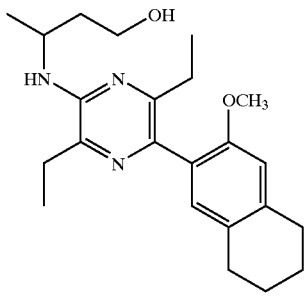

A 250 mL dry round bottom flask equipped with a magnetic stir bar was charged with a solution of ethyl 3-{[3,6-diethyl-5-(3-methoxy-5,6,7,8-tetrahydronaphthalen-2-yl)pyrazin-2-yl]amino}butanoate (Example 38, 2.82 g, 6.62 mmol), in THF (37.6 mL) and cooled with an ice bath. A solution of 1M LAH in THF (33.11 mL, 33.11 mmol) was added to the reaction mixture dropwise. Strong effervescence was observed. The reaction was stirred at ° C. for an additional 15 minutes after the addition was complete, then the ice bath was removed and the reaction stirred at ambient temperature for 2 hours. The reaction color changed from pale yellow to brown. The reaction was cooled with an ice bath again, and quenched with ethyl acetate (33 mL) followed by the dropwsie addition of a saturated aqueous solution of KHSO$_4$ (6.62 mL). Effervescence was observed again. After stirring at ° C. for 20 minutes the ice bath was removed. The addition of KHSO4 caused a gel to form, which turned into a solid within 30 minutes. MgSO$_4$ was added to the mixture, and the heterogeneous solution was filtered through MgSO$_4$. After rinsing with ethyl acetate, the filtrated was concentrated to give 2.74 grams of an auburn oil. This material was purified by Biotage MPLC (120 g column, 5% acetone in toluene) to give 2.16 grams (85%) of 3-{[3,6-diethyl-5-(3-methoxy-5,6,7,8-tetrahydronaphthalen-2-yl)pyrazin-2-yl]amino}butan-1-ol as a white foam. Rf 0.20 (40% ethyl acetate in heptane).

IR (diffuse reflectance) 2965, 2931, 2875, 2859, 2835, 1572, 1493, 1463, 1445, 1391, 1309, 1248, 1232, 1205, 1171 cm$^{-1}$. OAMS supporting ions at: ESI+ 384.2. HRMS (ESI) calcd for $C_{23}H_{33}N_3O_2+H_1$ 384.2651. found 384.2667. HRMS (ESI) calcd for $C_{23}H_{33}N_3O_2+H_1$ 384.2651. found 384.2667.

Example 40

3,6-diethyl-N-(3-methoxy-1-methylpropyl)-5-(3-methoxy-5,6,7,8-tetrahydronaphthalen-2-yl)pyrazin-2-amine

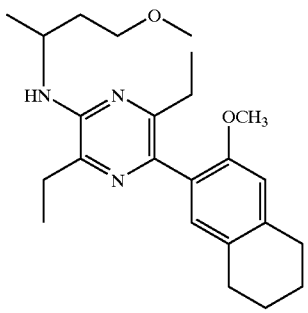

Following the general procedure of Example 13 Step 3 and making non-critical variations but substituting (2S)-2-[(5-bromo-3,6-diethylpyrazin-2-yl)amino]butan-1-ol with 3-{[3,6-diethyl-5-(3-methoxy-5,6,7,8-tetrahydronaphthalen-2-yl)pyrazin-2-yl]amino}butan-1-ol (Example 39, 95 mg, 0.24 mmol) and iodoethane with iodomethane the reaction was carried out and gave 108 mg of a crude yellow oil. This material was purified by Biotage MPLC (40 g column, 20% ethyl acetate in heptane) to give 85 mg (87%) of 3,6-diethyl-N-(3-methoxy-1-methylpropyl)-5-(3-methoxy-5,6,7,8-tetrahydronaphthalen-2-yl)pyrazin-2-amine as a clear oil. Rf 0.30 (5% acetone in toluene). IR (liq.) 2965, 2933, 2873, 1567, 1551, 1494, 1465, 1446, 1392, 1248, 1233, 1204, 1197, 1121, 1110 cm$^{-1}$. OAMS supporting ions at: ESI+398.2.

Example 41

N-(3-ethoxy-1-methylpropyl)-3,6-diethyl-5-(3-methoxy-5,6,7,8-tetrahydronaphthalen-2-yl)pyrazin-2-amine

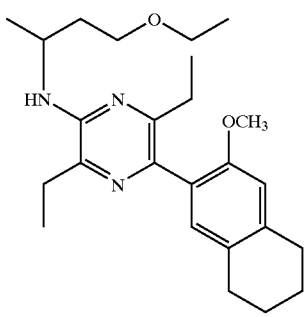

Following the general procedure of Example 13 Step 3 and making non-critical variations but substituting (2S)-2-[(5-bromo-3,6-diethylpyrazin-2-yl)amino]butan-1-ol with 3-{[3,6-diethyl-5-(3-methoxy-5,6,7,8-tetrahydronaphthalen-2-yl)pyrazin-2-yl]amino}butan-1-ol (Example 39, 192 mg, 0.50 mmol) the reaction was carried out and gave a crude yellow oil. This material was purified by Biotage MPLC (40 g column, 20% ethyl acetate in heptane) to give 178 mg (86%) of N-(3-ethoxy-1-methylpropyl)-3,6-diethyl-5-(3-methoxy-5,6,7,8-tetrahydronaphthalen-2-yl)pyrazin-2-amine as a clear oil. Rf 0.25 (5% acetone in toluene). OAMS supporting ions at: ESI+ 412.2.

Example 42

3-{[3,6-diethyl-5-(3-methoxy-5,6,7,8-tetrahydronaphthalen-2-yl)pyrazin-2-yl]amino}butyl acetate

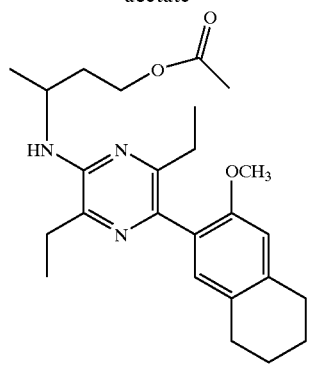

A 25 mL dry round bottom flask equipped with a magnetic stir bar was charged with a solution of 3-{[3,6-diethyl-5-(3-methoxy-5,6,7,8-tetrahydronaphthalen-2-yl)pyrazin-2-yl]amino}butan-1-ol (Example 39, 192 mg, 0.5 mmol) in $CH_2Cl_2$ (5 mL). The reaction was cooled with an ice bath and then treated with pyridine (0.044 mL, 0.55 mmol) followed by acetyl chloride (0.039 mL, 0.55 mmol). The solution turned from clear to a light yellow. The ice bath was removed and the reaction was stirred at ambient temperature for 2 hours. The reaction was diluted with $CH_2Cl_2$, washed twice with water, once with brine, dried with $MgSO_4$, filtered and concentrated to give 217 mg of a crude oil. This material was purified by Biotage MPLC (40 g column, 20% ethyl acetate in heptane) to give 208 mg (97%) of 3-{[3,6-diethyl-5-(3-methoxy-5,6,7,8-tetrahydronaphthalen-2-yl)pyrazin-2-yl]amino}butyl acetate as a clear oil. Rf 0.15 (5% acetone in toluene). OAMS supporting ions at: ESI+ 426.1.

Example 43

Methyl (3R,4S)-3-{[3,6-diethyl-5-(6-methoxy-2,3-dihydro-1H-inden-5-yl)pyrazin-2-yl]amino}-4-ethoxypyrrolidine-1-carboxylate

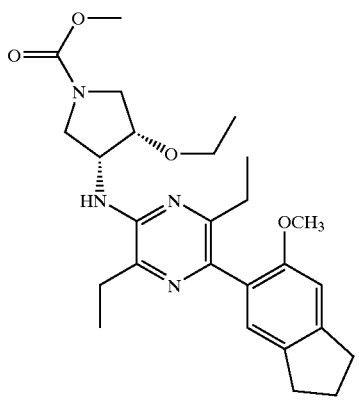

Step 1: Benzyl (3R,4S)-3-[(3,6-diethylpyrazin-2-yl)amino]-4-hydroxypyrrolidine-1-carboxylate

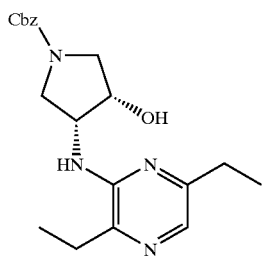

A 250 ml round bottom flask was charged with benzyl (3R,4S)-3-amino-4-hydroxypyrrolidine-1-carboxylate (4.97 g, 21.04 mmol), 2-chloro-3,6-diethylpyrazine (3.95 g, 23.15 mmol), $Pd_2(dba)_3$ (10 mol %, 1.926 g), 2-dicyclohexylphosphino-2'-(N, N-dimethyl amino) biphenyl (20 mol %, 1.66 g), ethylene glycol dimethyl ether (110 mL), and $Cs_2CO_3$ (9.57 g) respectively. The reaction mixture was stirred at 80° C. for 20 hr. It was cooled, diluted with $Et_2O$ (100 ml), poured into $NaHCO_3$ (80 ml), extracted with $CH_2Cl_2$ (150 ml×3), dried ($MgSO_4$), and concentrated. Purification with Biotage MPLC (35% EtOAc in heptane) provided 4.6 g (60%) of benzyl (3R,4S)-3-[(3,6-diethylpyrazin-2-yl)amino]-4-hydroxypyrrolidine-1-carboxylate as an oil. IR (liq.) 2969, 2344, 1996, 1952, 1703, 1691, 1546, 1499, 1449, 1426, 1395, 1359, 1175, 1133, 1095, cm$^{-1}$. HRMS (FAB) calcd for $C_{20}H_{26}N_4O_3+H_1$ 371.2083. found 371.2089.

Step 2: Benzyl (3R,4S)-3-[(3,6-diethylpyrazin-2-yl) amino]-4-ethoxypyrrolidine-1-carboxylate

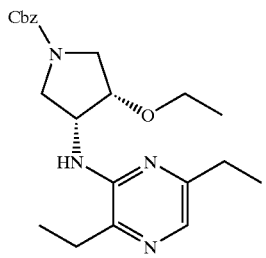

To a solution of benzyl (3R,4S)-3-[(3,6-diethylpyrazin-2-yl)amino]-4-hydroxypyrrolidine-1-carboxylate (17.70 g, 47.8 mmole) in DMF (0.3 M) at 0° C. under $N_2$ was added NaH portionwise (2.48 g, 1.3 eq.). After 15 minutes, iodoethane (4.93 mL, 1.3 eq.) was added dropwise. After 2 hours, the reaction mixture was quenched with brine (200 mL), extracted with ethyl acetate (2×200 mL), dried with $MgSO_4$, filtered and concentrated. Vacuum chromatography was run on a 1 L frit funnel (20–40% ethyl acetate in heptane gradient) to give 14.64 g (77%) of benzyl (3R,4S)-3-[(3,6-diethylpyrazin-2-yl)amino]-4-ethoxypyrrolidine-1-carboxylate as an oil. IR (liq.) 2971, 2936, 2340, 1950, 1709, 1546, 1499, 1464, 1448, 1422, 1395, 1350, 1173, 1129, 1097 (s) cm$^{-1}$ HRMS (ESI) calcd for $C_{22}H_{30}N_4O_3+H_1$ 399.2396. found 399.2392. $[\alpha]^{25}_D$=−50° (c 0.55, 0.1N HCl).

Step 3: N-[(3R,4S)-4-ethoxypyrrolidin-3-yl]-3,6-diethylpyrazin-2-amine

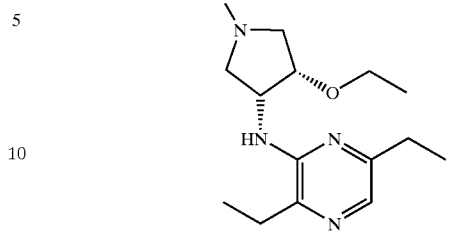

To a solution of benzyl (3R,4S)-3-[(3,6-diethylpyrazin-2-yl)amino]-4-ethoxypyrrolidine-1-carboxylate (14.55 g, 36.5 mmole) in $CH_2Cl_2$ (0.1 M, 365 ml) under $N_2$ was added palladium chloride (1.29 g, 7.24 mmole) and triethyl amine (7.61 mL, 1.5 eq.). Triethylsilane (8.74 mL, 1.5 eq.) was added dropwise over 15 min. After one hour, an additional 8.74 mL of triethylsilane were added dropwise. After 2 additional hours, the reaction mixture was filtered through celite. Trifluoroacetic acid (8 mL) was added and the reaction mixture was stirred for 30 minutes, basified to pH 10 with 2 N aqueous NaOH and extracted with $CH_2Cl_2$ (3×300 ml), dried with $MgSO_4$, filtered and concentrated. Vacuum chromatography was run on a 1 L frit funnel with 5–15% MeOH/$CH_2Cl_2$ with 0.5% $NH_4OH$ gave 8.75 g (91%) of N-[(3R,4S)-4-ethoxypyrrolidin-3-yl]-3,6-diethylpyrazin-2-amine as an oil. IR (liq.) 3438, 2971, 2935, 2874, 2452, 1580, 1546, 1498, 1465, 1448, 1395, 1343, 1164, 1124, 1078 cm$^{-1}$ HRMS (ESI) calcd for $C_{14}H_{24}N_4O+H_1$ 265.2028. found 265.2026. $[\alpha]^{25}_D$=−45° (c 1.02, chloroform).

Step 4: Methyl (3R,4S)-3-[(3,6-diethylpyrazin-2-yl) amino)-4-ethoxypyrrolidine-1-carboxylate

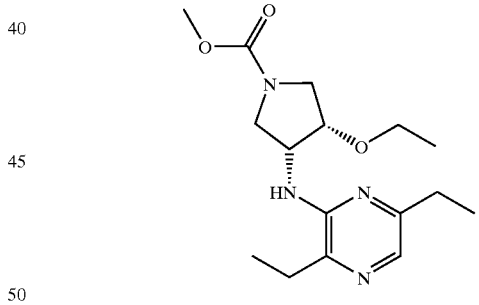

To a solution of N-[(3R,4S)-4-ethoxypyrrolidin-3-yl]-3,6-diethylpyrazin-2-amine (4.50 g, 17 mmole) in $CH_2Cl_2$ (0.1 M, 170 mL) under $N_2$ at 0° C. was added triethyl amine (7.09 mL, 3.0 eq.). Methyl chloroformate (1.44 mL, 1.1 eq.) was added drop-wise over 15 min. After 1 hour, the reaction mixture was poured into saturated aqueous $NaHCO_3$ (150 mL). The aqueous layer was extracted with $CH_2Cl_2$ (1×200 ml), dried with $MgSO_4$, filtered and concentrated. Purification with Biotage MPLC (40 g, 10–50% ethyl acetate in heptane gradient) provided 5.35g (98%) of methyl (3R,4S)-3-[(3,6-diethylpyrazin-2-yl)amino]-4-ethoxypyrrolidine-1-carboxylate as an oil. IR (liq.) 2972, 2937, 2877, 2338, 1937, 1708, 1581, 1546, 1499, 1453, 1392, 1189, 1174, 1135, 1103 (s) cm$^{-1}$ HRMS (ESI) calcd for $C_{16}H_{26}N_4O_3+H_1$ 323.2083. found 323.2089. Anal. Calcd for $C_{16}H_{26}N_4O_3$: C, 59.61; H, 8.13; N, 17.38. Found: C, 59.23; H, 8.35; N, 17.33.

Step 5: Methyl (3R,4S)-3-[(3,6-diethyl-5-iodopyrazin-2-yl)amino]-4-ethoxypyrrolidine-1-carboxylate

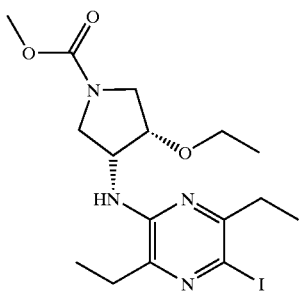

To a solution of the methyl (3R,4S)-3-[(3,6-diethylpyrazin-2-yl)amino]-4-ethoxypyrrolidine-1-carboxylate (5.25 g, 16.2 mmole) in DMF (0.3M, 54 ml) under $N_2$ was added N-iodosuccinimide (4.57, 1.25 eq.). The reaction mixture was heated at 50° C. for 2 hours then cooled to ambient temperature. It was poured into saturated sodium thiosulfate (100 mL) and extracted with ethyl acetate (2×100 ml), dried with $MgSO_4$, filtered and concentrated. Purification with Biotage MPLC (40 g, 10–30% ethyl acetate in heptane gradient) provided 6.45 g (89%) of methyl (3R,4S)-3-[(3,6-diethyl-5-iodopyrazin-2-yl)amino]-4-ethoxypyrrolidine-1-carboxylate as a white solid. 1H NMR (400 MHz, CDCl3) δ 5.06 (m, 1 H), 4.62 (m, 1 H), 4.05 (m, 1 H), 3.88 (m, 1 H), 3.73 (m, 5 H), 3.58 (m, 1 H), 3.43 (m, 1 H), 3.18 (m, 1 H), 2.80 (m, 2 H), 2.62 (q, J=15.8 Hz, 2 H), 1.26 (m, 9 H); IR (diffuse reflectance) 3432, 2976, 2969, 2498, 2461, 2388, 2350, 2337, 1697, 1550, 1535, 1457, 1451, 1392, 771 (s) $cm^{-1}$ HRMS (ESI) calcd for $C_{16}H_{25}N_4O_3I+H_1$ 449.1051. found 449.1029. Anal. Calcd for $C_{16} H_{25}$ I $N_4$ $O_3$: C, 42.87; H, 5.62; N, 12.50. Found: C, 43.01; H, 5.73; N, 12.43.

Step 6: Methyl (3R,4S)-3-{[3,6-diethyl-5-(6-methoxy-2,3-dihydro-1H-inden-5-yl)pyrazin-2-yl]amino}-4-ethoxypyrrolidine-1-carboxylate

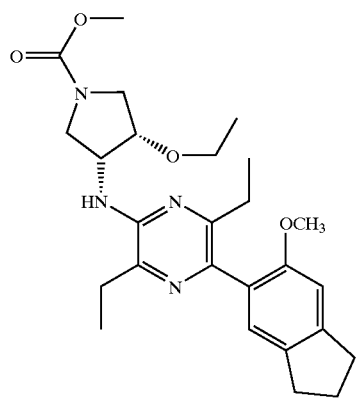

A 7 ml vial was charged with methyl (3R,4S)-3-[(3,6-diethyl-5-iodopyrazin-2-yl)amino]-4-ethoxypyrrolidine-1-carboxylate (100 mg), 6-methoxy-2,3-dihydro-1H-inden-5-ylboronic acid (82 mg) (Preparation 2), tetrakis(triphenylphosphine)palladium (20 mg), 2 M $Na_2CO_3$ (0.4 mL), and ethylene glycol dimethyl ether (1.6 mL). The reaction was stirred for 18 hours at 80° C. The reaction was poured into sat. aq. $NaHCO_3$ and extracted with ethyl ether. The organic phases were combined, dried with $MgSO_4$, filtered, and concentrated. The crude was purified with flash column chromatography (silica, a gradient of 10–25% EtOAc in heptane) to give 97 mg, 95% of methyl (3R,4S)-3-{[3,6-diethyl-5-(6-methoxy-2,3-dihydro-1H-inden-5-yl)pyrazin-2-yl]amino}-4-ethoxypyrrolidine-1-carboxylate. IR (diffuse reflectance) 2967, 2934, 2876, 2350, 2335, 2224, 2063, 1940, 1710, 1568, 1482, 1466, 1451, 1392, 1348 $cm^{-1}$ HRMS (ESI) calcd for $C_{26}H_{36}N_4O_4+H_1$ 469.2815. found 469.2805. Anal. Calcd for $C_{26}H_{36}N_4O_4$: C, 66.64; H, 7.74; N, 11.96. Found: C, 66.27; H, 7.61; N, 11.75.

Example 44

Methyl (3R,4S)-3-{[3,6-diethyl-5-(3-methoxy-5,6,7,8-tetrahydronaphthalen-2-yl)pyrazin-2-yl]amino}-4-ethoxypyrrolidine-1-carboxylate

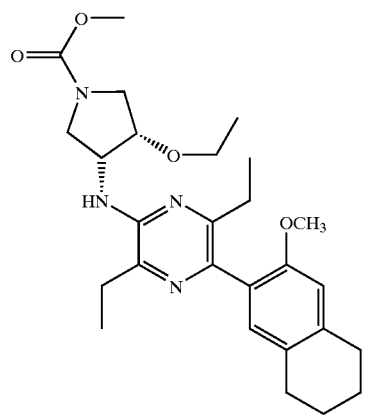

Following the general procedure of Example 43 Step 6 and making non-critical variations but substituting 6-methoxy-2,3-dihydro-1H-inden-5-ylboronic acid (Preparation 2) with 3-methoxy-5,6,7,8-tetrahydronaphthalen-2-ylboronic acid (Preparation 1) 92 mg (87%) of methyl (3R,4S)-3-{[3,6-diethyl-5-(3-methoxy-5,6,7,8-tetrahydronaphthalen-2-yl)pyrazin-2-yl]amino}-4-ethoxypyrrolidine-1-carboxylate was isolated. IR (diffuse reflectance) 2969, 2932, 2876, 2329, 2061, 1708, 1566, 1483, 1452, 1390, 1354, 1200, 1191, 1124, 1103 $cm^{-1}$ HRMS (ESI) calcd for $C_{27}H_{38}N_4O_4+H_1$ 483.2971. found 483.2967. Anal. Calcd for $C_{27} H_{38}$ $N_4$ $O_4$: C, 67.19; H, 7.94; N, 11.61. Found: C, 67.02; H, 7.83; N, 11.31.

Example 45

5-{3,6-diethyl-5-[(1-ethylpropyl)amino]pyrazin-2-yl}-6-methoxyindan-1-one

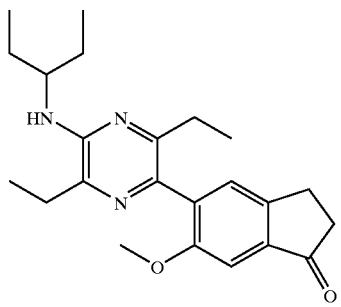

Step 1: 5-bromo-6-methoxyindan-1-one

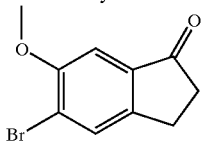

A round bottom flask, fitted with a stir bar and condenser was charged with 5-bromo-6-hydroxy-1-indanone (0.50 g, 2.20 mmol), potassium carbonate (0.456 g, 3.30 mmol), iodomethane (0.341 g, 2.40 mmol), and acetone (10 mL). After heating at reflux for 24 hours the mixture was diluted with ethyl acetate, washed with water (3×10 mL), brine (1×10 mL) and dried with MgSO$_4$. The mixture was filtered and concentrated to give 0.382 g (72%) of 5-bromo-6-methoxyindan-1-one as a white solid. $^1$H NMR (400 MHz, CDCl$_3$) δ 7.73 (s, 1 H), 7.22 (s, 1 H), 3.95 (s, 3 H), 3.10 (m, 2 H), 2.73 (m, 2 H). MS (ESI+) for C$_{10}$H$_9$BrO$_2$ m/z 239.9787 (M+H)$^+$. Anal. Calcd. For C$_{10}$H$_9$BrO$_2$: C, 49.82; H, 3.76. Found: C, 49.69; H, 3.72.

Step 2: 3,6-diethyl-N-(1-ethylpropyl)-5-iodopyrazin-2-amine

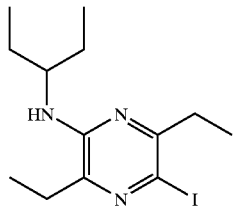

A solution of 3,6-diethyl-N-(1-ethylpropyl)pyrazin-2-amine, NIS (5.37 g, 23.9 mmol) and anhydrous DMF (100 mL) under N$_2$ was heated at 50° C. for 4 h. The solution was partitioned between ethyl acetate and H$_2$O and separated. The aqueous phase was extracted with ethyl acetate and the combined organics were washed with H$_2$O, brine and dried (MgSO$_4$). The mixture was filtered and concentrated to give a brown oil which was purified by flash chromatography (20% ethyl acetate in heptane) to give 5.57 g (74%) of 3,6-diethyl-N-(1-ethylpropyl)-5-iodopyrazin-2-amine as a light brown oil. $^1$H NMR (400 MHz, CDCl$_3$) δ 4.02 (m, 2 H), 2.76 (q, 2 H), 2.57 (q, 2 H), 1.60–1.70 (m, 2 H), 1.45–1.55 (m, 2 H) 1.20–1.30 (m, 6 H), 0.92 (q, 6 H).

Step 3: 5-{3,6-diethyl-5-[(1-ethylpropyl)amino]pyrazin-2-yl}-6-methoxyindan-1-one

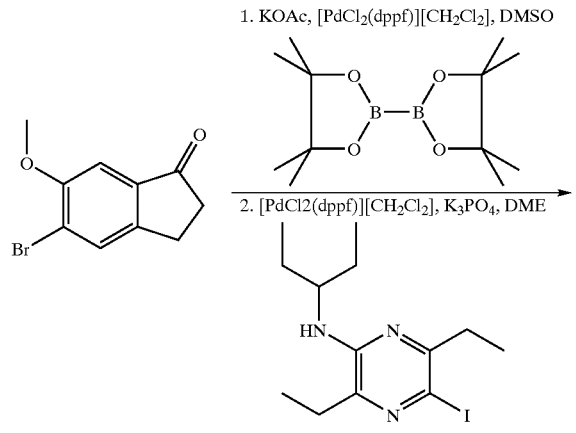

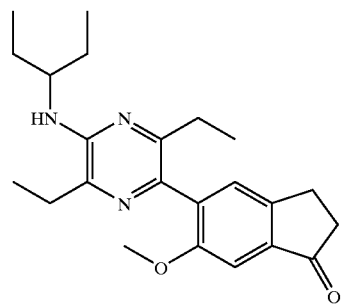

A round bottom flask was charged with [PdCl$_2$(dppf)][CH$_2$Cl$_2$] (0.0327 g, 0.044 mmol), potassium acetate (0.4397 g, 4.48 mmol) and bis(pinacolato)diboron (0.416 g, 1.64 mmol) under N$_2$. Anhydrous DMSO (10 mL) and 5-bromo-6-methoxyindan-1-one (0.360 g, 1.49 mmol) were added. After stirring the mixture at 80° C. for 5 hrs, the reaction was cooled to 0° C. The brown solution was partitioned between ethyl acetate and H$_2$O and separated. The organic layer was washed with water (2×5 mL), dried with MgSO$_4$, filtered and concentrated to give 0.367 g of a brown oil. The crude oil was used without further purification. A round bottom flask fitted with a condenser and stir bar was charged with crude intermediate (0.310 mg, 1.10 mmol), 3,6-diethyl-N-(1-ethylpropyl)-5-iodopyrazin-2-amine (0.344 g, 0.90 mmol), [PdCl$_2$(dppf)][CH$_2$Cl$_2$] (0.040 g, 0.055 mmol), potassium phosphate (0.934 g, 4.40 mmol), and anhydrous ethylene glycol dimethyl ether (3 mL) under N$_2$. After stirring at 90° C. for 17 hours the reaction was cooled to ambient temperature, partitioned between ethyl acetate and water and the layers were separated. The organic layer was washed with water (3×10 mL), dried with MgSO$_4$, filtered and concentrated to provide a yellow powder. The crude product was dissolved in a minimum amount of ethyl acetate, and purified via flash chromatography (20% ethyl acetate in heptane) to give 0.050 g (15%) 5-{3,6-diethyl-5-[(1-ethylpropyl)amino]pyrazin-2-yl}-6-methoxyindan-1-one as a yellow powder. $^1$H NMR (400 MHz, CDCl$_3$) δ 7.42 (s, 1 H), 7.28 (s, 1 H), 4.10–4.20 (m, 2 H), 3.83 (s, 3 H), 3.10–3.20 (m, 2 H), 2.75–2.80 (m, 2 H), 2.69 (br s, 2 H), 2.35–2.60 (s, 2 H), 1.60–1.80 (m, 2 H), 1.50–1.55 (m, 2 H), 1.20–1.40 (m, 6 H), 0.99 (t, J=8 Hz, 6 H). MS (ESI+) for C$_{23}$H$_{31}$N$_3$O$_2$ m/z 382.2 (M+H)$^+$. Anal. Calcd. for C$_{23}$H$_{31}$N$_3$O$_2$: C, 72.41; H, 8.19; N, 11.01. Found C, 72.20; H, 8.14; N, 10.80.

What is claimed is:

1. A compound of Formula I,

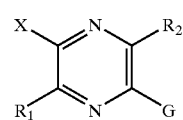

Formula I or a stereoisomer thereof or a pharmaceutically acceptable salt thereof, wherein in Formula I:

R$_1$ and R$_2$ are independently selected from halogen, —NO$_2$, —CN, —R$_a$, —OR$_a$, —S(O)$_m$R$_a$, —NR$_a$R$_a$, —C(O)NR$_a$R$_a$, —C(S)NR$_a$R$_a$, —S(O)$_m$NR$_a$R$_a$, —NR$_a$S(O)$_m$R$_a$, —NR$_a$C(O)OR$_a$, —NR$_a$C(S)OR$_a$, —OC(O)NR$_a$R$_a$, —OC(S)NR$_a$R$_a$, —NR$_a$C(O)NR$_a$R$_a$, —NR$_a$C(S)NR$_a$R$_a$, —C(O)OR$_a$, —C(S)OR$_a$, —OC(O)OR$_a$, or —CR$_a$R$_a$Ar;

X is selected from —NR$_3$R$_4$, —OR$_3$, —CR$_3$R$_4$R$_5$, —C(O)R$_3$, —C(S)R$_3$, —S(O)$_m$R$_3$, —NR$_3$C(O)R$_4$, —NR$_3$C(S)R$_4$, —NR$_3$S(O)$_m$R$_4$, or —R$_3$;

R$_3$, R$_4$, and R$_5$ are independently selected from R$_a$, substituted alkyl, substituted aryl, substituted heteroaryl, substituted cycloalkyl, substituted heterocycloalkyl, aryl cycloalkyl, substituted aryl cycloalkyl, heteroaryl cycloalkyl, substituted heteroaryl cycloalkyl, aryl heterocycloalkyl, substituted aryl heterocycloalkyl, heteroaryl heterocycloalkyl, or substituted heteroaryl heterocycloalkyl;

R$_a$ each is selected from H, alkyl, cycloalkyl, haloalkyl, aryl, heteroaryl, or heterocycloalkyl, where each instance of R$_a$ may be optionally substituted with 1 to 5 of R$_t$, —OR$_t$, —S(O)$_m$R$_t$, —NR$_t$R$_t$, oxo (=O), thione (=S);

R$_t$ each is selected from H, halogen, —NO$_2$, —NH$_2$, —OH, —SH, —CN, —C(O)NH$_2$, —C(S)NH$_2$, —C(O)NHalkyl, —C(S)NHalkyl, —C(O)Nalkylalkyl, —C(S)Nalkylalkyl, —Oalkyl, —NHalkyl, —Nalkylalkyl, —S(O)$_m$alkyl, —SO$_2$NH$_2$, —SO$_2$NHalkyl and —SO$_2$Nalkylalkyl, alkyl, cycloalkyl, haloalkyl, phenyl, benzyl, heteroaryl, or heterocycloalkyl where phenyl, benzyl, heteroaryl, and heterocycloalkyl may be optionally substituted with alkyl or halogen;

G is selected from

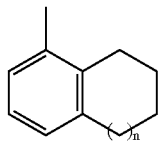 or 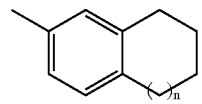

wherein each G group may have from 1 to 6 substituents independently selected from halogen, —CN, —NO$_2$, oxo (=O), thione (=S), —OR$_5$, —SR$_5$, —NR$_5$R$_5$, —C(O)R$_5$, —C(S)R$_5$, —C(O)OR$_5$, —C(S)OR$_5$, —C(O)NR$_5$R$_5$, —C(S)NR$_5$R$_5$, —S(O)$_m$R$_5$, —S(O)$_2$NR$_5$R$_5$, —NR$_5$C(O)R$_5$, —NR$_5$C(S)R$_5$, —NR$_5$C(O)OR$_5$, —NR$_5$C(S)OR$_5$, —NR$_5$C(O)NR$_5$R$_5$, —NR$_5$C(S)NR$_5$R$_5$, —NR$_5$S(O)$_2$R$_5$—OC(O)R$_5$, —OC(S)R$_5$, —OC(O)OR$_5$, —OC(S)OR$_5$, —OC(O)NR$_5$R$_5$, —OC(S)NR$_5$R$_5$, —CR$_5$R$_5$Ar, alkyl, substituted alkyl, cycloalkyl, substituted cycloalkyl, aryl, substituted aryl, heteroaryl, substituted heteroaryl, heterocycloalkyl, or substituted heterocycloalkyl, and wherein each G group may contain up to one double bond in its non-aromatic ring;

Ar is selected from aryl, substituted aryl, heteroaryl and substituted heteroaryl;

m is 0, 1 or 2; and n is 0, 1, or 2.

2. A compound according to claim 1, wherein, in Formula I,

R$_1$ and R$_2$ are independently selected from halogen, —NO$_2$, —CN, —R$_a$, —OR$_a$, —S(O)$_m$R$_a$, or —NR$_a$R$_a$; and X is selected from —NR$_3$R$_4$, —OR$_3$, —C(O)R$_3$, or R$_3$.

3. A compound according to claim 2, wherein, in Formula I, G is

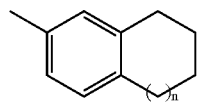

wherein the G group may have from 1 to 6 substituents independently selected from halogen, —CN, —NO$_2$, oxo (=O), thione (=S), —OR$_5$, —SR$_5$, —NR$_5$R$_5$, —C(O)R$_5$, —C(S)R$_5$, —C(O)OR$_5$, —C(S)OR$_5$, —C(O)NR$_5$R$_5$, —C(S)NR$_5$R$_5$, —S(O)$_m$R$_5$, —S(O)$_2$NR$_5$R$_5$, —NR$_5$C(O)R$_5$, —NR$_5$C(S)R$_5$, —NR$_5$C(O)OR$_5$, —NR$_5$C(S)OR$_5$, —NR$_5$C(O)NR$_5$R$_5$, —NR$_5$C(S)NR$_5$R$_5$, —NR$_5$S(O)$_2$R$_5$, —OC(O)R$_5$, —OC(S)R$_5$, —OC(O)OR$_5$, —OC(S)OR$_5$, —OC(O)NR$_5$R$_5$, —OC(S)NR$_5$R$_5$, —CR$_5$R$_5$Ar, alkyl, substituted alkyl, cycloalkyl, substituted cycloalkyl, aryl, substituted aryl, heteroaryl, substituted heteroaryl, heterocycloalkyl, or substituted heterocycloalkyl, and wherein the G group may contain up to one double bond in its non-aromatic ring;

n is 0, or 1.

4. A compound according to claim 3, wherein in Formula I, X is —NR$_3$R$_4$.

5. A compound according to claim 4, wherein, in Formula I, G is

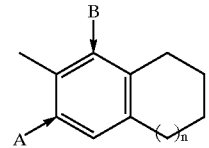

and wherein the G group has 1 to 6 substituents and wherein one said substituent is at either the A position or the B position shown.

6. A compound according to claim 5, wherein, in Formula I, G is

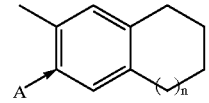

and wherein one said substituent is at the A position shown.

7. A compound according to claim 6, wherein n is 0.

8. A compound according to claim 1, wherein, in Formula I, the G group has at least 1 and up to 6 substituents and wherein one said substituent is either oxo (C=O) or thione (C=S) and is located on the non-aromatic ring.

9. A compound according to claim 8, wherein, in Formula I, R$_1$ and R$_2$ are independently selected from halogen, —NO$_2$, —CN, —R$_a$, —OR$_a$, —S(O)$_m$R$_a$, or —NR$_a$R$_a$; and X is selected from —NR$_3$R$_4$, —OR$_3$, —C(O)R$_3$, or R$_3$.

10. A compound according to claim 9, wherein, in Formula I, G is

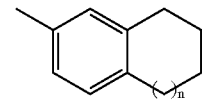

wherein the G group has at least 1 and up to 6 substituents independently selected from halogen, —CN, —NO$_2$, oxo (=O), thione (=S), —OR$_5$, —SR$_5$, —NR$_5$R$_5$, —C(O)R$_5$, —C(S)R$_5$, —C(O)OR$_5$, —C(S)OR$_5$, —C(O)NR$_5$R$_5$, —C(S)NR$_5$R$_5$, S(O)$_m$R$_5$, —S(O)2NR$_5$R$_5$, —NR$_5$C(O)R$_5$, —NR$_5$C(S)R$_5$, —NR$_5$C(O)OR$_5$, —NR$_5$C(S)OR$_5$, —NR$_5$C(O)NR$_5$R$_5$, —NR$_5$C(S)NR$_5$R$_5$, —NR$_5$S(O)$_2$R$_5$, —OC(O)R$_5$, —OC(S)R$_5$, —OC(O)OR$_5$, —OC(S)OR$_5$, —OC(O)NR$_5$R$_5$, —OC(S)NR$_5$R$_5$, —CR$_5$R$_5$Ar, alkyl, substituted alkyl, cycloalkyl, substituted cycloalkyl, aryl, substituted aryl, heteroaryl, substituted heteroaryl, heterocycloalkyl, or substituted heterocycloalkyl, and wherein one said substituent is either oxo (C=O) or thione (C=S) and is located on the non-aromatic ring, and wherein the G group may contain up to one double bond in its non-aromatic ring; and n is 0, or 1.

11. A compound according to claim 10, wherein in Formula I, X is —NR₃R₄.

12. A compound according to claim 11, wherein, in Formula I, G is

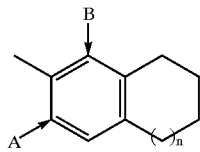

and wherein the G group has at least 2 and up to 6 substituents and wherein one said substituent is at either the A position or the B position shown, and wherein one said substituent is either oxo (C=O) or thione (C=S), and wherein the oxo (C=O) or thione (C=S) substituent is located on the non-aromatic ring.

13. A compound according to claim 12, wherein, in Formula I, G is

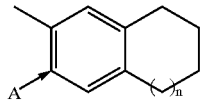

and wherein one said substituent is at the A position shown, and wherein one said substituent is either oxo (C=O) or thione (C=S), and wherein the oxo (C=O) or thione (C=S) substituent is located on the non-aromatic ring.

14. A compound according to claim 13, wherein n is 0.

15. A compound according to claim 1, which is selected from the group consisting of:

3,6-diethyl-N-(1-ethylpropyl)-5-(4-methoxy-7-methyl-2,3-dihydro-1H-inden-5-yl)pyrazin-2-amine;

3,6-diethyl-N-(1-ethylpropyl)-5-(2-methoxy-5,6,7,8-tetrahydronaphthalen-1-yl)pyrazin-2-amine;

3,6-diethyl-N-(1-ethylpropyl)-5-(4-methoxy-5,6,7,8-tetrahydronaphthalen-1-yl)pyrazin-2-amine;

5-(2-ethoxy-5,6,7,8-tetrahydronaphthalen-1-yl)-3,6-diethyl-N-(1-ethylpropyl)pyrazin-2-amine;

3-{3,6-diethyl-5-[(1-ethylpropyl)amino]pyrazin-2-yl}-5,6,7,8-tetrahydronaphthalen-2-yl;

3-{3,6-diethyl-5-[(1-ethylpropyl)amino]pyrazin-2-yl}-5,6,7,8-tefrahydronaphthelen-2-yl trifluoromethanesulfonate;

3,6-diethyl-N-(1-ethylpropyl)-5-(5,6,7,8-tetrahydronaphthalen-2-yl)pyrazin-2-amine;

5-(3-chloro-5,6,7,8-tetrahydronaphthalen-2-yl)-3,6-diethyl-N-(1-ethylpropyl)pyrazin-2-amine;

3,6-diethyl-N-(1-ethylpropyl)-5-(6-methoxy-2,3-dihydro-1 H-inden-5-yl)pyrazin-2-amine;

3,6-diethyl-5-(6-methoxy-2,3-dihydro-1H-inden-5-yl)-N-[2-methoxy-1-(methoxymethyl)ethyl]pyrazin-2-amine;

3,6-diethyl-5-(6-methoxy-2,3-dihydro-1H-inden-5-yl)-N-[(1R)-1-(methoxymethyl)propyl]pyrazin-2-amine;

N-[(1S)-1-(ethoxymethyl)propyl]-3,6-diethyl-5-(6-methoxy-2,3-dihydro-1H-inden-5-yl)pyrazin-2-amine;

3,6-diethyl-N-{(1S)-1-[(2-fluoroethoxy)methyl]propyl}-5-(6-methoxy-2,3-dihydro-1H-inden-5-yl)pyrazin-2-amine;

3,6-diethyl-5-(6-methoxy-2,3-dihydro-1H-inden-5-yl)-N-[(1R)-1-phenylethyl]pyrazin-2-amine;

3,6-diethyl-5-(6-methoxy-2,3-dihydro-1H-inden-5-yl)-N-[(1S)-1-phenylethyl]pyrazin-2-amine;

3,6-diethyl-5-(6-methoxy-2,3-dihydro-1H-inden-5-yl)-N-[(1R)-1-methylpropyl]pyrazin-2-amine;

3,6-diethyl-5-(6-methoxy-2,3-dihydro-1H-inden-5-yl)-N-[(1S)-1-methylpropyl]pyrazin-2-amine;

N-cyclopentyl-3,6-diethyl-5-(6-methoxy-2,3-dihydro-1H-inden-5-yl)pyrazin-2-amine;

N-(dicyclopropylmethyl)-3,6-diethyl-5- (6-methoxy-2,3-dihydro-1H-inden-5-yl)pyrazin-2-amine;

3,6-diethyl-5-(6-methoxy-2,3-dihydro-1H-inden-5-yl)-N-(1-methylbutyl)pyrazin-2-amine;

3,6-diethyl-N-(1ethylpropyl)-5-(3-methoxy-5,6,7,8-tetrahydronaphthalen2-yl)pyrazin-2amine;

(1R,2S)-1-{[3,6-diethyl-5-(3-methoxy-5,6,7,8-tetrahydronaphthalen-2-yl)pyrazin-2-yl]amino}-2,3-dihydro-1H-inden-2-ol;

3,6-diethyl-N-[(1R,2S)-2-(2-fluoroethoxy)-2,3-dihydro-1H -inden-1-yl]-5-(3-methoxy-5,6,7,8-tetrahydronaphthalen-2-yl)pyrazin-2-amine;

3,6-diethyl-N-[2-methoxy-1-(methoxymethyl)ethyl]-5-(3-methoxy-5,6,7,8-tetrahydronaphthalen-2-yl)pyrazin-2-amine;

3,6-diethyl-N-[(1R)-1-(methoxymethyl)propyl]-5-(3-methoxy-5,6,7,8-tetrahydronaphthalen2-yl)pyrazin-2-amine;

3,6-diethyl-N-[(1S)-1-(methoxymethyl)propyl]-5-(3-methoxy-5,6,7,8-tetrahydronaphthalen-2-yl)pyrazin-2-amine;

N-[(1S)-1-(ethoxymethyl)propyl]-3,6-diethyl-5-(3-methoxy-5,6,7,8-tetrahydronaphthalen-2-yl)pyrazin-2-amine;

3,6-diethyl-N-{(1S)-1-[(2-fluoroethoxy)methyl]propyl}-5-(3-methoxy-5,6,7,8-tetrahydronaphthalen-2-yl)pyrazin-2-amine;

3,6-diethyl-5-(3-methoxy-5,6,7,8-tetrahydronaphthalen-2-yl)-N-[(1R)-1-phenylethyl]pyrazin-2-amine;

3,6-diethyl-5-(3-methoxy-5,6,7,8-tetrahydronaphthalen-2-yl)-N-[(1S)-1-phenylethyl]pyrazin-2-amine;

3,6-diethyl-5-(3-methoxy-5,6,7,8-tetrahydronaphthalen-2-yl)-N-[(1R)-1-methylpropyl]pyrazin-2-amine;

3,6-diethyl-5-(3-methoxy-5,6,7,8-tetrahydronaphthalen-2-yl)-N-[(1S)-1-methylpropyl]pyrazin-2-amine;

3,6-diethyl-N-(2-ethylbutyl)-5-(3-methoxy-5,6,7,8-tetrahydronaphthalen-2-yl)pyrazin-2-amine;

N-(dicyclopropylmethyl)-3,6-diethyl-5(3methoxy-5,6,7,8-tetrahydronaphthalen-2-yl)pyrazin-2-amine;

N-cyclopentyl-3,6-diethyl-5-(3-methoxy-5,6,7,8-tetrahydronaphthalen-2-yl)pyrazin-2-amine;

3,6-diethyl-5-(3-methoxy-5,6,7,8-tetrahydronaphthalen-2-yl)-N-(1-propylbutyl)pyrazin-2-amine;

3,6-diethyl-5-(3-methoxy-5,6,7,8-tetrahydronaphthalen-2-yl)-N-(1-methylbutyl)pyrazin-2-amine;

ethyl 3-{[3,6-diethyl-5-(3-methoxy-5,6,7,8-tetrahydronaphthalen-2-yl)pyrazin-2-yl]amino}butanoate;

3-{[3,6-diethyl-5-(3-methoxy-5,6,7,8-tetrahydronaphthalen-2-yl)pyrazin-2-yl]amino}butan-1-ol;

3,6-diethyl-N-(3-methoxy-1-methylpropyl)-5-(3-methoxy-5,6,7,8-tetrahydronaphthalen-2-yl)pyrazin-2-amine;

N-(3-ethoxy-1-methylpropyl)-3,6diethyl-5-(3-methoxy-5,6,7,8-tetrahydronaphthalen-2-yl)pyrazin-2-amine;

3-{[3,6-diethyl-5-(3-methoxy-5,6,7,8-tetrahydronaphthalen-2-yl)pyrazin-2-yl]amino}butyl acetate;

Methyl (3R,4S)-3-{[3,6-diethyl-5-(6-methoxy-2,3-dihydro-1H-inden-5-yl)pyrazin-2-yl]amino}-4-ethoxypyrrolidine-1-carboxylate;

Methyl (3R,4S)-3-{[3,6-diethyl-5-(3-methoxy-5,6,7,8-tetrahydronaphthalen-2-yl)pyrazin-2-yl]amino}-4-ethoxypyrrolidine-1-carboxylate;

5-{3,6-diethyl-5-[(1-ethylpropyl)amino]pyrazin-2-yl}-6-methoxyindan-1-one;

3,6-diethyl-N-(1-ethylpropyl)-5-(6-ethynyl-2,3-dihydro-1H-inden-5-yl)pyrazin-2-amine;

5-{3,6-diethyl-5-[(1-ethylpropyl)amino]pyrazin-2-yl}-2-hydroxy-6-methoxy-2-1-methylindan-1-one;

N-[3,6-diethyl-5-(6-methoxy-2,3-dihydro-1H-inden-5-yl)pyrazin-2-yl]pyridin-2-amine;

N-[(2S,4R)-2-ethoxy-4-phenylcyclopentyl]-3,6-diethyl-5-(6-methoxy-2,3-dihydro-1H-inden-5-yl)pyrazin-2-amine;

3,6-diethyl-5-(6-methoxy-2,3-dihydro-1H-inden-5-yl)-N-[(2R,4R)-4-methoxy-2-(methoxymethyl)cyclopentyl]pyrazin-2-amine;

2,5-diethyl-3-(1-ethylpropoxy)-6-(6-methoxy-2,3-dihydro-1H-inden-5-yl)pyrazine;

3,6-diethyl-N-(1-ethylpropyl)-5-(4-methoxy-2,3-dihydro-1H-inden-5-yl)pyrazin-2-amine;

3,6-diethyl-N-(1-ethylpropyl)-5-(6-methoxy-4-methyl-2,3-dihydro-1H-inden-5-yl)pyrazin-2-amine;

3,6-diethyl-N-(1-ethylpropyl)-5-(5-methoxy-1H-inden-6-yl)pyrazin-2-amine;

3,6-diethyl-N-(1-ethylpropyl)-5-(3-methoxy-5,6-dihydronaphthalen-2-yl)pyrazin-2-amine;

3,6-diethyl-5-(6-methoxy-2,3-dihydro-1H-inden-5-yl)-N-{1-[(2S)-2-(methylamino)cyclopropyl]propyl}pyrazin-2-amine;

6-{3,6-diethyl-5-[(1-ethylpropyl)amino]pyrazin-2-yl}indane-5-carbonitrile;

6-{3,6-diethyl-5-[(1-ethylpropyl)amino]pyrazin-2-yl}-5-methoxyindan-1-one;

6-{3,6-diethyl-5-[(1-ethylpropyl)amino]pyrazin-2-yl}-7-methoxy-3,4-dihydronaphthalen-1 (2H)-one;

5-{3,6-diethyl-5-[(1-ethylpropyl)amino]pyrazin-2-yl}-6-methoxyindan-1-ol;

5-(1-amino-6-methoxy-2,3-dihydro-1H-inden-5-yl)-3,6-diethyl-N-(1-ethylpropyl)pyrazin-2-amine;

2,5-diethyl-3-(6-methoxy-2,3-dihydro-1H-inden-5-yl)-6-pyrrolidin-1-ylpyrazine;

3,6-diethyl-N-(1-ethylpropyl)-5-(6-methyl-2,3-dihydro-1H-inden-5-yl)pyrazin-2-amine;

N-(1-ethylpropyl)-5-(6-methoxy-2,3-dihydro-1H-inden-5-yl)-3,6-dimethylpyrazin-2-amine; (1E)-5-{(3,6-diethyl-5-[(1-ethylpropyl)amino]pyrazin-2-yl}-6-methoxyindan-1-one oxime;

3,6-diethyl-N-(1-ethylpropyl)-5-[6-methoxy-1-(methylamino)-2,3-dihydro-1H-inden-5-yl]pyrazin-2-amine;

N-(5-{3,6-diethyl-5-[(1-ethylpropyl)amino]pyrazin-2-yl}-6-methoxy-2,3-dihydro-1H-inden-1-yl)acetamide;

5-(1,6-dimethoxy-2,3-dihydro-1H-inden-5-yl)-3,6-diethyl-N-(1-ethylpropyl)pyrazin-2-amine;

5-{3,6-diethyl-5-[(1-ethylpropyl)amino]pyrazin-2-yl}-6-methoxy-2,3-dihydro-1H-inden-1-yl acetate;

N-(5-{3,6-diethyl-5-[(1-ethylpropyl)amino]pyrazin-2-yl}-6-methoxy-2,3dihydro-1H-inden-1-yl)urea;

N-(5-{3,6-diethyl-5-[(1-ethylpropyl)amino]pyrazin-2-yl}-6-methoxy-2,3-dihydro-1H-inden-1-yl)ethanethioamide;

5-{3,6-diethyl-5-[(1-ethylpropyl)amino]pyrazin-2-yl}-6-fluoroindan-1-one;

5-{3,6-diethyl-5-[(1-ethylpropyl)amino]pyrazin-2-yl}-6-methoxy-1-methylindan-1-ol 5-{3,6-diethyl-5-[(1-ethylpropyl)amino]pyrazin-2-yl}-6-methoxy-1H-inden-1-one;

5-{3,6-diethyl-5-[(1-ethylpropyl)amino]pyrazin-2-yl}-6-methoxy-1,3-dihydro-2H-inden-2-one;

5-{3,6-diethyl-5-[(1-ethylpropyl)amino]pyrazin-2-yl}-6-methoxy-1H-indene-1,3(2H)-dione;

2,5-diethyl-3-(6-methoxy-2,3-dihydro-1H-inden-5-yl)-6-[(2S,4R)-4-methoxy-2-(methoxymethyl)pyrrolidin-1-yl]pyrazine;

5-{3,6-diethyl-5-[(1-ethylpropyl)amino]pyrazin-2-yl}-6-methoxyindane-1-thione;

5-{6-ethyl-5-[(1-ethylpropyl)amino]-3-methylpyrazin-2-yl}-6-methoxyindan-1-one;

5-[3-ethyl-5-[(1-ethylpropyl)amino]-6-(methoxymethyl)pyrazin-2-yl]-6-methoxyindane-1-thione;

5-[6-ethyl-5-[(1-ethylpropyl)amino]-3-(methoxymethyl)pyrazin-2-yl]-6-methoxyindane-1-thione;

1-[(5-{3,6-diethyl-5-[(1-ethylpropyl)amino]pyrazin-2-yl}-6-methoxy-2,3-dihydro-1H-inden-1-yl)oxy]acetone;

1-[(5-{3,6-diethyl-5-[(1-ethylpropyl)amino]pyrazin-2-yl}-6-methoxy-2,3-dihydro-1H-inden-1-yl)oxy]acetone;

2-[(5-{3,6-diethyl-5-[(1-ethylpropyl)amino]pyrazin-2-yl}-6-methoxy-2,3-dihydro-1H-inden-1-yl)oxy]ethanethioamide;

3,6-diethyl-5-(6-methoxy-2,3-dihydro-1H-inden-5-yl)-N-(1-phenylpropyl)pyrazin-2-amine;

5-{3,6-diethyl-5-[(1-phenylpropyl)amino]pyrazin-2-yl}-6-methoxyindan-1-one;

5-{5-[(3-amino-1-methylpropyl)amino]-3,6-diethylpyrazin-2-yl}-6-methoxyindan-1-one;

N-(3-{[3,6-diethyl-5-(6-methoxy-2,3-dihydro-1H-inden-5-yl)pyrazin-2-yl]amino}butyl)urea;

N-(3-{[3,6-diethyl-5-(6-methoxy-2,3-dihydro-1H-inden-5-yl)pyrazin-2-yl]amino}butyl)thiourea;

5-[6-(difluoromethoxy)-2,3-dihydro-1H-inden-5-yl]-3,6-diethyl-N-(1-ethylpropyl)pyrazin-2-amine;

5-[3-(difluoromethoxy)-5,6,7,8-tetrahydronaphthalen-2-yl]-3,6-diethyl-N-(1-ethylpropyl)pyrazin-2-amine;

3,6-diethyl-N-(1-ethylpropyl)-5-[6-(trifluoromethoxy)-2,3-dihydro-1H-inden-5-yl]pyrazin-2-amine;

5-[6-(difluoromethoxy)-4-methoxy-2,3-dihydro-1H-inden-5-yl]-3,6-diethyl-N-(1-ethylpropyl)pyrazin-2-amine;

5-(4,6-dimethyl-2,3-dihydro-1H-inden-5-yl)-3,6-diethyl-N-(1-ethylpropyl)pyrazin-2-amine;

5-(1,3-dimethoxy-5,6,7,8-tetrahydronaphthalen-2-yl)-3,6-diethyl-N-(1-ethylpropyl)pyrazin-2-amine;

5-[3-(difluoromethoxy)-1-methoxy-5,6,7,8-tetrahydronaphthalen-2-yl]-3,6-diethyl-N-(1-ethylpropyl)pyrazin-2-amine;

5-{4-[3-(dimethylamino)propyl]-6-methoxy-2,3dihydro-1H-inden-5-yl}-3,6-diethyl-N-(1-ethylpropyl)pyrazin-2-amine;

5-{4-[2-(dimethylamino)ethoxy]-6-methoxy-2,3-dihydro-1H-inden-5-yl}-3,6-diethyl-N-(1-ethylpropyl)pyrazin-2-amine;

3,6-diethyl-N-(1-ethylpropyl)-5-[6-methoxy-4-(3-morpholin-4-ylpropyl)-2,3-dihydro- 1H-inden-5-yl]pyrazin-2-amine;

3,6-diethyl-N-(1-ethylpropyl)-5-[6-methoxy-4-(3-morpholin-4-ylpropyl)2,3-dihydro-1H-inden-5-yl]pyrazin-2-amine;

3,6-diethyl-5-(6-methoxy-2,3-dihydro-1H-inden-5-yl)-N-(1-pyridin-2-ylpropyl)pyrazin-2-amine;

3,6-diethyl-5-(6-methoxy-2,3-dihydro-1H-inden-5-yl)-N-(2-methoxy-1-phenylethyl)pyrazin-2-amine;

3,6-diethyl-5-(6-methoxy-2,3-dihydro-1H-inden-5-yl)-N-(2-methoxy-1-phenylethyl)pyrazin-2-amine;

3,6diethyl-5-(3-methoxy-5,6,7,8-tetrahydronaphthalen-2-yl)-N-(1-pyridin-3-ylpropyl)pyrazin-2-amine;

3-{[3,6-diethyl-5-(3-methoxy-5,6,7,8-tetrahydronaphthalen-2-yl)pyrazin-2-yl]amino}-3-phenylpropan-1-ol;

3,6-diethyl-N-(3-methoxy-1-phenylpropyl)-5-(3-methoxy-5,6,7,8-tetrahydronaphthalen-2-yl)pyrazin-2-amine;

3,6-diethyl-N-(1-ethylpropyl)-5-(5-fluoro-3-methoxy-7,8-dihydronaphthalen-2-yl)pyrazin-2-amine;

N,N,3,6-tetraethyl-5-(6-methoxy-2,3-dihydro-1H-inden-5-yl)pyrazine-2-carboxamide;

3,6-diethyl-N-(1-ethylpropyl)-5-(1-fluoro-6-methoxy-2,3-dihydro-1H-inden-5-yl)pyrazin-2-amine;

3,6-diethyl-N-(1-ethylpropyl)-5-(2-fluoro-6-methoxy-2,3-dihydro-1H-inden-5-yl)pyrazin-2-amine; and a pharmaceutically acceptable salt of any of said compounds.

16. A compound according to claim 15, which is selected from the group consisting of:

3,6-diethyl-N-(1-ethylpropyl)-5-(4-methoxy-7-methyl-2,3-dihydro-1H-inden-5-yl)pyrazin-2-amine;

3,6-diethyl-N-(1-ethylpropyl)-5-(2-methoxy-5,6,7,8-tetrahydronaphthalen-1-yl)pyrazin-2-amine;

3,6-diethyl-N-(1-ethylpropyl)-5-(4-methoxy-5,6,7,8-tetrahydronaphthalen-1-yl)pyrazin-2-amine;

5-(2-ethoxy-5,6,7,8-tetrahydronaphthalen-1-yl)-3,6-diethyl-N-(1-ethylpropyl)pyrazin-2-amine;

3-{3,6-diethyl-5-[(1-ethylpropyl)amino]pyrazin-2-yl}-5,6,7,8-tetrahydronaphthalen-2ol;

3-{3,6-diethyl-5-[(1-ethylpropyl)amino]pyrazin-2-yl}-5,6,7,8-tetrahydronaphthalen-2-yl trifluoromethanesulfonate;

3,6-diethyl-N-(1-ehtylpropyl)-5-(5,6,7,8-tetrahydronaphthalen-2-yl)pyrazin-2-amine;

5-(3-chloro-5,6,7,8-tetrahydronaphthalen-2-yl)-3,6-diethyl-N-(1-ethylpropyl)pyrazin-2-amine;

3,6-diethyl-N-(1-ethylpropyl)-5-(6-methoxy-2,3-dihydro-1H-inden-5-yl)pyrazin-2-amine;

3,6-diethyl-5-(6-methoxy-2,3-dihydro-1H-inden-5-yl)-N-[2-methoxy-1-(methoxymethyl)ethyl]pyrazin-2-amine;

3,6-diethyl-5-(6-methoxy-2,3-dihydro-1H-inden-5-yl)-N-[(1R)-1-(methoxymethyl)propyl]pyrazin-2-amine;

N-[(1S)-1-(ethoxymethyl)propyl]-3,6-diethyl-5-(6-methoxy-2,3-dihydro-1H-inden-5-yl)pyrazin-2-amine;

3,6-diethyl-N-{(1S)-1-[(2-fluoroethoxy)methyl]propyl}-5-(6-methoxy-2,3-dihydro-1-H-inden-5-yl)pyrazin-2-amine;

3,6-diethyl-5-(6-methoxy-2,3-dihydro-1H-inden-5-yl)-N-[(1R)-1-phenylethyl]pyrazin-2-amine;

3,6-diethyl-5-(6-methoxy-2,3-dihydro-1H-inden-5-yl)—N-[(1S)-1-phenylethyl]pyrazin-2-amine;

3,6-diethyl-5-(6-methoxy-2,3-dihydro-1H-inden-5-yl)-N-[(1R)-1-methylpropyl]pyrazin-2-amine;

3,6-diethyl-5-(6-methoxy-2,3-dihydro-1H-inden-5-yl)-N-[(1S)-1-methylpropyl]pyrazin-2-amine;

N-cyclopentyl-3,6-diethyl-5-(6-methoxy-2,3-dihydro-1H-inden-5-yl)pyrazin-2-amine;

N-(dicyclopropylmethyl)-3,6-diethyl-5-(6-methoxy-2,3-dihydro-1H-inden-5-yl)pyrazin-2-amine;

3,6-diethyl-5-(6-methoxy-2,3-dihydro-1H-inden-5-yl)-N-(1-methylbutyl)pyrazin-2-amine;

3,6-diethyl-N-(1-ethylpropyl)-5-(3-methoxy-5,6,7,8-tetrahydronaphthalen-2-yl)pyrazin-2-amine;

(1R,2S)-1-{[diethyl-5-(3-methoxy-5,6,7,8-tetrahydronaphthalen2-yl)pyrazin2yl]amino}-2,3-dihydro-1H-inden-2-ol;

3,6-diethyl-N-[(1R,2S)-2-(2-fluoroethoxy)-2,3-dihydro-1H-inden-1-yl]-5-(3-methoxy-5,6,7,8-tetrahydronaphthalen-2-yl)pyrazin-2-amine;

3,6-diethyl-N-[2-methoxy-1-(methoxymethyl)ethyl]-5-(3-methoxy-5,6,7,8-tetrahydronaphthalen-2-yl)pyrazin-2-amine;

3,6-diethyl-N-[(1R)-1-(methoxymethyl)propyl]-5-(3-methoxy-5,6,7,8- tetrahydronaphthalen-2-yl)pyrazin-2-amine;

3,6-diethyl-N-[(1S)-1-(methoxymethyl)propyl]-5-(3-methoxy-5,6,7,8-tetrahydronaphthalen-2-yl)pyrazin-2-amine;

N-[(1S)-1-(ethoxymethyl)propyl]-3,6-diethyl-5-(3-methoxy-5,6,7,8tetrahydronaphthalen-2-yl)pyrazin-2-amine;

3,6-diethyl-N-{(1S)-1-[(2-fluoroethoxy)methyl]propyl}-5-(3-methoxy-5,6,7,8-tetrahydronaphthalen-2-yl)pyrazin-2-amine;

3,6-diethyl-5-(3-methoxy-5,6,7,8-tetrahydronaphthalen-2-y1)-N-[(1R)-1-phenylethyl]pyrazin-2-amine;

3,6-diethyl-5-(3-methoxy-5,6,7,8-tetrahydronaphthalen-2-yl)-N-[(1S)-1-phenylethyl]pyrazin-2-amine;

3,6-diethyl-5-(3-methoxy-5,6,7,8-tetrahydronaphthalen-2-yl)-N-[(1R)-1-methylpropyl]pyrazin-2-amine;

3,6-diethyl-5-(3-methoxy-5,6,7,8-tetrahydronaphthalen-2-yl)-N-[(1S)-1-methylpropyl]pyrazin-2-amine;

3,6-diethyl-N-(2-ethylbutyl)-5-(3-methoxy-5,6,7,8-tetrahydronaphthalen-2-yl)pyrazin-2-amine;

N-(dicyclopropylmethyl)-3,6-diethyl -5-(3-methoxy-5,6,7,8-tetrahydronaphthalen-2-yl)pyrazin-2-amine;

N-cyclopentyl-3,6-diethyl-5-(3-methoxy-5,6,7,8-tetrahydronaphthalen-2-yl)pyrazin-2-amine;

3,6-diethyl -5-(3-methoxy-5,6,7,8-tetrahydronaphthalen-2-yl)-N-(1-propylbutyl)pyrazin-2-amine;

3,6-diethyl-5-(3-methoxy-5,6,7,8-tetrahydronaphthalen2-yl)-N-(1-methylbutyl)pyrazin-2-amine;

ethyl 3-{[3,6-diethyl-5-(3-methoxy-5,6,7,8-tetrahydronaphthalen-2-yl)pyrazin-2-yl]amino}butanoate;

3-{[3,6-diethyl-5-(3-methoxy-5,6,7,8-tetrahydronaphthalen-2-yl)pyrazin-2-yl]amino}butan-1-ol;

3,6-diethyl-N-(3-methoxy-1-methylpropyl)-5-(3-methoxy-5,6,7,8-tetrahydronaphthalen-2-yl)pyrazin-2-amine;

N-(3-ethoxy-1-methylpropyl)-3,6-diethyl-5-(3-methoxy-5,6,7,8-tetrahydronaphthalen-2-yl)pyrazin-2-amine;

3-{[3,6-diethyl-5-(3-methoxy-5,6,7,8-tetrahydronaphthalen-2-yl)pyrazin-2-yl]amino}butyacetate;

Methyl (3R,4S)-3-{[3,6-diethyl-5-(6-methoxy-2,3-dihydro-1H-inden-5-yl)pyrazin-2-yl]amino}-4-ethoxypyrrolidine-1-carboxylate;

Methyl (3R,4S)-3-{[3,6-diethyl-5-(3-methoxy-5,6,7,8-tetrahydronaphthalen-2-yl)pyrazin-2-yl]amino}-4-ethoxypyrrolidine-1-carboxylate;

5-{3,6-diethyl-5-[(1-ethylpropyl)amino]pyrazin-2-yl}-6-methoxyindan-1-one; and a pharmaceutically acceptable salt of any of said compounds.

17. A pharmaceutical composition comprising a compound of claim 1.

18. A method of antagonizing a $CRF_1$ receptor in a mammal, comprising administering to the mammal, a therapeutically effective amount of a compound of claim 1.

19. An article of manufacture comprising: a) a packaging material; b) a pharmaceutical agent comprising a compound of claim 1, which pharmaceutical agent is contained within the packaging material, and c) a label or package insert contained within said packaging material containing information about the intended use of said pharmaceutical agent.

20. A compound of claim 1 wherein, in a standard in vitro CRF receptor-binding assay, the compound exhibits an $IC_{50}$ value of 1 micromolar or less, wherein the assay is performed using IMR-32 human neuroblastoma cells.

21. A compound of claim 20 wherein the compound exhibits an $IC_{50}$ value of 100 nanomolar or less.

22. A compound of claim 21 wherein the compound exhibits an $IC_{50}$ value of 10 nanomolar or less.

23. A method of treating a disorder in a human, comprising administering to the human a therapeutically effective amount of a compound of claim 1, wherein the disorder is selected from the group consisting of anxiety-related disorders, post-traumatic stress disorder, eating disorders, drug or alcohol withdrawal symptoms, chemical dependencies and addictions, bipolar disorders, and depression.

24. The method according to claim 23, wherein the anxiety related disorder is generalized anxiety disorder.

* * * * *